US009145391B2

(12) United States Patent
Deschenes et al.

(10) Patent No.: US 9,145,391 B2
(45) Date of Patent: Sep. 29, 2015

(54) BIPYRIDYLAMINOPYRIDINES AS SYK INHIBITORS

(75) Inventors: Denis Deschenes, Lachine (CA); Michael D. Altman, Needham, MA (US); John Michael Ellis, Needham, MA (US); Christian Fischer, Natick, MA (US); Andrew M. Haidle, Cambridge, MA (US); Solomon D. Kattar, Arlington, MA (US); Alan B. Northrup, Reading, MA (US); Adam J. Schell, Decatur, GA (US); Graham F. Smith, Sudbury, MA (US); Brandon M. Taoka, Hoboken, NJ (US); Corey Bienstock, Natick, MA (US); Maria Emilia Di Francesco, Houston, TX (US); Anthony Donofrio, Cambridge, MA (US); Scott Peterson, Salem, MA (US); Kerrie B. Spencer, Woonsocket, RI (US); James Patrick Jewell, Somerville, MA (US); Amjad Ali, Freehold, NJ (US); David Jonathan Bennett, Doylestown, PA (US); Qun Dang, Westfield, NJ (US); John Wai, Harleysville, PA (US)

(73) Assignees: Merck Sharp & Dohme Corp., Rahway, NJ (US); Merck Canada Inc., Quebec (CA)

( * ) Notice: Subject to any disclaimer, the term of this patent is extended or adjusted under 35 U.S.C. 154(b) by 0 days.

(21) Appl. No.: 14/116,199

(22) PCT Filed: May 4, 2012

(86) PCT No.: PCT/US2012/036419
§ 371 (c)(1),
(2), (4) Date: Nov. 7, 2013

(87) PCT Pub. No.: WO2012/154518
PCT Pub. Date: Nov. 15, 2012

(65) Prior Publication Data
US 2014/0249130 A1 Sep. 4, 2014

Related U.S. Application Data

(60) Provisional application No. 61/484,472, filed on May 10, 2011.

(51) Int. Cl.
*C07D 213/73* (2006.01)
*C07D 401/14* (2006.01)
*C07D 401/12* (2006.01)
*C07D 409/14* (2006.01)
*C07D 417/14* (2006.01)
*C07D 471/04* (2006.01)

(52) U.S. Cl.
CPC ............ *C07D 401/14* (2013.01); *C07D 401/12* (2013.01); *C07D 409/14* (2013.01); *C07D 417/14* (2013.01); *C07D 471/04* (2013.01)

(58) Field of Classification Search
CPC ..................................................... C07D 213/73
USPC .................................. 546/257, 258; 514/334
See application file for complete search history.

(56) References Cited

U.S. PATENT DOCUMENTS

| | | | |
|---|---|---|---|
| 5,710,129 A | 1/1998 | Lynch et al. | |
| 5,958,957 A | 9/1999 | Andersen et al. | |
| 6,011,037 A | 1/2000 | Bar et al. | |
| 6,248,790 B1 | 6/2001 | Uckun et al. | |
| 6,432,963 B1 | 8/2002 | Hisamichi et al. | |
| 6,589,950 B1 | 7/2003 | Collingwood et al. | |
| 6,770,643 B2 | 8/2004 | Cox et al. | |
| 6,797,706 B1 | 9/2004 | Hisamichi et al. | |
| 6,897,207 B2 | 5/2005 | Cox et al. | |
| 6,897,208 B2 | 5/2005 | Edwards et al. | |
| 6,911,443 B2 | 6/2005 | Yura et al. | |
| 6,979,694 B2 | 12/2005 | Das et al. | |
| 7,060,827 B2 | 6/2006 | Singh et al. | |
| 7,122,542 B2 | 10/2006 | Singh et al. | |
| 7,244,739 B2 | 7/2007 | Cheng et al. | |
| 7,259,154 B2 | 8/2007 | Cox et al. | |
| 7,276,502 B2 | 10/2007 | Brenchley et al. | |
| 7,348,335 B2 | 3/2008 | Bethiel et al. | |
| 7,449,458 B2 | 11/2008 | Bhamidipati et al. | |
| 7,485,724 B2 | 2/2009 | Singh et al. | |
| 7,538,108 B2 | 5/2009 | Singh et al. | |
| 7,557,210 B2 | 7/2009 | Singh et al. | |
| 7,605,172 B2 | 10/2009 | Commons | |

(Continued)

FOREIGN PATENT DOCUMENTS

EP 1392684 9/2006
EP 1854793 A1 11/2007

(Continued)

OTHER PUBLICATIONS

EP Search Report corresponding to International Application No. PCT/US2012/036419, issued Oct. 8, 2014.
Atwell, et al., "A Novel Mode of Gleevec Binding is Revealed by the Structure of Spleen Tyrosine Kinase", The American Society for Biochemistry and Molecular Biology, Inc., 2004, pp. 55827-55832, vol. 279, Issue 53.
Cywin, et al, "Discovery and SAR of Novel [1,6]Naphthyridines as potent Inhibitors of Spleen Tyrosine Kinase (SYK)", Bioorganic & Medicinal Chemistry Letters, 2003, pp. 1415-1418, vol. 13.

(Continued)

*Primary Examiner* — Patricia L Morris
(74) *Attorney, Agent, or Firm* — Eric A. Meade; Catherine D. Fitch

(57) ABSTRACT

The present invention provides novel pyrimidine amines of formula I which are potent inhibitors of spleen tyrosine kinase, or are prodrugs thereof, and are useful in the treatment and prevention of diseases mediated by said enzyme, such as asthma, COPD and rheumatoid arthritis and cancer.

13 Claims, No Drawings

(56) References Cited

U.S. PATENT DOCUMENTS

| | | |
|---|---|---|
| 7,803,801 B2 | 9/2010 | Kodama et al. |
| 8,211,888 B2 | 7/2012 | Singh et al. |
| 8,551,984 B2 | 10/2013 | Altman et al. |
| 8,735,417 B2 | 5/2014 | Altman et al. |
| 8,759,366 B2 | 6/2014 | Childers et al. |
| 8,796,310 B2 | 8/2014 | Romeo et al. |
| 2004/0029902 A1 | 2/2004 | Singh et al. |
| 2004/0054179 A1 | 3/2004 | Yura et al. |
| 2006/0069084 A1 | 3/2006 | Burns et al. |
| 2006/0135543 A1 | 6/2006 | Singh et al. |
| 2006/0178407 A1 | 8/2006 | Argade et al. |
| 2006/0211657 A1 | 9/2006 | Singh et al. |
| 2006/0234483 A1 | 10/2006 | Araki et al. |
| 2006/0247262 A1 | 11/2006 | Baenteli et al. |
| 2007/0004626 A1 | 1/2007 | Masuda et al. |
| 2007/0015758 A1 | 1/2007 | Baruah et al. |
| 2007/0129362 A1 | 6/2007 | Bhamidipati et al. |
| 2007/0197782 A1 | 8/2007 | Clough et al. |
| 2008/0139535 A1 | 6/2008 | Anandan et al. |
| 2008/0182837 A1 | 7/2008 | Steurer et al. |
| 2011/0245205 A1 | 10/2011 | Altman et al. |
| 2012/0277192 A1 | 11/2012 | Altman et al. |
| 2013/0090309 A1 | 4/2013 | Romeo et al. |
| 2013/0225548 A1 | 8/2013 | Fujihara et al. |

FOREIGN PATENT DOCUMENTS

| | | |
|---|---|---|
| EP | 2441755 A1 | 4/2012 |
| JP | 2004203748 | 12/2002 |
| WO | WO9712871 | 4/1997 |
| WO | WO02096905 | 12/2002 |
| WO | WO02102313 A2 | 12/2002 |
| WO | WO03057659 | 7/2003 |
| WO | WO03078404 | 9/2003 |
| WO | WO2004005283 | 1/2004 |
| WO | WO2004080463 | 9/2004 |
| WO | WO2004087698 A2 | 10/2004 |
| WO | WO2004087699 | 10/2004 |
| WO | WO2005013996 | 2/2005 |
| WO | WO2006093247 | 2/2005 |
| WO | WO2005026158 | 3/2005 |
| WO | WO2005028475 | 3/2005 |
| WO | WO2005033103 | 4/2005 |
| WO | WO2005056547 | 6/2005 |
| WO | WO2006004865 | 1/2006 |
| WO | WO2006028833 | 3/2006 |
| WO | WO2006050480 | 5/2006 |
| WO | WO2006068770 | 6/2006 |
| WO | WO2006078846 | 7/2006 |
| WO | WO2006129100 | 12/2006 |
| WO | WO2006133426 | 12/2006 |
| WO | WO2006135915 | 12/2006 |
| WO | WO2007009681 | 1/2007 |
| WO | WO2007009773 | 1/2007 |
| WO | WO2007028445 | 3/2007 |
| WO | WO2007042298 | 4/2007 |
| WO | WO2007042299 | 4/2007 |
| WO | WO2007070872 | 6/2007 |
| WO | WO2007085540 | 8/2007 |
| WO | WO2007107469 | 9/2007 |
| WO | WO2007117692 A2 | 10/2007 |
| WO | WO2007120980 | 10/2007 |
| WO | WO2008024634 A1 | 2/2008 |
| WO | WO2008073687 | 6/2008 |
| WO | WO2008137605 A1 | 11/2008 |
| WO | WO2009012421 A1 | 1/2009 |
| WO | WO2009031011 | 3/2009 |
| WO | WO2009032861 A1 | 3/2009 |
| WO | WO2009084695 | 7/2009 |
| WO | WO2009097287 | 8/2009 |
| WO | WO2009102468 | 8/2009 |
| WO | WO2009103032 | 8/2009 |
| WO | WO2009131687 | 10/2009 |
| WO | WO2009136995 | 11/2009 |
| WO | WO2009145856 A1 | 12/2009 |
| WO | WO2010027500 | 3/2010 |
| WO | WO2010068257 | 6/2010 |
| WO | WO2010068258 | 6/2010 |
| WO | WO2011086085 A1 | 7/2011 |
| WO | WO2012041476 | 4/2012 |
| WO | WO2012154519 | 11/2012 |
| WO | WO2012154520 A1 | 11/2012 |
| WO | WO2014074421 | 5/2014 |
| WO | WO2014074421 A1 | 5/2014 |

OTHER PUBLICATIONS

Gura, T., "Cancer Models: Systems for Identifying New Drugs are often faulty", Science Magazine, 1997, pp. 1041-1042, vol. 278, Issue 5340.

International Preliminary Report on Patentability, PCT/US2012/036419, Nov. 21, 2013.

International Search Report, PCT/US2012/036419, Aug. 7, 2012.

Johnson, et al, "Relationships between drug activity in NCI preclinical in vitro and in vivo models and early clinical trials", British Journal of Cancer, 2001, pp. 1424-1431, vol. 64(10).

Pamuk et al, "Spleen tyrosine kinase inhibition in the treatment of autoimmune, allergic and autoinflammatory diseases", Arthritis Research & Therapy, 2010, pp. 1-11, vol. 12, Issue :222.

Pearce, H.L. et al, "Failure modes in anticancer drug discovery and development", Cancer Drug Design and Discovery, 2008, Edited by Stephen Neidle—pp. 424-435, Chapter 18.

Simone, J., Introduction, Part XIV, Oncology, Cecil Textbook of Medicine, 1996, pp. 1004-1010, vol. 1—20th Ed.

Yamamoto, et al, "The Orally Available Spleen Tyrosine Kinase inhibitor (2-[7-(3,4-Dimethoxyphenyl)-imidazo[1,2-c]pyrimidin-5-ylamino]-nicotinamide Dihydrochloride (BAY 61-3606) Blocks Antigen-Induced Airway Inflammation in Rodents", The Journal of Pharmacology and Experimental Therapeutics, 2003, pp. 1174-1181, vol. 306(3).

BIPYRIDYLAMINOPYRIDINES AS SYK INHIBITORS

CROSS REFERENCE TO RELATED APPLICATIONS

This application is a U.S. National Phase application under 35 U.S.C. §371 of PCT Application No. PCT/US2012/036419, filed May 4, 2012, which claims priority under 35 U.S.C. §119(e) from U.S. Provisional Application No. 61/484,472, filed May 10, 2011.

BACKGROUND OF THE INVENTION

Spleen Tyrosine Kinase (Syk) is a protein tyrosine kinase which has been described as a key mediator of immunoreceptor signalling in a host of inflammatory cells including mast cells, B-cells, macrophages and neutrophils. These immunoreceptors, including Fc receptors and the B-cell receptor, are important for both allergic diseases and antibody-mediated autoimmune diseases and thus pharmacologically interfering with Syk could conceivably treat these disorders.

Allergic rhinitis and asthma are diseases associated with hypersensitivity reactions and inflammatory events involving a multitude of cell types including mast cells, eosinophils, T cells and dendritic cells. Following exposure to allergen, high affinity immunoglobulin receptors for IgE and IgG become cross-linked and activate downstream processes in mast cells and other cell types leading to the release of pro-inflammatory mediators and airway spasmogens. In the mast cell, for example, IgE receptor cross-linking by allergen leads to release of mediators including histamine from pre-formed granules, as well as the synthesis and release of newly synthesized lipid mediators including prostaglandins and leukotrienes.

Syk kinase is a non-receptor linked tyrosine kinase which is important in transducing the downstream cellular signals associated with cross-linking $Fc_{epsilon}R1$ and or $Fc_{epsilon}R1$ receptors, and is positioned early in the signalling cascade. In mast cells, for example, the early sequence of $Fc_{epsilon}R1$ signalling following allergen cross-linking of receptor-IgE complexes involves first Lyn (a Src family tyrosine kinase) and then Syk. Inhibitors of Syk activity would therefore be expected to inhibit all downstream signalling cascades thereby alleviating the immediate allergic response and adverse events initiated by the release of pro-inflammatory mediators and spasmogens (Wong et al 2004, Expert Opin. Investig. Drugs (2004) 13 (7) 743-762).

Recently, it has been shown that the Syk kinase inhibitor R112 (Rigel), dosed intranasally in a phase VII study for the treatment of allergic rhinitis, gave a statistically significant decrease in PGD2, a key immune mediator that is highly correlated with improvements in allergic rhinorrhea, as well as being safe across a range of indicators, thus providing the first evidence for the clinical safety and efficacy of a topical Syk kinase inhibitor. (Meltzer, Eli O.; Berkowitz, Robert B.; Grossbard, Elliott B, Journal of Allergy and Clinical Immunology (2005), 115(4), 791-796). In a more recent phase II clinical trial for allergic rhinitis (Clinical Trials.gov Identifier NCT0015089), R112 was shown as having a lack of efficacy versus placebo.

Rheumatoid Arthritis (RA) is an auto-immune disease affecting approximately 1% of the population. It is characterised by inflammation of articular joints leading to debilitating destruction of bone and cartilage. Recent clinical studies with Rituximab, which causes a reversible B cell depletion, (J. C. W. Edwards et al 2004, New Eng. J. Med. 350: 2572-2581) have shown that targeting B cell function is an appropriate therapeutic strategy in auto-immune diseases such as RA. Clinical benefit correlates with a reduction in auto-reactive antibodies (or Rheumatoid Factor) and these studies suggest that B cell function and indeed auto-antibody production are central to the ongoing pathology in the disease.

Studies using cells from mice deficient in the Spleen Tyrosine Kinase (Syk) have demonstrated a non-redundant role of this kinase in B cell function. The deficiency in Syk is characterized by a block in B cell development (M. Turner et al 1995 Nature 379: 298-302 and Cheng et al 1995, Nature 378: 303-306). These studies, along with studies on mature B cells deficient in Syk (Kurasaki et al 2000, Immunol. Rev. 176:19-29), demonstrate that Syk is required for the differentiation and activation of B cells. Hence, inhibition of Syk in RA patients is likely block B cell function and thereby reduce Rheumatoid Factor production. In addition to the role of Syk in B cell function, and of further relevance to the treatment of RA, is the requirement for Syk activity in Fc receptor (FcR) signalling. FcR activation by immune complexes in RA has been suggested to contribute to the release of multiple pro-inflammatory mediators.

The present invention relates to novel compounds, which are inhibitors of Syk kinase activity, or are prodrugs of such inhibitors. These compounds therefore have potential therapeutic benefit in the treatment of disorders associated with inappropriate Syk activity, in particular in the treatment and prevention of disease states mediated by Syk. Such disease states may include inflammatory, allergic and autoimmune diseases, for example, asthma, chronic obstructive pulmonary disease (COPD), adult respiratory distress syndrome (ARDS), ulcerative colitis, Crohns disease, bronchitis, dermatitis, allergic rhinitis, psoriasis, scleroderma, urticaria, rheumatoid arthritis, idiopathic thrombocytopenic purpura (ITP), multiple sclerosis, cancer, HN and lupus.

SUMMARY OF THE INVENTION

The present invention provides novel compounds that are potent inhibitors of Syk, or are prodrugs thereof, as well as pharmaceutical compositions containing such compounds. As Syk inhibitors or prodrugs thereof, compounds of the present invention are useful in the treatment and prevention of diseases and disorders mediated by the Syk protein; such diseases and disorders include, but are not limited to, asthma, COPD, rheumatoid arthritis, cancer and idiopathic thrombocytopenic purpura.

DETAILED DESCRIPTION OF THE INVENTION

The present invention provides compounds of formula I:

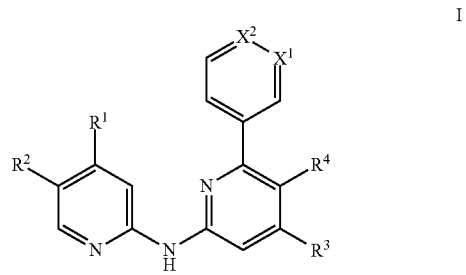

or a pharmaceutically acceptable salt thereof,
wherein
$R^1$ is $C_{1-4}$alkyl, $C_{1-4}$fluoroalkyl, $C_{3-6}$cycloalkyl or $C_{1-4}$alkoxy;

$R^2$ is H or halogen;
$R^3$ is H, halogen, $NR^bR^c$, $C_{1-4}$alkyl, $C_{1-4}$haloalkyl, $C_{3-6}$cycloalkyl or $C_{1-4}$hydroxyalkyl;
$R^4$ is H or halogen;
one of $X^1$ and $X^2$ is N, and the other is C—F, C-Q or C—Y—Z;
Q is selected from (a) $C_{1-4}$alkyl optionally substituted with 1 to 2 groups independently selected from $OR^a$ and $CO_2R^a$, and (b) $NH$—$C_{1-4}$alkyl optionally substituted with $CO_2R^a$;
Y is selected from the group consisting of (a) a bond, (b) —$O(CH_2)_{0-1}$—, (c) —$NH(CH_2)_{0-1}$—, (d) —$C(R^5)(R^6)$—, and (e) —C(O)—;
$R^5$ is H, OH, $C_{1-4}$alkoxy or halogen;
$R^6$ is H, $C_{1-4}$alkyl, $C_{1-4}$haloalkyl, $C_{3-6}$cycloalkyl or $C_{1-4}$hydroxyalkyl;
Z is (a) aryl or a carbocycle each optionally substituted with 1-5 groups independently selected from $C_{1-4}$alkyl, $OR^a$, $CO_2R^a$, and $CONR^bR^c$, or (b) heteroaryl or a 4- to 10-membered mono- or bicyclic heterocycle each optionally substituted with 1 or 2 groups independently selected from oxo, $OR^a$, $CO_2R^a$, $CONR^bR^c$, $COR^d$, $NR^bR^c$, $NHC(O)OR^a$, $NHCOR^d$, $NHCONR^bR^c$, and cyclohexyl optionally substituted with $CO_2R^a$;
$R^a$ is selected from the group consisting of:
(i) H;
(ii) $C_{1-8}$alkyl;
(iii) a group of the formula -M-$R^{CH}$, wherein
M is a bond or —$(CH_2)_{1-2}$—;
$R^{CH}$ is (a) aryl or carbocycle optionally substituted with 1-3 groups independently selected from halo, $C_{1-4}$alkyl, or $C_{1-4}$alkoxy; or (b) a 5- to 6-membered monocyclic heterocycle containing 1 or 2 heteroatoms independently selected from the group consisting of N and O, wherein said heterocycle of $R^{CH}$ is optionally substituted with 1 or 2 groups independently selected from the group consisting of oxo and $C_{1-3}$ alkyl;
(iv) a group of the formula —$(CH_2)_{1-2}$—$R^e$ or —$(CH_2)_2$—O—$(CH_2)_2$—$R^e$ wherein
$R^e$ is $CO_2R^{e1}$, $C(O)N(R^{e2})_2$, or —$O(CO)R^{e1}$;
$R^{e1}$ is $C_{1-4}$alkyl; and
$R^{e2}$ is H or $C_{1-4}$alkyl;
(v) a group of the formula —$(CH_2)_2$—$R^f$,
$R^f$ is OH, —$OC_{1-4}$alkyl, $NH_2$, —$N(H)(C_{1-4}$alkyl) or $N(C_{1-4}$alkyl$)_2$;
(vi) a group of the formula

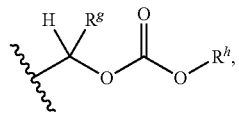

wherein
$R^g$ is H or $C_{1-4}$alkyl; and
$R^h$ is $C_{1-4}$ alkyl, $C_{3-6}$cycloalkyl, or phenyl; and,
(vii) a group of the formula

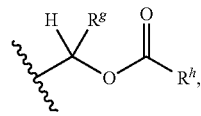

wherein $R^g$ and $R^h$ are as set forth above;
$R^b$ and $R^c$ are each independently selected from H and $C_{1-4}$alkyl; or
$R^b$, $R^c$ and the nitrogen atom to which they are attached together form a 4- to 6-membered ring optionally having an additional heteroatom selected from N—$R^a$, O and S, wherein said ring is optionally substituted with a group selected from $CO_2R^a$ and oxo;
$R^d$ is (a) $C_{1-4}$alkyl optionally substituted with $NR^bR^c$, O-aryl, aryl, heteroaryl, or V—W, (b) aryl, (c) heteroaryl, (d) V—W, or (e) a group selected from 1-isoindolinone; 2-indolinone, fluorenyl (optionally substituted with oxo), tetrahydrocarbazolyl, and dibenzo[b,d]furanyl; wherein V and W are each independently selected from aryl and heteroaryl, and aryl and heteroaryl in (a) through (d) are each optionally substituted with 1-3 groups independently selected from (i) $C_{1-4}$alkyl, (ii) $C_{1-4}$haloalkyl, (iii) CN, (iv) halogen, (v) $OR^a$, (vi)phenoxy, (vii) $CH_2$-aryl, (viii) $CH_2$-heteroaryl, (ix) $NR^bR^c$, (x) $CONR^bR^c$, (xi) $NHCOC_{1-4}$alkyl, and (xii) $SO_2C_{1-4}$alkyl.

In one group of formula I are compounds wherein $R^a$ is H or $C_{1-4}$alkyl.

In one group of formula I are compounds wherein $X^1$ is N. In one subset thereof are compounds wherein $X^2$ is C—Y—Z. In another subset thereof are compounds wherein $X^2$ is C-Q, and Q is hydroxy-substituted $C_{1-4}$alkyl or NH—$C_{1-4}$alkyl substituted with $CO_2R^a$.

In another group of formula I are compounds wherein Y is a bond, —NH— or —$C(R^5)(R^6)$—. In one subset thereof are compounds wherein Y is a bond. In another subset thereof are compounds wherein Y is —NH—. In yet another subset thereof, Y is —$C(R^5)(R^6)$—; and examples of —$C(R^5)(R^6)$— include —$CH_2$—, —$C(CH_3)(OH)$—, —$C(cPr)(OH)$—, —$C(Et)(OH)$—, —$CHCH_3$—, —$C(CH_3)(F)$—, and —$C(CH_3)(OCH_3)$—.

In another group of formula I are compounds wherein Z is (a) an optionally benzofused $C_{3-6}$cycloalkyl optionally substituted with 1 to 5 groups independently selected from $C_{1-4}$alkyl, $OR^a$, $CO_2R^a$, and $CONR^bR^c$, or (b) a 4- to 10-membered mono- or bicyclic heterocycle optionally substituted with 1 or 2 groups independently selected from oxo, $OR^a$, $CO_2R^a$, $CONR^bR^c$, $COR^d$, $NR^bR^c$, $NHC(O)OR^a$, $NHCOR^d$, $NHCONR^bR^c$, and cyclohexyl optionally substituted with $CO_2R^a$.

In another group of formula I are compounds wherein Z is an optionally benzofused $C_{3-6}$cycloalkyl optionally substituted with 1 to 5 groups independently selected from $C_{1-4}$alkyl, $OR^a$, $CO_2R^a$, and $CONR^bR^c$. In one subset thereof are compounds wherein Z is $C_{4-6}$cycloalkyl optionally substituted with 1 to 4 groups independently selected from methyl, $OR^a$, $CO_2R^a$, and $CONR^bR^c$, In another subset thereof are compounds wherein Z is cyclohexyl substituted with $CO_2R^a$, or $CONR^bR^c$, and optionally further substituted with 1 to 3 groups independently selected from OH and methyl. Examples of Z within this group include cyclohexanecarboxylic acid, $C_{1-4}$alkyl cyclohexanecarboxylate, 4-hydroxy-2,2-dimethyl-cyclohexanecarboxylic acid (or carboxylate), 2-methylcyclohexanecarboxylic acid (or carboxylate), 2,2-dimethylcyclohexanecarboxylic acid (or carboxylate), cyclobutyl, 5-hydroxy-5,6,7,8-tetrahydronaphthalene-2-carboxylic acid, 4-hydroxy-2,2-dimethylcyclohexane-carboxamide.

In another group of formula I are compounds wherein Z is a 4- to 10-membered mono- or bicyclic heterocycle optionally substituted with 1 or 2 groups independently selected from oxo, $OR^a$, $CO_2R^a$, $CONR^bR^c$, $COR^d$, $NR^bR^c$, $NHC(O)OR^a$, $NHCOR^d$, $NHCONR^bR^c$, and cyclohexyl optionally substituted with $CO_2R^a$. In one subset thereof are compounds wherein Z is selected from azetidinyl, pyrrolidinyl and piperidinyl each of which is optionally substituted with 1 or 2 groups independently selected from oxo, $OR^a$, $CO_2R^a$, $CONR^bR^c$, $COR^d$, $NR^bR^c$, $NHC(O)OR^a$, $NHCOR^d$, $NHCONR^bR^c$, and cyclohexyl optionally substituted with $CO_2R^a$. Examples of 4- to 10-membered mono- or bicyclic heterocycle include azetidine, pyrrolidine, piperidine, piperazine, decahydroisoquinoline, and morpholine.

In another group of formula I are compounds wherein $R^1$ is $C_{1-4}$alkyl, $C_{1-2}$fluoroalkyl, $C_{3-4}$cycloalkyl or $C_{1-2}$alkoxy. Examples of $R^1$ include methyl, difluoromethyl, trifluoromethyl, methoxy and cyclopropyl.

In another group of formula I are compounds wherein $R^2$ is H or F.

In another group of formula I are compounds wherein $R^3$ is H, $NR^bR^c$, $C_{1-4}$alkyl, $C_{3-6}$cycloalkyl, or $C_{1-4}$hydroxyalkyl. Examples of $R^3$ include methyl, amino, cyclopropyl, and 2-hydroxy-2-propyl.

In another group of formula I are compounds having formula Ia:

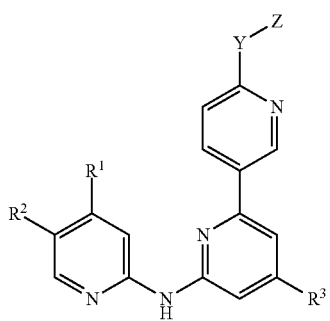

or a pharmaceutically acceptable salt thereof; wherein

Y is a bond, —NH— or —C($R^5$)($R^6$)—;

Z is (a) an optionally benzofused $C_{3-6}$cycloalkyl optionally substituted with 1 to 5 groups independently selected from $C_{1-4}$alkyl, $OR^a$, $CO_2R^a$, and $CONR^bR^c$, or (b) a 4- to 10-membered mono- or bicyclic heterocycle optionally substituted with 1 or 2 groups independently selected from oxo, $OR^a$, $CO_2R^a$, $CONR^bR^c$, $COR^d$, $NR^bR^c$, $NHC(O)OR^a$, $NHCOR^d$, $NHCONR^bR^c$, and cyclohexyl optionally substituted with $CO_2R^a$; and $R^1$, $R^2$, $R^3$, $R^5$, $R^6$, $R^a$, $R^b$, $R^c$, and $R^d$ are as defined under formula I.

In one subset of formula Ia are compounds wherein Z is $C_{4-6}$cycloalkyl optionally substituted with 1 to 4 groups independently selected from methyl, OH, $CO_2R^a$, and $CONR^bR^c$. In one embodiment Z is cyclohexyl substituted with $CO_2R^a$ or $CONR^bR^c$, and optionally further substituted with 1 to 3 groups independently selected from methyl and OH.

In another subset of formula Ia are compounds wherein Z is a 4- to 6-membered heterocycle optionally substituted with 1 or 2 groups independently selected from oxo, $OR^a$, $CO_2R^a$, $CONR^bR^c$, $COR^d$, $NR^bR^c$, $NHC(O)OR^a$, $NHCOR^d$, and $NHCONR^bR^c$. In one embodiment thereof said heterocycle is selected from 4-piperidinyl, 1-piperidinyl, 1-piperazinyl, 1-pyrrolidinyl, 1-azetidinyl, and 4-morpholinyl.

In another subset of formula Ia are compounds wherein Y is a bond and Z is (a)

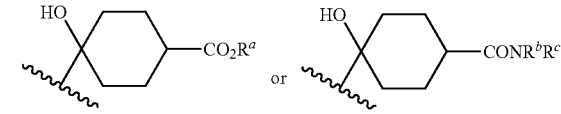

each optionally further substituted with 1 to 2 methyl groups; or (b)

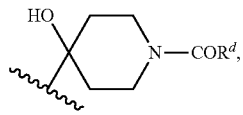

wherein $R^d$ is selected from (a) aryl, (b) heteroaryl, and (c) V—W; V and W are each independently selected from aryl and heteroaryl; and aryl and heteroaryl of (a) through (c) are each optionally substituted with 1-3 groups independently selected from (i) $C_{1-4}$alkyl, $C_{1-4}$haloalkyl, (iii) CN, (iv) halogen, (v) $OR^a$, (vi) phenoxy, (vii) $CH_2$-aryl, (viii) $CH_2$-heteroaryl, (ix) $NR^bR^c$, (x) $CONR^bR^c$, (xi) $NHCOC_{1-4}$alkyl, and (xii) $SO_2C_{1-4}$alkyl.

In another subset of formula Ia are compounds wherein Y is a bond and Z is 1-azetidinyl, 1-pyrrolidinyl or 1-piperidinyl, wherein each is optionally substituted with a group selected from $CO_2R^a$, $CONR^bR^c$, $COR^d$, $NR^bR^c$, $NHC(O)$ $OR^a$, $NHCOR^d$, and $NHCONR^bR^c$. In one embodiment thereof Z is substituted with $CONR^bR^c$. In another embodiment Z is substituted with $COR^d$ or $NHCOR^d$, wherein $R^d$ is selected from (a) aryl, (b) heteroaryl, and (c) V—W; V and W are each independently selected from aryl and heteroaryl; and aryl and heteroaryl of (a) through (c) are each optionally substituted with 1-3 groups independently selected from (i) $C_{1-4}$alkyl, (ii) $C_{1-4}$haloalkyl, (iii) CN, (iv) halogen, (v) $OR^a$, (vi) phenoxy, (vii) $CH_2$-aryl, (viii) $CH_2$-heteroaryl, (ix) $NR^bR^c$, (x) $CONR^bR^c$, (xi) $NHCOC_{1-4}$alkyl, and (xii) $SO_2C_{1-4}$alkyl.

In another subset of formula Ia are compounds wherein Y is —NH— or —C($R^5$)($R^6$)— and Z is cyclohexyl substituted with a group selected from $CO_2R^a$ and $CONR^bR^c$, and optionally further substituted with 1 or 2 methyl groups. In one embodiment thereof Y is —C($R^5$)($R^6$)—, $R^5$ is selected from H, OH, methoxy and F, and $R^6$ is selected from H, methyl, ethyl, and cyclopropyl; $R^5$ is preferably OH.

In another subset of formula Ia are compounds wherein Y is —NH— and Z is (a) a 2-pyrrolidone, (b)

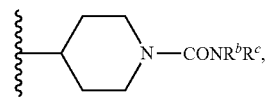

(c)

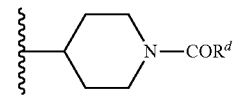

or (d) cyclohexyl. In one embodiment thereof Z is

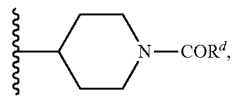

and $R^d$ is selected from (a) aryl, (b) heteroaryl, and (c) V—W; V and W are each independently selected from aryl and heteroaryl; and aryl and heteroaryl of (a) through (c) are each optionally substituted with 1-3 groups independently selected from (i) $C_{1-4}$alkyl, (ii) $C_{1-4}$haloalkyl, (iii) CN, (iv) halogen, (v) $OR^a$, (vi) phenoxy, (vii) $CH_2$-aryl, (viii) $CH_2$-heteroaryl, (ix) $NR^bR^c$, (x) $CONR^bR^c$, (xi) $NHCOC_{1-4}$alkyl, and (xii) $SO_2C_{1-4}$alkyl.

In another subset of formula Ia are compounds wherein $R^a$ is H or $C_{1-4}$alkyl.

In another group of formula I are compounds having the formula Ib:

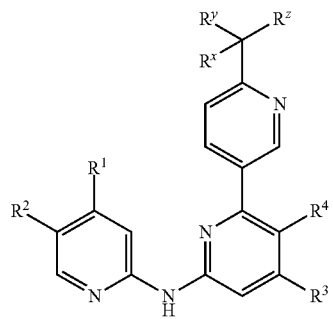

or a pharmaceutically acceptable salt thereof; wherein
$R^x$ is H, $C_{1-4}$alkyl, $C_{1-4}$haloalkyl, $C_{3-6}$cycloalkyl or $C_{1-4}$hydroxyalkyl;
$R^y$ is cyclohexyl substituted with a group selected from $CO_2R^a$ and $CONR^bR^c$, and optionally further substituted with 1 to 2 methyl groups; or
$R^x$, $R^y$ and the carbon atom to which they are both attached together form an optionally benzofused $C_{4-6}$cycloalkyl substituted with a group selected from $CO_2R^a$ and $CONR^bR^c$, and optionally substituted with 1 to 2 methyl groups; or
$R^x$, $R^y$ and the carbon atom to which they are both attached together form 1-$COR^d$ substituted 4-piperidyl, wherein $R^d$ is selected from (a) aryl, (b) heteroaryl, and (c) V—W; V and W are each independently selected from aryl and heteroaryl; and aryl and heteroaryl of (a) through (c) are each optionally substituted with 1-3 groups independently selected from (i) $C_{1-4}$alkyl, (ii) $C_{1-4}$haloalkyl, (iii) CN, (iv) halogen, (v) $OR^a$, (vi) phenoxy, (vii) $CH_2$-aryl, (viii) $CH_2$-heteroaryl, (ix) $NR^bR^c$, (x) $CONR^bR^c$, (xi) $NHCOC_{1-4}$alkyl, and (xii) $SO_2C_{1-4}$alkyl.
$R^z$ is H, $OR^a$ or F; and
$R^1$, $R^2$, $R^3$, $R^4$, $R^a$, $R^b$, $R^c$ and $R^d$ are as defined in formula I.

In one subset of formula Ib are compounds wherein $R^z$ is H, OH, methoxy, or F. In one embodiment thereof $R^z$ is OH.

In another subset of formula Ib are compounds wherein $R^x$ is methyl, ethyl, or cyclopropyl, and $R^y$ is cyclohexyl substituted with a group selected from $CO_2R^a$ and $CONR^bR^c$, and optionally further substituted with 1 to 2 methyl groups.

In another subset of formula Ib are compounds wherein $R^x$, $R^y$ and the carbon atom to which they are both attached together form a $C_{4-6}$cycloalkyl substituted with a group selected from $CO_2R^a$ and $CONR^bR^c$, and optionally substituted with 1 to 2 methyl groups. In one embodiment $R^x$, $R^y$ and the carbon atom to which they are both attached together form cyclohexyl substituted with a group selected from $CO_2R^a$ and $CONR^bR^c$, and optionally substituted with 1 to 2 methyl groups.

In another subset of formula Ib are compounds wherein $R^1$ is methyl, methoxy, cyclopropyl, or a fluorinated methyl; $R^2$ is H or F; $R^3$ is methyl, cyclopropyl or 2-hydroxy-2-propyl; $R^4$ is H; $R^x$ is methyl, ethyl, or cyclopropyl; $R^y$ is cyclohexyl substituted with a group selected from $CO_2R^a$ and $CONR^bR^c$, and optionally further substituted with 1 to 2 methyl groups; and $R^z$ is OH. In one embodiment thereof $R^1$ is difluoromethyl or trifluoromethyl; $R^2$ is H; and $R^3$ is methyl.

In another subset of formula Ib are compounds wherein $R^a$ is H or $C_{1-4}$alkyl.

In another group of formula I are compounds having the formula Ic:

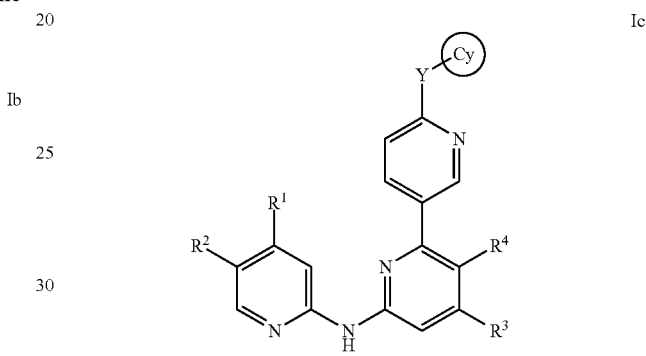

or a pharmaceutically acceptable salt thereof; wherein
Y is a bond or —NH—;
Cy is (a) cyclohexyl substituted with $CO_2R^a$, and optionally further substituted with 1 to 2 methyl groups; or (b) HET;
HET is azetidinyl, pyrrolidinyl, or piperidinyl, each of which is optionally substituted with 1 to 2 groups independently selected from oxo, $OR^a$, $CO_2R^a$, $CONR^bR^c$, $COR^d$, $NR^bR^c$, $NHC(O)OR^a$, $NHCOR^d$, and $NHCONR^bR^c$; and
$R^1$, $R^2$, $R^3$, $R^4$, $R^a$, $R^b$, $R^c$, and $R^d$ are as defined in claim 1.

In one subset of formula Ic are compounds wherein Y is a bond, and Cy is selected from: (a)

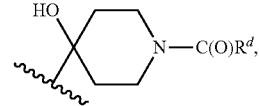

and (b)

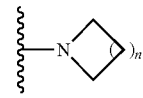

substituted with a group selected from $CO_2R^a$, $NHCOR^d$, $NR^bR^c$, $NHC(O)OC_{1-4}$alkyl, $NHC(O)R^d$, $NHC(O)NH_2$, and n is 1, 2 or 3.

In another subset of formula Ic are compounds wherein Y is —NH—, and Cy is cyclohexyl substituted with $CO_2R^a$, and optionally further substituted with 1 to 2 methyl groups.

In another subset of formula Ic are compounds wherein Y is —NH—, and Cy is

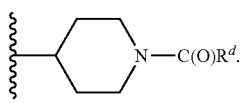

In one embodiment are compounds wherein $R^d$ is selected from (a) —CH$_2$-substituted with aryl, heteroaryl, or V—W, (b) aryl, (c) heteroaryl, and (d) V—W; wherein V and W are each independently selected from aryl and heteroaryl; and aryl and heteroaryl in (a) through (d) are each optionally substituted with 1 to 2 groups independently selected from (i) C$_{1-4}$alkyl, (ii) C$_{1-4}$haloalkyl, (iii) CN, (iv) halogen, (v) OR$^a$, (vi) phenoxy, (vii) CH$_2$-aryl, (viii) CH$_2$-heteroaryl, (ix) NR$^b$R$^c$, (x) CONR$^b$R$^c$, (xi) NHCOC$_{1-4}$alkyl, and (xii) SO$_2$C$_{1-4}$alkyl.

In another subset of formula Ic are compounds wherein $R^a$ is H or C$_{1-4}$alkyl.

In another group of formula I are compounds having the formula Id:

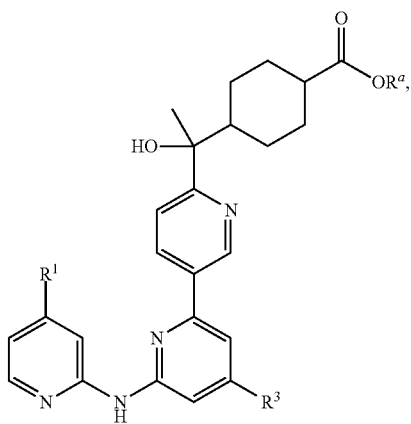

or a pharmaceutically acceptable salt thereof; wherein $R^1$ is C$_{1-4}$alkyl or C$_{1-2}$fluoroalkyl;

$R^3$ is C$_{1-4}$alkyl or C$_{1-2}$fluoroalkyl; and $R^a$ is selected from the group consisting of:
(i) H;
(ii) C$_{1-8}$alkyl;
(iii) a group of the formula -M-R$^{CH}$, wherein
 M is a bond or —(CH$_2$)$_{1-2}$—;
 R$^{CH}$ is (a) aryl or carbocycle optionally substituted with 1-3 groups independently selected from halo, C$_{1-4}$alkyl, or C$_{1-4}$alkoxy; or (b) a 5- to 6-membered monocyclic heterocycle containing 1 or 2 heteroatoms independently selected from the group consisting of N and O, wherein said heterocycle of R$^{CH}$ is optionally substituted with 1 or 2 groups independently selected from the group consisting of oxo and C$_{1-3}$ alkyl;
(iv) a group of the formula —(CH$_2$)$_{1-2}$—R$^e$ or —(CH$_2$)$_2$—O—(CH$_2$)$_2$—R$^e$ wherein
 R$^e$ is CO$_2$R$^{e1}$, C(O)N(R$^{e2}$)$_2$, or —O(CO)R$^{e1}$;
 R$^{e1}$ is C$_{1-4}$alkyl; and
 R$^{e2}$ is H or C$_{1-4}$alkyl;
(v) a group of the formula —(CH$_2$)$_2$—R$^f$,
 R$^f$ is OH, —OC$_{1-4}$alkyl, NH$_2$, —N(H)(C$_{1-4}$alkyl) or N(C$_{1-4}$alkyl)$_2$;

(vi) a group of the formula

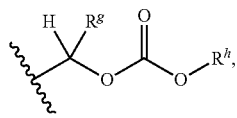

wherein
 R$^g$ is H or C$_{1-4}$alkyl; and
 R$^h$ is C$_{1-4}$alkyl, C$_{3-6}$cycloalkyl, or phenyl; and
(vii) a group of the formula

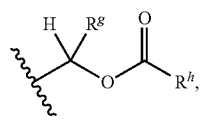

wherein R$^g$ and R$^h$ are as set forth above.

In one subset of formula Id are compounds wherein R$^1$ is difluoromethyl and R$^3$ is methyl.

In another subset of formula Id are compounds wherein $R^a$ is selected from the group consisting of:
(i) H;
(ii) C$_{1-8}$alkyl;
(iii) a group of the formula -M-R$^{CH}$, wherein
 M is a bond or —(CH$_2$)$_{1-2}$—;
 R$^{CH}$ is (a) unsubstituted phenyl or unsubstituted cycloalkyl; or (b) a 5- to 6-membered monocyclic heterocycle selected from the group consisting of dioxanyl, morpholinyl, and dioxolyl, wherein said heterocycle of R$^{CH}$ is optionally substituted with 1 oxo;
(iv) a group of the formula —(CH$_2$)$_{1-2}$—R$^e$ or —(CH$_2$)$_2$—O—(CH$_2$)$_2$—R$^e$ wherein
 R$^e$ is CO$_2$R$^{e1}$, C(O)N(R$^{e2}$)$_2$, or —O(CO)R$^{e1}$;
 R$^{e1}$ is C$_{1-4}$alkyl; and
 R$^{e2}$ is H or C$_{1-4}$alkyl;
(v) a group of the formula —(CH$_2$)$_2$—R$^f$,
 R$^f$ is OH, —OC$_{1-4}$alkyl, NH$_2$, —N(H)(C$_{1-4}$alkyl) or N(C$_{1-4}$alkyl)$_2$;
(vi) a group of the formula

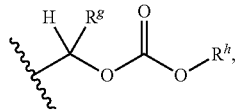

wherein
 R$^g$ is H or methyl; and
 R$^h$ is C$_{1-4}$alkyl or cyclohexyl; and
(vii) a group of the formula

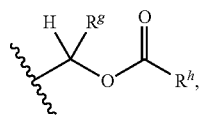

wherein
 R$^g$ is H or methyl; and
 R$^h$ is C$_{1-4}$alkyl.

In another subset of formula Id are compounds wherein $R^a$ is H or C$_{1-4}$alkyl.

In another subset of formula Id are compounds wherein the moiety

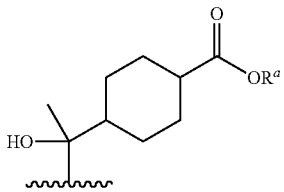

has the configuration

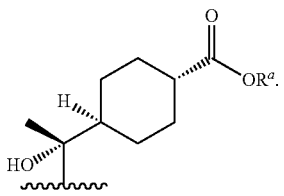

In another subset of formula Id are compounds wherein the moiety

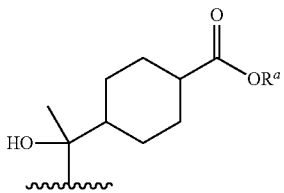

has the configuration

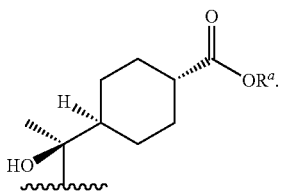

Representative compounds of the instant invention are exemplified herein below. A subset of the representative compounds of the present invention are as follows, where each named compound is intended to encompass its individual isomers, mixtures thereof (including racemates and diastereomeric mixtures), as well as pharmaceutically acceptable salts thereof:

trans-4-(1-hydroxy-1-(4-methyl-6-(4-(trifluoromethyl)pyridin-2-ylamino)-2,3'-bipyridin-6'-yl)ethyl)cyclohexanecarboxylic acid trans-4-[(4-cyclopropyl-6-{[4-(difluoromethyl)pyridin-2-yl]amino}-2,3'-bipyridin-6'-yl)-1-hydroxyethyl]cyclohexanecarboxylic acid (1,2-cis)-4-[1-(6-{[4-(difluoromethyl)pyridin-2-yl]amino}-4-methyl-2,3'-bipyridin-6'-yl)-1-hydroxyethyl]-2-methylcyclohexanecarboxylic acid trans-4-[(6-{[4-(difluoromethyl)pyridin-2-yl]amino}-4-methyl-2,3'-bipyridin-6'-yl)-1-hydroxyethyl]cyclohexanecarboxylic acid trans-4-[1-hydroxy-1-{4-methyl-6-[(4-methylpyridin-2-yl)amino]-2,3'-bipyridin-6'-yl}ethyl]cyclohexanecarboxylic acid trans-4-[1-hydroxy-1-{6-[(4-methoxypyridin-2-yl)amino]-4-methyl-2,3'-bipyridin-6'-yl}ethyl]cyclohexanecarboxylic acid trans-4-[{6-[(4-cyclopropylpyridin-2-yl)amino]-4-methyl-2,3'-bipyridin-6'-yl}-1-hydroxyethyl)cyclohexanecarboxylic acid trans-4-[(4-methyl-6-{[4-(trifluoromethyl)pyridin-2-yl]amino}-2,3'-bipyridin-6'-yl)methyl]cyclohexanecarboxylic acid trans-4-((6-(4-(difluoromethyl)pyridin-2-ylamino)-4-methyl-2,3'-bipyridin-6'-yl)-1-fluoroethyl)cyclohexanecarboxylic acid trans-4-[(4-methyl-6-{[4-(trifluoromethyl)pyridin-2-yl]amino}-2,3'-bipyridin-6'-yl)ethyl]cyclohexanecarboxylic acid (trans-4-[{6-[(5-fluoro-4-methylpyridin-2-yl)amino]-4-methyl-2,3'-bipyridin-6'-yl}-1-hydroxyethyl]cyclohexanecarboxylic acid trans-4-[[6-{[4-(difluoromethyl)pyridin-2-yl]amino}-4-(2-hydroxypropan-2-yl)-2,3'-bipyridin-6'-yl]-1-hydroxyethyl}cyclohexanecarboxylic acid trans-4-[1-(6-{[4-(difluoromethyl)pyridin-2-yl]amino}-4-methyl-2,3'-bipyridin-6'-yl)-1-methoxyethyl]cyclohexanecarboxylic acid cis-4-hydroxy-4-(4-methyl-6-{[4-(trifluoromethyl)pyridin-2-yl]amino}-2,3'-bipyridin-6'-yl)cyclohexanecarboxylic acid 5-hydroxy-5-(4-methyl-6-{[4-(trifluoromethyl)pyridin-2-yl]amino}-2,3'-bipyridin-6'-yl)-5,6,7,8-tetrahydronaphthalene-2-carboxylic acid 4-hydroxy-2,2-dimethyl-4-(4-methyl-6-{[4-(trifluoromethyl)pyridin-2-yl]amino}-2,3'-bipyridin-6'-yl)cyclohexanecarboxylic acid trans-4-[cyclopropyl(hydroxy)(4-methyl-6-{[4-(trifluoromethyl)pyridin-2-yl]amino}-2,3'-bipyridin-6'-yl)methyl]cyclohexanecarboxylic acid methyl trans-4-[(6-{[4-(difluoromethyl)pyridin-2-yl]amino}-4-methyl-2,3'-bipyridin-6'-yl)-1-hydroxyethyl]cyclohexanecarboxylate Another subset of the representative compounds of the present invention are as follows, where each named compound is intended to encompass its individual isomers, mixtures thereof (including racemates and diastereomeric mixtures), as well as pharmaceutically acceptable salts thereof:

ethyl trans-4-[1-(6-{[4-(difluoromethyl)pyridin-2-yl]amino}-4-methyl-2,3'-bipyridin-6'-yl)-1-hydroxyethyl]cyclohexanecarboxylate;

2-hydroxyethyl trans-4-[1-(6-{[4-(difluoromethyl)pyridin-2-yl]amino}-4-methyl-2,3'-bipyridin-6'-yl)-1-hydroxyethyl]cyclohexanecarboxylate;

benzyl trans-4-[1-(6-{[4-(difluoromethyl)pyridin-2-yl]amino}-4-methyl-2,3'-bipyridin-6'-yl)-1-hydroxyethyl]cyclohexanecarboxylate;

propyl trans-4-[1-(6-{[4-(difluoromethyl)pyridin-2-yl]amino}-4-methyl-2,3'-bipyridin-6'-yl)-1-hydroxyethyl]cyclohexanecarboxylate;

propan-2-yl trans-4-[1-(6-{[4-(difluoromethyl)pyridin-2-yl]amino}-4-methyl-2,3'-bipyridin-6'-yl)-1-hydroxyethyl]cyclohexanecarboxylate;

butyl trans-4-[1-(6-{[4-(difluoromethyl)pyridin-2-yl]amino}-4-methyl-2,3'-bipyridin-6'-yl)-1-hydroxyethyl]cyclohexanecarboxylate;

butan-2-yl trans-4-[1-(6-{[4-(difluoromethyl)pyridin-2-yl]amino}-4-methyl-2,3'-bipyridin-6'-yl)-1-hydroxyethyl]cyclohexanecarboxylate;

2-methylpropyl trans-4-[1-(6-{[4-(difluoromethyl)pyridin-2-yl]amino}-4-methyl-2,3'-bipyridin-6'-yl)-1-hydroxyethyl]cyclohexanecarboxylate;

pentyl trans-4-[1-(6-{[4-(difluoromethyl)pyridin-2-yl]amino}-4-methyl-2,3'-bipyridin-6'-yl)-1-hydroxyethyl]cyclohexanecarboxylate;

2,2-dimethylpropyl trans-4-[1-(6-{[4-(difluoromethyl)pyridin-2-yl]amino}-4-methyl-2,3'-bipyridin-6'-yl)-1-hydroxyethyl]cyclohexanecarboxylate;

hexyl trans-4-[1-(6-{[4-(difluoromethyl)pyridin-2-yl]amino}-4-methyl-2,3'-bipyridin-6'-yl)-1-hydroxyethyl]cyclohexanecarboxylate;

heptyl trans-4-[1-(6-{[4-(difluoromethyl)pyridin-2-yl]amino}-4-methyl-2,3'-bipyridin-6'-yl)-1-hydroxyethyl]cyclohexanecarboxylate;

octyl trans-4-[1-(6-{[4-(difluoromethyl)pyridin-2-yl]amino}-4-methyl-2,3'-bipyridin-6'-yl)-1-hydroxyethyl]cyclohexanecarboxylate;

cyclohexyl trans-4-[1-(6-{[4-(difluoromethyl)pyridin-2-yl]amino}-4-methyl-2,3'-bipyridin-6'-yl)-1-hydroxyethyl]cyclohexanecarboxylate;

tetrahydro-2H-pyran-4-yl trans-4-[1-(6-{[4-(difluoromethyl)pyridin-2-yl]amino}-4-methyl-2,3'-bipyridin-6'-yl)-1-hydroxyethyl]cyclohexanecarboxylate;

cyclohexylmethyl trans-4-[1-(6-{[4-(difluoromethyl)pyridin-2-yl]amino}-4-methyl-2,3'-bipyridin-6'-yl)-1-hydroxyethyl]cyclohexanecarboxylate;

2-methoxyethyl trans-4-[1-(6-{[4-(difluoromethyl)pyridin-2-yl]amino}-4-methyl-2,3'-bipyridin-6'-yl)-1-hydroxyethyl]cyclohexanecarboxylate;

2-(2-ethoxyethoxy)ethyl trans-4-[1-(6-{[4-(difluoromethyl)pyridin-2-yl]amino}-4-methyl-2,3'-bipyridin-6'-yl)-1-hydroxyethyl]cyclohexanecarboxylate;

2-methoxy-2-oxoethyl trans-4-[1-(6-{[4-(difluoromethyl)pyridin-2-yl]amino}-4-methyl-2,3'-bipyridin-6'-yl)-1-hydroxyethyl]cyclohexanecarboxylate;

2-(dimethylamino)-2-oxoethyl trans-4-[1-(6-{[4-(difluoromethyl)pyridin-2-yl]amino}-4-methyl-2,3'-bipyridin-6'-yl)-1-hydroxyethyl]cyclohexanecarboxylate;

2-(morpholin-4-yl)ethyl trans-4-[1-(6-{[4-(difluoromethyl)pyridin-2-yl]amino}-4-methyl-2,3'-bipyridin-6'-yl)-1-hydroxyethyl]cyclohexanecarboxylate;

2-(dimethylamino)ethyl trans-4-[1-(6-{[4-(difluoromethyl)pyridin-2-yl]amino}-4-methyl-2,3'-bipyridin-6'-yl)-1-hydroxyethyl]cyclohexanecarboxylate;

(5-methyl-2-oxo-1,3-dioxol-4-yl)methyl trans-4-[1-(6-{[4-(difluoromethyl)pyridin-2-yl]amino}-4-methyl-2,3'-bipyridin-6'-yl)-1-hydroxyethyl]cyclohexanecarboxylate;

[(ethoxycarbonyl)oxy]methyl trans-4-[1-(6-{[4-(difluoromethyl)pyridin-2-yl]amino}-4-methyl-2,3'-bipyridin-6'-yl)-1-hydroxyethyl]cyclohexanecarboxylate;

{[(propan-2-yloxy)carbonyl]oxy}methyl trans-4-[1-(6-{[4-(difluoromethyl)pyridin-2-yl]amino}-4-methyl-2,3'-bipyridin-6'-yl)-1-hydroxyethyl]cyclohexanecarboxylate;

1-[(ethoxycarbonyl)oxy]ethyl trans-4-[1-(6-{[4-(difluoromethyl)pyridin-2-yl]amino}-4-methyl-2,3'-bipyridin-6'-yl)-1-hydroxyethyl]cyclohexanecarboxylate;

1-{[(propan-2-yloxy)carbonyl]oxy}ethyl trans-4-[1-(6-{[4-(difluoromethyl)pyridin-2-yl]amino}-4-methyl-2,3'-bipyridin-6'-yl)-1-hydroxyethyl]cyclohexanecarboxylate;

1-{[(cyclohexyloxy)carbonyl]oxy}ethyl trans-4-[1-(6-{[4-(difluoromethyl)pyridin-2-yl]amino}-4-methyl-2,3'-bipyridin-6'-yl)-1-hydroxyethyl]cyclohexanecarboxylate;

(acetyloxy)methyl trans-4-[1-(6-{[4-(difluoromethyl)pyridin-2-yl]amino}-4-methyl-2,3'-bipyridin-6'-yl)-1-hydroxyethyl]cyclohexanecarboxylate;

[(2,2-dimethylpropanoyl)oxy]methyl trans-4-[1-(6-{[4-(difluoromethyl)pyridin-2-yl]amino}-4-methyl-2,3'-bipyridin-6'-yl)-1-hydroxyethyl]cyclohexanecarboxylate;

1-(acetyloxy)ethyl trans-4-[1-(6-{[4-(difluoromethyl)pyridin-2-yl]amino}-4-methyl-2,3'-bipyridin-6'-yl)-1-hydroxyethyl]cyclohexanecarboxylate;

1[(2-methylpropanoyl)oxy]ethyl trans-4-[1-(6-{[4-(difluoromethyl)pyridin-2-yl]amino}-4-methyl-2,3'-bipyridin-6'-yl)-1-hydroxyethyl]cyclohexanecarboxylate;

2-(acetyloxy)ethyl trans-4-[1-(6-{[4-(difluoromethyl)pyridin-2-yl]amino}-4-methyl-2,3'-bipyridin-6'-yl)-1-hydroxyethyl]cyclohexanecarboxylate;

methyl trans-4-[1-(6-{[4-(difluoromethyl)pyridin-2-yl]amino}-4-methyl-2,3'-bipyridin-6'-yl)-1-hydroxyethyl]cyclohexanecarboxylate; and 1-(6-{[4-(difluoromethyl)pyridin-2-yl]amino}-4-methyl-2,3'-bipyridin-6'-yl)-1-[trans-4-(hydroxymethyl)cyclohexyl]ethanol.

In the application various terms are as defined below unless specified otherwise:

"Alkyl" refers to a straight- or branched-chain hydrocarbon radical having the specified number of carbon atoms. Examples of "alkyl" include, but are not limited to, methyl, ethyl, n-propyl, isopropyl, n-butyl, isobutyl, t-butyl, n-pentyl, isopentyl, and the like.

"Aryl" refers to an aromatic monocyclic or multicyclic ring system comprising about 6 to about 14 carbon atoms, preferably about 6 to about 10 carbon atoms. Examples include phenyl and naphthyl.

"Carbocycle" refers to a non-aromatic saturated or partially unsaturated monocyclic ring in which all ring atoms are carbon, and the ring being isolated or fused (including ortho-fused, spiro-fused and bridged) to one or two such ring or to a benzene ring. In the case of a polycyclic carbocycle, the attachment point may be on any ring. Examples of carbocycles include, but are not limited to, cyclopropyl, cyclobutyl, cyclopentyl, cyclohexyl, cyclohexenyl, cycloheptyl, cycloheptenyl, bicyclo[3.3.0]octane, indane, bicyclo[3.3.1]nonane, decalin, tetrahydronaphthalene, spiro[3.3]heptane, and bicyclo[3.1.0]hexane.

"Cycloalkyl" refers to a saturated ring containing the specified number of ring carbon atoms, and no heteroatom. In a like manner the term "$C_{3-6}$ cycloalkyl" refers to a saturated ring ring having from 3 to 6 ring carbon atoms. Exemplary "cycloalkyl" groups useful in the present invention include, but are not limited to, cyclopropyl, cyclobutyl, cyclopentyl and cyclohexyl.

"Halogen" or "halo" refers to fluorine, chlorine, bromine, or iodine.

"Haloalkyl" refers to an alkyl group as defined above in which one and up to all hydrogen atoms are replaced by a halogen; halogen is as defined herein. Similarly "fluoroalkyl" refers to an alkyl group as defined above in which one and up to all hydrogen atoms are replaced by fluorine. Examples of such branched or straight chained haloalkyl groups useful in the present invention include, but are not limited to, methyl, ethyl, propyl, isopropyl, isobutyl and n-butyl substituted independently with one or more halos, e.g., fluoro, chloro, bromo and iodo. Examples of "haloalkyl" include, but are not limited to, fluoromethyl, difluoromethyl, trifluoromethyl, 1-fluoroethyl, 2fluoroethyl, 2,2-difluoroethyl, 2,2,2-trifluoroethyl, and perfluoro-n-propyl.

"Hydroxyalkyl" refers to an alkyl group as defined above in which one hydrogen on each carbon atom may be replaced by a hydroxy group. Examples of "hydroxyalkyl" include, but are not limited to, hydroxymethyl, hydroxyethyl, isopropanol, propane-1,2-diol.

"Heterocycle" or "heterocyclyl" refers to a non-aromatic saturated monocyclic or multicyclic ring system having 3 to 10 ring atoms, preferably 5 to 10 ring atoms, in which one or more of the atoms in the ring system is an element other than carbon, for example nitrogen, oxygen or sulfur, alone or in combination. There are no adjacent oxygen and/or sulfur atoms present in the ring system. Where the heterocycle contains a ring nitrogen, the heterocyclyl can be connected to the rest of the molecule via a ring carbon or nitrogen atom. The nitrogen or sulfur atom of the heterocyclyl can be optionally oxidized to the corresponding N-oxide, S-oxide or S,S-dioxide. Examples of heterocyclyl rings include, but are not limited to, azetidinyl, piperidyl, pyrrolidinyl, piperazinyl, morpholinyl, thiomorpholinyl, thiazolidinyl, 1,4-dioxanyl, tetrahydrofuranyl, tetrahydrothiophenyl, decahydroquinolinyl, and the like.

"Heteroaryl" means an aromatic monocyclic or multicyclic ring system having 5 to 14 ring atoms, preferably 5 to 10 ring atoms, in which one or more of the ring atoms is an element other than carbon, for example nitrogen, oxygen or sulfur, alone or in combination. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, pyrazolo[1,5-a]pyrimidinyl, imidazo[1,2-a]pyridinyl, imidazo[2,1-b]thiazolyl, indazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, naphthyridinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of formula I, and pharmaceutically acceptable excipients.

As used herein, the term "optionally" means that the subsequently described event(s) may or may not occur, and includes both event(s), which occur, and events that do not occur.

As used herein, the term "substituted with one or more groups" refers to substitution with the named substituent or substituents, multiple degrees of substitution, up to replacing all hydrogen atoms with the same or different substituents, being allowed unless the number of substituents is explicitly stated. Where the number of substituents is not explicitly stated, one or more is intended.

Each variable is independently defined each time it occurs within the generic structural formula definitions. For example, when there is more than one substituent on a "Z" ring, each substituent is independently selected at each occurrence, and each substituent can be the same or different from the other(s).

The notation "$(CH_2)_{0-1}$" means the methylene group is either present or absent.

The term "Syk inhibitor", is used to mean a compound which inhibits the Syk enzyme.

The term "Syk mediated disease" or a "disorder or disease or condition mediated by inappropriate Syk activity" is used to mean any disease state mediated or modulated by Syk kinase mechanisms. Such disease states may include inflammatory, allergic and autoimmune diseases, for example, asthma, chronic obstructive pulmonary disease (COPD), adult respiratory distress syndrome (ARDs), ulcerative colitis, Crohns disease, bronchitis, dermatitis, allergic rhinitis, psoriasis, scleroderma, urticaria, rheumatoid arthritis, multiple sclerosis, cancer, HIV and lupus, in particular, asthma, chronic obstructive pulmonary disease (COPD), adult respiratory distress syndrome (ARDs), allergic rhinitis and rheumatoid arthritis.

As used herein, "a compound of the invention" means a compound of formula I or a salt, solvate or physiologically functional derivative thereof.

As used herein, the term "solvate" refers to a complex of variable stoichiometry formed by a solute (in this invention, a compound of formula I, or a salt thereof) and a solvent. Such solvents for the purpose of the invention may not interfere with the biological activity of the solute. Examples of suitable solvents include, but are not limited to, water, acetone, methanol, ethanol and acetic acid. Preferably the solvent used is a pharmaceutically acceptable solvent. Examples of suitable pharmaceutically acceptable solvents include water, ethanol and acetic acid. Most preferably the solvent is water.

As used herein, the term "physiologically functional derivative" refers to a compound (e.g, a drug precursor) that is transformed in vivo to yield a compound of formula I or a pharmaceutically acceptable salt, hydrate or solvate of the compound. The transformation may occur by various mechanisms (e.g., by metabolic or chemical processes), such as, for example, through hydrolysis in blood. Prodrugs are such derivatives, and a discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

The compounds of formula I may have the ability to crystallize in more than one form, a characteristic known as polymorphism, and it is understood that such polymorphic forms ("polymorphs") are within the scope of formula I. Polymorphism generally can occur as a response to changes in temperature or pressure or both and can also result from variations in the crystallization process. Polymorphs can be distinguished by various physical characteristics known in the art such as x-ray diffraction patterns, solubility and melting point.

The compounds of formula I may contain asymmetric or chiral centers, and, therefore, exist in different stereoisomeric forms. It is intended that all stereoisomeric forms of the compounds of formula I as well as mixtures thereof, including racemic mixtures, form part of the present invention. Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Moshers acid chloride), separating the diastereomers and converting (e.g., hydrolyzing) the individual diastereomers to the corresponding pure enantiomers. Enantiomers can also be separated by chromatography employing columns with a chiral stationary phase. Also, some of the compounds of formula I may be atropisomers (e.g., substituted biaryls) and are considered as part of this invention.

It is also noted that the compounds of formula I may form tautomers. It is understood that all tautomers and mixtures of tautomers of the compounds of the present invention are included within the scope of the compounds of the present invention. Some of the compounds described herein contain olefinic double bonds, and unless specified otherwise, are meant to include both E and Z geometric isomers.

Whilst the embodiments for each variable have generally been listed above separately for each variable, this invention also includes those compounds in which several or each embodiment in formula I is selected from each of the embodiments listed above. Therefore, this invention is intended to include all combinations of embodiments for each variable.

The compounds of the present invention may be in the form of and/or may be administered as a pharmaceutically acceptable salt. For a review on suitable salts see Berge et al, J. Pharm. Sci. 1977, 66, 1-19. Typically, the salts of the present invention are pharmaceutically acceptable salts. Salts encompassed within the term "pharmaceutically acceptable salts" refer to non-toxic salts of the compounds of this invention. Suitable pharmaceutically acceptable salts can include acid or base additions salts.

A pharmaceutically acceptable acid addition salt can be formed by reaction of a compound of formula I with a suitable inorganic or organic acid (such as hydrobromic, hydrochloric, sulfuric, nitric, phosphoric, succinic, maleic, formic, acetic, propionic, fumaric, citric, tartaric, lactic, benzoic, salicylic, glutamic, aspartic, p-toluenesulfonic, benzenesulfonic, methanesulfonic, ethanesulfonic, naphthalenesulfonic such as 2-naphthalenesulfonic, or hexanoic acid), optionally in a suitable solvent such as an organic solvent, to give the salt which is usually isolated, for example, by crystallisation and filtration. A pharmaceutically acceptable acid addition salt of a compound of formula I can comprise or be, for example, a hydrobromide, hydrochloride, sulfate, nitrate, phosphate, succinate, maleate, formarate, acetate, propionate, fumarate, citrate, tartrate, lactate, benzoate, salicylate, glutamate, aspartate, p-toluenesulfonate, benzenesulfonate, methanesulfonate, ethanesulfonate, naphthalenesulfonate (e.g., 2-naphthalenesulfonate) or hexanoate salt.

A pharmaceutically acceptable base salt can be formed by reaction of a compound of formula I with a suitable inorganic or organic base. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

Other, non-pharmaceutically acceptable, salts, e.g., oxalates or trifluoroacetates, may also be used, for example, in the isolation of compounds of the invention, and are included within the scope of this invention.

The invention includes within its scope all possible stoichiometric and non-stoichiometric forms of the compounds of formula I.

In the compounds of formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic formula I can be prepared without undue experimentation by conventional techniques well known to those skilled in the art or by processes analogous to those described in the Schemes and Examples herein using appropriate isotopically-enriched reagents and/or intermediates The compounds of formula I and salts, solvates and physiologically functional derivatives thereof are believed to be inhibitors of Syk activity, and thus be potentially useful in the treatment of diseases and conditions associated with inappropriate Syk activity.

In certain embodiments, the compounds of formula I are prodrugs of inhibitors of Syk activity, and thus are potentially useful in the treatment of diseases and conditions associated with inappropriate Syk activity.

Compound of formula I or its pharmaceutically acceptable salts and pharmaceutical compositions can be used to treat or prevent a variety of conditions or diseases mediated by Spleen tyrosine kinase (Syk). Such conditions and diseases include, but are not limited to: (1) arthritis, including rheumatoid arthritis, juvenile arthritis, psoriatic arthritis and osteoarthritis; (2) asthma and other obstructive airways diseases, including chronic asthma, late asthma, airway hyper-responsiveness, bronchitis, bronchial asthma, allergic asthma, intrinsic asthma, extrinsic asthma, dust asthma, adult respiratory distress syndrome, recurrent airway obstruction, and chronic obstruction pulmonary disease including emphysema; (3) autoimmune diseases or disorders, including those designated as single organ or single cell-type autoimmune disorders, for example Hashimotos thyroiditis, autoimmune hemolytic anemia, autoimmune atrophic gastritis of pernicious anemia, autoimmune encephalomyelitis, autoimmune orchitis, Goodpastures disease, autoimmune thrombocytopenia including idiopathic thrombopenic purpura, sympathetic ophthalmia, myasthenia gravis, Graves' disease, primary biliary cirrhosis, chronic aggressive hepatitis, ulcerative colitis and membranous glomerulopathy, those designated as involving systemic autoimmune disorder, for example systemic lupus erythematosis, immune thrombocytopenic purpura, rheumatoid arthritis, Sjogrens syndrome, Reiters syndrome, polymyositis-dermatomyositis, systemic sclerosis, polyarteritis nodosa, multiple sclerosis and bullous pemphigoid, and additional autoimmune diseases, which can be B-cell (humoral) based or T-cell based, including Cogans syndrome, ankylosing spondylitis, Wegeners granulomatosis, autoimmune alopecia, Type I or juvenile onset diabetes, and thyroiditis; (4) cancers or tumors, including alimentary/gastrointestinal tract cancer, colon cancer, liver cancer, skin cancer including mast cell tumor and squamous cell carcinoma, breast and mammary cancer, ovarian cancer, prostate cancer, lymphoma and leukemia (including but not limited to acute myelogenous leukemia, chronic myelogenous leukemia, mantle cell lymphoma, NHL B cell lymphomas (e.g., precursor B-ALL, marginal zone B cell lymphoma, chronic lymphocytic leukemia, diffuse large B cell lymphoma, Burkitt lymphoma, mediastinal large B-cell lymphoma), Hodgkin lymphoma, NK and T cell lymphomas; TEL-Syk and ITK-Syk fusion driven tumors) myelomas including multiple myeloma, myeloproliferative disorders kidney cancer, lung cancer, muscle cancer, bone cancer, bladder cancer, brain cancer, melanoma including oral and metastatic melanoma, Kaposis sarcoma, proliferative diabetic retinopathy, and angiogenic-associated disorders including solid tumors, and pancreatic cancer; (5) diabetes, including Type I diabetes and complications from diabetes; (6) eye diseases, disorders or conditions including autoimmune diseases of the eye, keratoconjunctivitis, vernal conjunctivitis, uveitis including uveitis associated with Behcets disease and lens-induced uveitis, keratitis, herpetic keratitis, conical keratitis, corneal epithelial dystrophy, keratoleukoma, ocular premphigus, Moorens ulcer, scleritis, Graves ophthalmopathy, Vogt-Koyanagi-Harada syndrome, keratoconjunctivitis sicca (dry eye), phlyctenule, iridocyclitis, sarcoidosis, endocrine ophthalmopathy, sympathetic ophthalmitis, allergic conjunctivitis, and ocular neovascularization; (7) intestinal inflammations, allergies or conditions including Crohns disease and/or ulcerative colitis, inflammatory bowel disease, coeliac diseases, proctitis, eosinophilic gastroenteritis, and mastocytosis; (8) neurodegenerative diseases including motor neuron disease, Alzheimers disease, Parkinsons disease, amyotrophic lateral sclerosis, Huntingtons disease, cerebral ischemia, or neurodegenerative disease caused by traumatic injury, strike, glutamate neurotoxicity or hypoxia; ischemicreperfusion injury in stroke, myocardial ischemica, renal ischemia, heart attacks, cardiac hypertrophy, atherosclerosis and arteriosclerosis, organ hypoxia; (9) platelet aggregation and diseases associated with or caused by platelet activation, such as arteriosclerosis, thrombosis, intimal hyperplasia and restenosis following vascular injury; (10) conditions associated with cardiovascular diseases, including restenosis, acute coronary syndrome, myocardial infarction, unstable angina, refractory angina, occlusive coronary thrombus occurring post-thrombolytic therapy or post-coronary angioplasty, a thrombotically mediated cerebrovascular syndrome, embolic stroke, thrombotic stroke, transient ischemic attacks, venous thrombosis, deep venous thrombosis, pulmonary embolus, coagulopathy, disseminated intravascular coagulation, thrombotic thrombocytopenic purpura, thromboangiitis obliterans, thrombotic disease associated with heparin-induced thrombocytopenia, thrombotic complications associated with extracorporeal circulation, thrombotic complications associated with instrumentation such as cardiac or other intravascular catheterization, intra-aortic balloon pump, coronary stent or cardiac valve, conditions requiring the fitting of prosthetic devices, and the like; (11) skin diseases, conditions or disorders including atopic dermatitis, eczema, psoriasis, scleroderma, pruritus and other pruritic conditions; (12) allergic reactions including anaphylaxis, allergic rhinitis, allergic dermatitis, allergic urticaria, angioedema, allergic asthma, or allergic reaction to insect bites, food, drugs, or pollen; (13) transplant rejection, including pancreas islet transplant rejection, bone marrow transplant rejection, graft-versus-host disease, organ and cell transplant rejection such as bone marrow, cartilage, cornea, heart, intervertebral disc, islet, kidney, limb, liver, lung, muscle, myoblast, nerve, pancreas, skin, small intestine, or trachea, and xeno transplantation; (14) low grade scarring including scleroderma, increased fibrosis, keloids, post-surgical scars, pulmonary fibrosis, vascular spasms, migraine, reperfusion injury, and post-myocardial infarction.

The invention thus provides compounds of formula I and salts, solvates and physiologically functional derivatives thereof for use in therapy, and particularly in the treatment of diseases and conditions mediated by inappropriate Syk activity. The inappropriate Syk activity referred to herein is any Syk activity that deviates from the normal Syk activity expected in a particular mammalian subject. Inappropriate Syk activity may take the form of, for instance, an abnormal increase in activity, or an aberration in the timing and or control of Syk activity. Such inappropriate activity may result then, for example, from overexpression or mutation of the protein kinase leading to inappropriate or uncontrolled activation.

In a further embodiment, the present invention is directed to methods of regulating, modulating, or inhibiting Syk for the prevention and/or treatment of disorders related to unregulated Syk activity.

In a further embodiment, the present invention provides a method of treatment of a mammal suffering from a disorder mediated by Syk activity, which comprises administering to said mammal an effective amount of a compound of formula I or a pharmaceutically acceptable salt, solvate, or a physiologically functional derivative thereof.

In a further embodiment, the present invention provides for the use of a compound of formula I, or a pharmaceutically acceptable salt or solvate thereof, or a physiologically functional derivative thereof, in the preparation of a medicament for the treatment of a disorder mediated by Syk activity.

In a further embodiment said disorder mediated by Syk activity is asthma. In a further embodiment said disorder is rheumatoid arthritis. In yet another embodiment, said disorder is cancer. In a further embodiment said disorder is ocular conjunctivitis.

Yet another aspect of the present invention provides a method for treating diseases caused by or associated with Fc receptor signaling cascades, including FceRI and/or FcgRI-mediated degranulation as a therapeutic approach towards the treatment or prevention of diseases characterized by, caused by and/or associated with the release or synthesis of chemical mediators of such Fc receptor signaling cascades or degranulation. In addition, Syk is known to play a critical role in immunotyrosine-based activation motif (ITAM) singaling, B cell receptor signaling, T cell receptor singaling and is an essential component of integrin beta (1), beta (2), and beta (3) signaling in neutrophils. Thus, compounds of the present invention can be used to regulate Fc receptor, ITAM, B cell receptor and integrin singaling cascades, as well as the cellular responses elicited through these signaling cascades. Non-limiting examples of cellular responses that may be regulated or inhibited include respiratory burst, cellular adhesion, cellular degranulation, cell spreading, cell migration, phagocytosis, calcium ion flux, platelet aggregation and cell maturation.

While it is possible that, for use in therapy, a compound of formula I, as well as salts, solvates and physiological functional derivatives thereof, may be administered as the raw chemical, it is possible to present the active ingredient as a pharmaceutical composition. Accordingly, the invention further provides a pharmaceutical composition, which comprises a compound of formula I and salts, solvates and physiological functional derivatives thereof, and one or more pharmaceutically acceptable carriers, diluents, or excipients. The compounds of the formula I and salts, solvates and physiological functional derivatives thereof, are as described above. The carrier(s), diluent(s) or excipient(s) must be acceptable in the sense of being compatible with the other ingredients of the formulation and not deleterious to the recipient thereof. In accordance with another aspect of the invention there is also provided a process for the preparation of a pharmaceutical composition including admixing a compound of the formula I, or salts, solvates and physiological functional derivatives thereof, with one or more pharmaceutically acceptable carriers, diluents or excipients.

Pharmaceutical compositions of the present invention may be presented in unit dose forms containing a predetermined amount of active ingredient per unit dose. Such a unit may contain, for example, 5 µg to 1 g, preferably 1 mg to 700 mg, more preferably 5 mg to 100 mg of a compound of the formula I, depending on the condition being treated, the route of administration and the age, weight and condition of the patient. Such unit doses may therefore be administered more than once a day. Preferred unit dosage compositions are those containing a daily dose or sub-dose (for administration more than once a day), as herein above recited, or an appropriate fraction thereof, of an active ingredient. Furthermore, such pharmaceutical compositions may be prepared by any of the methods well known in the pharmacy art.

Pharmaceutical compositions of the present invention may be adapted for administration by any appropriate route, for example by the oral (including buccal or sublingual), rectal, topical, inhaled, nasal, ocular, or parenteral (including intravenous and intramuscular) route. Such compositions may be prepared by any method known in the art of pharmacy, for example by bringing into association the active ingredient with the carrier(s) or excipient(s). Dosage forms include tablets, troches, dispersions, suspensions, solutions, capsules, creams, ointments, aerosols, and the like.

In a further embodiment, the present invention provides a pharmaceutical composition adapted for administration by the oral route, for treating, for example, rheumatoid arthritis.

In a further embodiment, the present invention provides a pharmaceutical composition adapted for administration by the nasal route, for treating, for example, allergic rhinitis.

In a further embodiment, the present invention provides a pharmaceutical composition adapted for administration by the inhaled route, for treating, for example, asthma, COPD or ARDS.

In a further embodiment, the present invention provides a pharmaceutical composition adapted for administration by the ocular route, for treating, diseases of the eye, for example, conjunctivitis.

In a further embodiment, the present invention provides a pharmaceutical composition adapted for administration by the parenteral (including intravenous) route, for treating, for example, cancer.

Pharmaceutical compositions of the present invention which are adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit compositions for oral administration can be microencapsulated. The formulation can also be prepared to prolong or sustain the release, for example, by coating or embedding particulate material in polymers, wax or the like.

The compounds of formula I, and salts, solvates and physiological functional derivatives thereof, can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of formula I and salts, solvates and physiological functional derivatives thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Dosage forms for inhaled administration may conveniently be formulated as aerosols or dry powders.

For compositions suitable and/or adapted for inhaled administration, it is preferred that the compound or salt of formula I is in a particle-size-reduced form, and more preferably the size-reduced form is obtained or obtainable by micronisation. The preferable particle size of the size-reduced (e.g., micronised) compound or salt or solvate is defined by a D50 value of about 0.5 to about 10 microns (for example as measured using laser diffraction).

Aerosol formulations, e.g., for inhaled administration, can comprise a solution or fine suspension of the active substance in a pharmaceutically acceptable aqueous or non-aqueous solvent. Aerosol formulations can be presented in single or multidose quantities in sterile form in a sealed container, which can take the form of a cartridge or refill for use with an atomising device or inhaler. Alternatively the sealed container may be a unitary dispensing device such as a single dose nasal inhaler or an aerosol dispenser fitted with a metering valve (metered dose inhaler) which is intended for disposal once the contents of the container have been exhausted.

Where the dosage form comprises an aerosol dispenser, it preferably contains a suitable propellant under pressure such as compressed air, carbon dioxide or an organic propellant such as a hydrofluorocarbon (HFC). Suitable HFC propellants include 1,1,1,2,3,3,3-heptafluoropropane and 1,1,1,2-tetrafluoroethane. The aerosol dosage forms can also take the form of a pump-atomiser. The pressurised aerosol may contain a solution or a suspension of the active compound. This may require the incorporation of additional excipients e.g., co-solvents and/or surfactants to improve the dispersion characteristics and homogeneity of suspension formulations. Solution formulations may also require the addition of co-solvents such as ethanol. Other excipient modifiers may also be incorporated to improve, for example, the stability and/or taste and/or fine particle mass characteristics (amount and/or profile) of the formulation.

For pharmaceutical compositions suitable and/or adapted for inhaled administration, it is preferred that the pharmaceutical composition is a dry powder inhalable composition. Such a composition can comprise a powder base such as lactose, glucose, trehalose, mannitol or starch, the compound of formula I or salt or solvate thereof (preferably in particle-size-reduced form, e.g., in micronised form), and optionally a performance modifier such as L-leucine or another amino acid, and/or metals salts of stearic acid such as magnesium or calcium stearate. Preferably, the dry powder inhalable composition comprises a dry powder blend of lactose and the compound of formula I or salt thereof. The lactose is preferably lactose hydrate e.g., lactose monohydrate and/or is preferably inhalation-grade and/or fine-grade lactose. Preferably, the particle size of the lactose is defined by 90% or more (by weight or by volume) of the lactose particles being less than 1000 microns (micrometers) (e.g., 10-1000 microns e.g., 30-1000 microns) in diameter, and/or 50% or more of the lactose particles being less than 500 microns (e.g., 10-500 microns) in diameter. More preferably, the particle size of the lactose is defined by 90% or more of the lactose particles being less than 300 microns (e.g., 10-300 microns e.g., 50-300 microns) in diameter, and/or 50% or more of the lactose particles being less than 100 microns in diameter. Optionally, the particle size of the lactose is defined by 90% or more of the lactose particles being less than 100-200 microns in diameter, and/or 50% or more of the lactose particles being less than 40-70 microns in diameter. It is preferable that about 3 to about 30% (e.g., about 10%) (by weight or by volume) of the particles are less than 50 microns or less than 20 microns in diameter. For example, without limitation, a suitable inhalation-grade lactose is E9334 lactose (10% fines) (Borculo Domo Ingredients, Hanzeplein 25, 8017 J D Zwolle, Netherlands).

Optionally, in particular for dry powder inhalable compositions, a pharmaceutical composition for inhaled administration can be incorporated into a plurality of sealed dose containers (e.g., containing the dry powder composition) mounted longitudinally in a strip or ribbon inside a suitable inhalation device. The container is rupturable or peel-openable on demand and the dose of e.g., the dry powder composition can be administered by inhalation via the device such as the DISKUS® device (GlaxoSmithKline). Other dry powder inhalers are well known to those of ordinary skill in the art, and many such devices are commercially available, with representative devices including Aerolizer® (Novartis), Airmax™ (IVAX), ClickHaler® (Innovata Biomed), Diskhaler® (GlaxoSmithKline), Accuhaler (GlaxoSmithKline), Easyhaler®(Orion Pharma), Eclipse™ (Aventis), Flow-Caps® (Hovione), Handihaler® (Boehringer Ingelheim), Pulvinal® (Chiesi), Rotahaler® (GlaxoSmithKline), Skye-Haler™ or Certihaler™ (SkyePharma), Twisthaler® (Schering-Plough), Turbuhaler® (AstraZeneca), Ultrahaler® (Aventis), and the like.

Dosage forms for ocular administration may be formulated as solutions or suspensions with excipients suitable for ophthalmic use.

Dosage forms for nasal administration may conveniently be formulated as aerosols, solutions, drops, gels or dry powders.

Pharmaceutical compositions adapted for administration by inhalation include fine particle dusts or mists, which may be generated by means of various types of metered, dose pressurised aerosols, nebulizers or insufflators.

For pharmaceutical compositions suitable and/or adapted for intranasal administration, the compound of formula I or a pharmaceutically acceptable salt or solvate thereof may be formulated as a fluid formulation for delivery from a fluid dispenser. Such fluid dispensers may have, for example, a dispensing nozzle or dispensing orifice through which a metered dose of the fluid formulation is dispensed upon the application of a user-applied force to a pump mechanism of the fluid dispenser. Such fluid dispensers are generally provided with a reservoir of multiple metered doses of the fluid formulation, the doses being dispensable upon sequential pump actuations. The dispensing nozzle or orifice may be configured for insertion into the nostrils of the user for spray dispensing of the fluid formulation into the nasal cavity. A fluid dispenser of the aforementioned type is described and illustrated in WO-A-2005044354, the entire content of which is hereby incorporated herein by reference. The dispenser has a housing which houses a fluid discharge device having a compression pump mounted on a container for containing a fluid formulation. The housing has at least one finger-operable side lever which is movable inwardly with respect to the housing to cam the container upwardly in the housing to cause the pump to compress and pump a metered dose of the formulation out of a pump stem through a nasal nozzle of the housing. A particularly preferred fluid dispenser is of the general type illustrated in FIGS. 30-40 of WO-A-2005044354.

The following are examples of representative pharmaceutical dosage forms for the compounds of this invention:

| Injectable Suspension (I.M.) | mg/ml |
| --- | --- |
| Compound of Formula I | 10 |
| Methylcellulose | 5.0 |
| Tween 80 | 0.5 |
| Benzyl alcohol | 9.0 |
| Benzalkonium chloride | 1.0 |
| Water for injection to a total volume of 1 ml | |

| Tablet | mg/tablet |
| --- | --- |
| Compound of Formula I | 25 |
| Microcrystalline Cellulose | 415 |
| Providone | 14.0 |
| Pregelatinized Starch | 43.5 |
| Magnesium Stearate | 2.5 |
| | 500 |

| Capsule | mg/capsule |
| --- | --- |
| Compound of Formula I | 25 |
| Lactose Powder | 573.5 |
| Magnesium Stearate | 1.5 |
| | 600 |

| Inhalation Aerosol | Per dose |
| --- | --- |
| Compound of Formula I | 100 mcg |
| Oleic Acid | 5 mcg |
| Ethanol | 1 mg |
| HFA 227 (1,1,1,2,3,3,3-heptafluoropropane) | 75 mg |

| Dry Powder Inhalation Aerosol | Per dose |
| --- | --- |
| Compound of Formula I | 100 mcg |
| Lactose | 12.5 mg |

It will be appreciated that when the compound of the present invention is administered in combination with other therapeutic agents normally administered by the inhaled, intravenous, oral or intranasal route, that the resultant pharmaceutical composition may be administered by the same routes.

It should be understood that in addition to the ingredients particularly mentioned above, the compositions may include other agents conventional in the art having regard to the type of formulation in question, for example those suitable for oral administration may include flavouring agents.

A therapeutically effective amount of a compound of the present invention will depend upon a number of factors including, for example, the age and weight of the animal, the precise condition requiring treatment and its severity, the nature of the formulation, and the route of administration, and will ultimately be at the discretion of the attendant physician or veterinarian However, an effective amount of a compound of formula I for the treatment of diseases or conditions associated with inappropriate Syk activity, will generally be in the range of 5 μg to 100 mg/kg body weight of recipient (mammal) per day and more usually in the range of 5 μg to 10 mg/kg body weight per day. This amount may be given in a single dose per day or more usually in a number (such as two, three, four, five or six) of sub-doses per day such that the total daily dose is the same. An effective amount of a salt or solvate, thereof, may be determined as a proportion of the effective amount of the compound of formula I per se.

Compounds of the present invention, and their salts and solvates, and physiologically functional derivatives thereof, may be employed alone or in combination with other therapeutic agents for the treatment of diseases and conditions associated with inappropriate Syk activity. Combination therapies according to the present invention thus comprise the administration of at least one compound of formula I or a pharmaceutically acceptable salt or solvate thereof, or a physiologically functional derivative thereof, and the use of at least one other pharmaceutically active agent. The compound(s) of formula I and the other pharmaceutically active agent(s) may be administered together or separately and, when administered separately this may occur simultaneously or sequentially in any order. The amounts of the compound(s) of formula I and the other pharmaceutically active agent(s) and the relative timings of administration will be selected in order to achieve the desired combined therapeutic effect.

For the treatment of the inflammatory diseases, rheumatoid arthritis, psoriasis, inflammatory bowel disease, COPD, asthma and allergic rhinitis a compound of formula I may be combined with one or more other active agents such as: (1) TNF-α inhibitors such as infliximab (Remicade®), etanercept (Enbrel®), adalimumab (Humira®), certolizumab pegol (Cimzia®), and golimumab (Simponi®); (2) non-selective COX-I/COX-2 inhibitors (such as piroxicam, diclofenac, propionic acids such as naproxen, flubiprofen, fenoprofen, ketoprofen and ibuprofen, fenamates such as mefenamic acid, indomethacin, sulindac, etodolac, azapropazone, pyrazolones such as phenylbutazone, salicylates such as aspirin); (3) COX-2 inhibitors (such as meloxicam, celecoxib, rofecoxib, valdecoxib and etoricoxib); (4) other agents for treatment of rheumatoid arthritis including methotrexate, leflunomide, sulfasalazine, azathioprine, cyclosporin, tacrolimus, penicillamine, bucillamine, actarit, mizoribine, lobenzarit, ciclesonide, hydroxychloroquine, d-penicillamine, aurothiomalate, auranofin or parenteral or oral gold, cyclophosphamide, Lymphostat-B, BAFF/APRIL inhibitors and CTLA-4-Ig or mimetics thereof; (5) leukotriene biosynthesis inhibitor, 5-lipoxygenase (5-LO) inhibitor or 5-lipoxygenase activating protein (FLAP) antagonist such as zileuton; (6) LTD4 receptor antagonist such as zafirlukast, montelukast and pranlukast; (7) PDE4 inhibitor such as roflumilast, cilomilast, AWD-12-281 (Elbion), and PD-168787 (Pfizer); (8) antihistaminic H1 receptor antagonists such as cetirizine, levocetirizine, loratadine, desloratadine, fexofenadine, astemizole, azelastine, levocabastine, olopatidine, methapyrilene and chlorpheniramine; (9) α1- and α2-adrenoceptor agonist vasoconstrictor sympathomimetic agent, such as propylhexedrine, phenylephrine, phenylpropanolamine, pseudoephedrine, naphazoline hydrochloride, oxymetazoline hydrochloride, tetrahydrozoline hydrochloride, xylometazoline hydrochloride, and ethylnorepinephrine hydrochloride; (10) anticholinergic agents such as ipratropium bromide, tiotropium bromide, oxitropitun bromide, aclindinium bromide, glycopyrrolate, (R,R)-glycopyrrolate, pirenzepine, and telenzepine; (11) β-adrenoceptor agonists such as metaproterenol, isoproterenol, isoprenaline, albuterol, formoterol (particularly the fumarate salt), salmeterol (particularly the xinafoate salt), terbutaline, orciprenaline, bitolterol mesylate, fenoterol, and pirbuterol, or methylxanthanines including theophylline and aminophylline, sodium cromoglycate; (12) insulin-like growth factor type I (IGF-1) mimetic; (13) glucocorticosteroids, especially inhaled glucocorticoid with reduced systemic side effects, such as prednisone, prednisolone, flunisolide, triamcinolone acetonide, beclomethasone dipropionate, budesonide, fluticasone propionate, ciclesonide and mometasone furoate; (14) kinase inhibitors such as inhibitors of the Janus Kinases (JAK 1 and/or JAK2 and/or JAK 3 and/or TYK2) such as tofacitinib (Pfizer), baricitinib (Incyte), VX-509 (Vertex), ASP-015K (Astellas), GLPG0634 (Galapagos), SB-1578 (SBIO), and AC-430 (Ambit Biosciences); p38 MAPK and IKK2; (15) B-cell targeting biologics such as rituximab (Rituxan®); (16) selective costimulation modulators such as abatacept (Orencia); (17) interleukin inhibitors, such as IL-1 inhibitor anakinra (Kineret) and IL-6 inhibitor tocilizumab (Actemra).

The present invention also provides for so-called "triple combination" therapy, comprising a compound of formula I or a pharmaceutically acceptable salt thereof together with beta$_2$-adrenoreceptor agonist and an anti-inflammatory corticosteroid. Preferably this combination is for treatment and/or prophylaxis of asthma, COPD or allergic rhinitis. The beta$_2$-adrenoreceptor agonist and/or the anti-inflammatory corticosteroid can be as described above and/or as described in WO 03030939 A1. Representative examples of such a "triple" combination are a compound of formula I or a pharmaceutically acceptable salt thereof in combination with the components of Advair® (salmeterol xinafoate and fluticasone propionate), Symbicort® (budesonide and formoterol fumarate), or Dulera® (mometasone furoate and formoterol fumarate) or a pharmaceutically acceptable salt thereof (e.g., salmeterol xinafoate and fluticasone propionate).

For the treatment of cancer a compound of formula I may be combined with one or more of an anticancer agent. Examples of such agents can be found in *Cancer Principles and Practice of Oncology* by V. T. Devita and S. Hellman (editors), 6th edition (Feb. 15, 2001), Lippincott Williams & Wilkins Publishers. A person of ordinary skill in the art would be able to discern which combinations of agents would be useful based on the particular characteristics of the drugs and the cancer involved. Such anti-cancer agents include, but are not limited to, the following: (1) estrogen receptor modulator such as diethylstibestral, tamoxifen, raloxifene, idoxifene, LY353381, LY117081, toremifene, fluoxymestero, and SH646; (2) other hormonal agents including aromatase inhibitors (e.g., aminoglutethimide, tetrazole anastrozole, letrozole and exemestane), luteinizing hormone release hormone (LHRH) analogues, ketoconazole, goserelin acetate, leuprolide, megestrol acetate and mifepristone; (3) androgen receptor modulator such as finasteride and other 5α-reductase inhibitors, nilutamide, flutamide, bicalutamide, liarozole, and abiraterone acetate; (4) retinoid receptor modulator such as bexarotene, tretinoin, 13-cis-retinoic acid, 9-cis-retinoic acid, α-difluoromethylornithine, ILX23-7553, trans-N-(4'-hydroxyphenyl)retinamide, and N-4-carboxyphenyl retinamide; (5) antiproliferative agent such as antisense RNA and DNA oligonucleotides such as G3139, ODN698, RVASKRAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, aminopterin, 5-fluorouracil, floxuridine, methotrexate, leucovarin, hydroxyurea, thioguanine (6-TG), mercaptopurine (6-MP), cytarabine, pentostatin, fludarabine phosphate, cladribine (2-CDA), asparaginase, gemcitabine, alanosine, swainsonine, lometrexol, dexrazoxane, methioninase, and 3-aminopyridine-2-carboxaldehyde thiosemicabazone; (6) prenyl-protein transferase inhibitor including farnesyl-protein transferase (FPTase), geranylgeranyl-protein transferase type I (GGPTase-I), and geranylgeranyl-protein transferase type-II (GGPTase-II, also called Rab GGPTase); (7) HMG-CoA reductase inhibitor such as lovastatin, simvastatin, pravastatin, atorvastatin, fluvastatin and rosuvastatin; (8) angiogenesis inhibitor such as inhibitors of the tyrosine kinase receptors Flt-1 (VEGFR1) and Flk-1 KDR (VEGFR2), inhibitors of epidermal-derived, fibroblast-derived, or platelet derived growth factors, MMP (matrix metalloprotease) inhibitors, integrin blockers, interferon-α, interleukin-12, erythropoietin (epoietin-α), granulocyte-CSF (filgrastin), granulocyte, macrophage-CSF (sargramostim), pentosan polysulfate, cyclooxygenase inhibitors, steroidal anti-inflammatories, carboxyamidotriazole, combretastatin A-4, squalamine, 6-O-chloroacetyl-carbonyl)-fumagillol, thalidomide, angiostatin, troponin-1, angiotensin II antagonists, heparin, carboxypeptidase U inhibitors, and antibodies to VEGF, endostatin, ukrain, ranpirnase, IM862, acetyldinanaline, 5-amino-1-[[3,5-dichloro-4-(4-chlorobenzoyl) phenyl]methyl]-1H-1,2,3-triazole-4-carboxamide, CM101, squalamine, combretastatin, RPI4610, NX31838, sulfated mannopentaose phosphate, and 3-[(2,4-dimethylpyrrol-5-yl) methylene]-2-indolinone (SU5416); (9) PPAR-γ agonists, PPAR-δ agonists, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, GI262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and (2R)-7-(3-(2-chloro-4-(4-fluorophenoxy)phenoxy)propoxy)-2-ethylchromane-2-carboxylic acid (disclosed in U.S. Ser. Nos. 60/235, 708 and 60/244,697); (9) inhibitor of inherent multidrug resistance including inhibitors of p-glycoprotein (P-gp), such as LY335979, XR9576, OC144-093, R101922, VX853 and PSC833 (valspodar); (10) inhibitor of cell proliferation and survival signaling such as inhibitors of EGFR (for example gefitinib and erlotinib), inhibitors of ERB-2 (for example trastuzumab), inhibitors of IGF1R such as MK-0646 (dalotuzumab), inhibitors of CD20 (rituximab), inhibitors of cytokine receptors, inhibitors of MET, inhibitors of PI3K family kinase (for example LY294002), serine/threonine kinases (including but not limited to inhibitors of Akt such as described in (WO 03/086404, WO 03/086403, WO 03/086394, WO 03/086279, WO 02/083675, WO 02/083139, WO 02/083140 and WO 02/083138), inhibitors of Raf kinase (for example BAY-43-9006), inhibitors of MEK (for example CI-1040 and PD-098059) and inhibitors of mTOR (for example Wyeth CCI-779 and Ariad AP23573); (11) a bisphosphonate such as etidronate, pamidronate, alendronate, risedronate, zoledronate, ibandronate, incadronate or cimadronate, clodronate, EB-1053, minodronate, neridronate, piridronate and tiludronate; (12) γ-secretase inhibitors, (13) agents that interfere with receptor tyrosine kinases (RTKs) including inhibitors of c-Kit, Eph, PDGF, Flt3 and c-Met; (14) agent that interferes with a cell cycle checkpoint including inhibitors of ATR, ATM, the Chk1 and Chk2 kinases and cdk and cdc kinase inhibitors and are specifically exemplified by 7-hydroxystaurosporin, flavopiridol, CYC202 (Cyclacel) and BMS-387032; (15) BTK inhibitors such as PCI32765, AVL-292 and AVL-101; (16) PARP inhibitors including iniparib, olaparib, AG014699, ABT888 and MK4827; (16) ERK inhibitors; (17) mTOR inhibitors such as sirolimus, ridaforolimus, temsirolimus, everolimus; (18) cytotoxiccytostatic agents.

"Cytotoxiccytostatic agents" refer to compounds which cause cell death or inhibit cell proliferation primarily by interfering directly with the cells functioning or inhibit or interfere with cell mytosis, including alkylating agents, tumor necrosis factors, intercalators, hypoxia activatable compounds, microtubule inhibitors/microtubule-stabilizing agents, inhibitors of mitotic kinesins, inhibitors of histone deacetylase, inhibitors of kinases involved in mitotic progression, antimetabolites; biological response modifiers; hormonal/anti-hormonal therapeutic agents, haematopoietic growth factors, monoclonal antibody targeted therapeutic agents, topoisomerase inhibitors, proteasome inhibitors and ubiquitin ligase inhibitors.

Examples of cytotoxic agents include, but are not limited to, sertenef, cachectin, chlorambucil, cyclophosphamide, ifosfamide, mechlorethamine, melphalan, uracil mustard, thiotepa, busulfan, carmustine, lomustine, streptozocin, tasonermin, lonidamine, carboplatin, altretamine, dacarbazine, procarbazine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(II)]bis[diamine(chloro)platinum(II)]tetrachloride, diarizidinylspermine, arsenic trioxide, 1-(11-dodecylamino-10-hydroxyundecyl)-3,7-dimethylxanthine, zorubicin, doxorubicin, daunorubicin, idarubicin, anthracenedione, bleomycin, mitomycin C, dactinomycin, plicatomycin, bisantrene, mitoxantrone, pirarubicin, pinafide, valrubicin, amrubicin, antineoplaston, 3'-deamino-3'-morpholino-13-deoxo-10-hydroxycaminomycin, annamycin, galarubicin, elinafide, MEN10755, and 4-demethoxy-3-deamino-3-aziridinyl-4-methylsulphonyl-daunorubicin.

An example of a hypoxia activatable compound is tirapazamine.

Examples of proteasome inhibitors include but are not limited to lactacystin and bortezomib.

Examples of microtubule inhibitors/microtubule-stabilising agents include vincristine, vinblastine, vindesine, vinzolidine, vinorelbine, vindesine sulfate, 3',4'-didehydro-4'-deoxy-8'-norvincaleukoblastine, podophyllotoxins (e.g., etoposide (VP-16) and teniposide (VM-26)), paclitaxel, docetaxol, rhizoxin, dolastatin, mivobulin isethionate, auristatin, cemadotin, RPR109881, BMS184476, vinflunine, cryptophycin, anhydrovinblastine, N,N-dimethyl-L-valyl-L-valyl-N-methyl-L-valyl-L-prolyl-L-proline-t-butylamide,
TDX258, the epothilones (see for example U.S. Pat. Nos. 6,284,781 and 6,288,237) and BMS188797.

Some examples of topoisomerase inhibitors are topotecan, hycaptamine, irinotecan, rubitecan, 6-ethoxypropionyl-3',4'-O-exo-benzylidene-chartreusin, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, 2,3-(methylenedioxy)-5-methyl-7-hydroxy-8-methoxybenzo[c]-phenanthridinium, 5-(3-aminopropylamino)-7,10-dihydroxy-2-(2-hydroxyethylaminomethyl)-6H-pyrazolo[4,5,1-de]acridin-6-one, N-[1-[2-(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna.

Examples of inhibitors of mitotic kinesins include, but are not limited to inhibitors of KSP, inhibitors of MKLP1, inhibitors of CENP-E, inhibitors of MCAK, inhibitors of Kif14, inhibitors of Mphosph1 and inhibitors of Rab6-KIFL.

Examples of "histone deacetylase inhibitors" include, but are not limited to, vorinostat, trichostatin A, oxamflatin, PXD101, MG98, valproic acid and scriptaid.

"Inhibitors of kinases involved in mitotic progression" include, but are not limited to, inhibitors of aurora kinase, inhibitors of Polo-like kinases (PLK; in particular inhibitors of PLK-1), inhibitors of bub-1 and inhibitors of bub-R1. An example of an "aurora kinase inhibitor" is VX-680.

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N6-[4-deoxy-4-[N2-[2,4-tetradecadienoyl]glycylamino]-L-glycero-B-L-manno-heptopyranosyl]adenine, aplidine, ecteinascidin, troxacitabine, aminopterin, 5-fluorouracil, floxuridine, methotrexate, leucovarin, hydroxyurea, thioguanine (6-TG), mercaptopurine (6-MP), cytarabine, pentostatin, fludarabine phosphate, cladribine (2-CDA), asparaginase, gemcitabine, alanosine, swainsonine, lometrexol, dexrazoxane, methioninase, and 3-aminopyridine-2-carboxaldehyde thiosemicarbazone.

Non-limiting examples of suitable agents used in cancer therapy that may be combined with compounds of formula I include, but are not limited to, abarelix; aldesleukin; alemtuzumab; alitretinoin; allopurinol; altretamine; amifostine; anastrozole; arsenic trioxide; asparaginase; azacitidine; bendamustine; bevacuzimab; bexarotene; bleomycin; bortezomib; busulfan; calusterone; capecitabine; carboplatin; carmustine; cetuximab; chlorambucil; cisplatin; cladribine; clofarabine; cyclophosphamide; cytarabine; dacarbazine; dactinomycin, actinomycin D; dalteparin; darbepoetin alfa; dasatinib; daunorubicin; degarelix; denileukin diftitox; dexrazoxane; docetaxel; doxorubicin; dromostanolone propionate; eculizumab; Elliotts B Solution; eltrombopag; epirubicin; epoetin alfa; erlotinib; estramustine; etoposide phosphate; etoposide; everolimus; exemestane; filgrastim; floxuridine; fludarabine; fluorouracil; fulvestrant; gefitinib; gemcitabine; gemtuzumab ozogamicin; goserelin acetate; histrelin acetate; hydroxyurea; ibritumomab tiuxetan; idarubicin; ifosfamide; imatinib mesylate; interferon alfa 2a; interferon alfa-2b; irinotecan; ixabepilone; lapatinib; lenalidomide; letrozole; leucovorin; leuprolide acetate; levamisole; lomustine; mechlorethamine, nitrogen mustard; megestrol acetate; melphalan, L-PAM; mercaptopurine; mesna; methotrexate; methoxsalen; mitomycin C; mitotane; mitoxantrone; nandrolone phenpropionate; nelarabine; nilotinib; Nofetumomab; ofatumumab; oprelvekin; oxaliplatin; paclitaxel; palifermin; pamidronat; panitumumab; pazopanib; pegademase; pegaspargase; Pegfilgrastim; pemetrexed disodium; pentostatin; pipobroman; plerixafor; plicamycin, mithramycin); porfimer sodium; pralatrexate; procarbazine; quinacrine; Rasburicase; raloxifene hydrochloride; Rituximab; romidepsin; romiplostim; sargramostim; sargramostim; satraplatin; sorafenib; streptozocin; sunitinib maleate; tamoxifen; temozolomide; temsirolimus; teniposide; testolactone; thioguanine; thiotepa; topotecan; toremifene; tositumomab; trastuzumab; tretinoin; uracil mustard; valrubicin; vinblastine; vincristine; vinorelbine; vorinostat; and zoledronate.

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates, to optimise the activity and/or stability and/or physical characteristics, such as solubility, of the therapeutic ingredient. It will be clear also that, where appropriate, the therapeutic ingredients may be used in optically pure form.

The combinations referred to above may conveniently be presented for use in the form of a pharmaceutical composition and thus pharmaceutical compositions comprising a combination as defined above together with a pharmaceutically acceptable diluent or carrier represent a further aspect of the invention. These combinations are of particular interest in respiratory diseases and are conveniently adapted for inhaled or intranasal delivery.

The individual compounds of such combinations may be administered either sequentially or simultaneously in separate or combined pharmaceutical compositions. Preferably, the individual compounds will be administered simultaneously in a combined pharmaceutical composition. Appropriate doses of known therapeutic agents will be readily appreciated by those skilled in the art.

Syk inhibition may be determined using the following assay protocol:

Biological Assay

Homogeneous Time-Resolved Fluorescence (HTRF) Assay for the Recombinant Human Syk Enzyme:

A recombinant GST-hSyk fusion protein was used to measure potency of compounds to inhibit human Syk activity. The recombinant human GST-Syk (Carna Biosciences #08-176) (5 pM final concentration) was incubated with various concentrations of the inhibitor diluted in DMSO (0.1% final concentration) for 10 minutes at room temperature in 15 mM Tris-HCl (pH 7.5), 0.01% tween 20, 2 mM DTT in 384 well plate format. To initiate the reaction the biotinylated substrate peptide (250 nM final concentration) that contains the phosphorylation site for Syk was added with magnesium (5 mM final concentration) and ATP (25 µM final concentration). Final volume of the reaction was 10 µL. Phosphorylation of the peptide was allowed to proceed for 45' at room temperature. To quench the reaction and detect the phosphorylated product, 2 nM of a Europium-anti-phosphotyrosine antibody (Perkin Elmer #AD0161) and 70 nM SA-APC (Perkin-Elmer #CR130-100) were added together in 15 mM Tris pH 7.5, 40 mM EDTA, 0.01% tween 20. Final volume of the quenching solution was 10 µL. The resulting HTRF signal was measured after 30 minutes on a EnVision (Perkin-Elmer) reader using a time-resolved fluorescence protocol. $IC_{50}$ was determined by fitting the observed relationship between compound concentration (10-dose titration, 10 µM to 0.508 nM) and HTRF signal with a 4-parameter logistic equation.

The compounds of this invention may be made by a variety of methods, including standard chemistry. Illustrative general synthetic methods are set out below and then specific compounds of the invention are prepared in the Examples. Any previously defined variable will continue to have the previously defined meaning unless otherwise indicated.

Compounds of general formula I may be prepared by methods known in the art of organic synthesis as set forth in part by the following synthesis schemes. In all of the schemes described below, it is well understood that protecting groups for sensitive or reactive groups are employed where necessary in accordance with general principles of chemistry. Protecting groups are manipulated according to standard methods of organic synthesis (T. W. Green and P. G. M. Wuts (1991) Protecting Groups in Organic Synthesis, John Wiley & Sons). These groups are removed at a convenient stage of the compound synthesis using methods that are readily apparent to those skilled in the art. The selection of protecting groups as well as the reaction conditions and order of reaction steps shall be consistent with the preparation of compounds of formula I. Those skilled in the art will recognize if a stereocenter exists in compounds of formula I. Accordingly, the present invention includes all possible stereoisomers and includes not only mixtures of stereoisomers (such as racemic compounds) but the individual stereoisomers as well. When a compound is desired as a single enantiomer, it may be obtained by stereospecific or stereoselective synthesis or by resolution of the final product or any convenient intermediate. Resolution of the final product, an intermediate, or a starting material may be affected by any suitable method known in the art. See, for example, Stereochemistry of Organic Compounds by E. L. Eliel, S. H. Wilen, and L. N. Mander (Wiley-Interscience, 1994).

The following abbreviations are used in the schemes and examples: Ac=Acetyl; AcOH=Acetic acid; Bn=benzyl; Boc (t-Boc)=t-butyloxycarbonyl; BOP=(Benzotriazol-1-yloxy)-tris(dimethylamino)phosphonium hexafluorophosphate; DAST=(Diethylamino)sulfur trifluoride; dba=dibenzylideneacetone; DCE=1,2-dichloroethane; DCM=Dichloromethane; Dibal/Dibal-H=Diisobutylaluminum hydride; DIPEA/DIEA=Diisopropylethylamine; DMAP=N,N-dimethyl-aminopyridine; DME=1,2-dimethoxyethane; DMF=Dimethyl formamide; DMSO=Dimethylsulfoxide; Dppf=1,1'-Bis (diphenylphosphino)ferrocene; EDC=N-(3-Dimethylaminopropyl)-N'-ethylcarbodiimide; EtOAc=Ethyl acetate; HATU=N,N,N',N'-Tetramethyl-O-(7-azabenzotriazol-1-yl) uronium hexafluorophosphate; HMDS=Hexamethyldisilazane; HOBT=1-Hydroxybenzotriazole; HPLC=high pressure liquid chromatography; IPA=Isopropyl alcohol; LDA=Lithium diisopropylamide; mCPBA=Meta-chloroperoxybenzoic acid; Ms=Methanesulfonyl (mesyl); MTBE=Methyl t-butyl ether; NBS=N-bromosuccinimide; Ph=phenyl; SFC=supercritical fluid chromatography; TBAF=t-butylammonium fluoride; TBDMS/TBS=t-butyl dimethylsilyl; TFA=Trifluoroacetic/trifluoroacetate; THF=Tetrahydrofuran; TLC=Thin-layer chromatography; TMS=Trimethylsilyl; Ts=Toluenesulfonyl (tolyl); TSA=p-toluenesulfonic acid. Abbreviations for alkylcycloalkyl groups: Me=methyl, Et=ethyl, nPr=n-propyl, iPr=isopropyl, nBu=n-butyl, t-Bu=tertiary butyl, cPr=cyclopropyl, cBu=cyclobutyl, cPen=cyclopentyl, cHex=cyclohexyl, cHept=cycloheptyl.
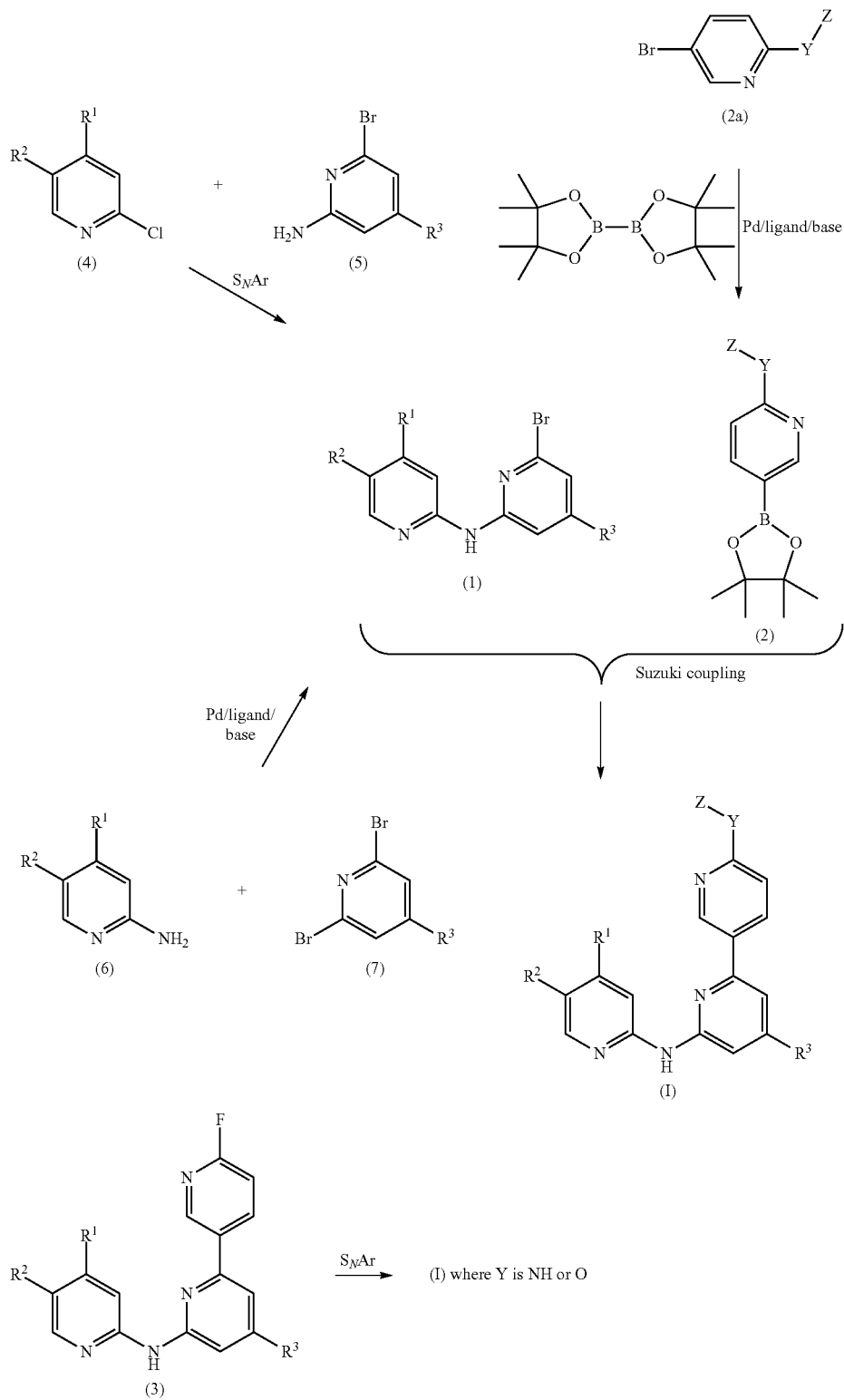

Compounds of formula I are prepared by Suzuki coupling of pyridyl bromides (1) with pyridyl boronate esters (2). Pyridyl boronate esters (2) are formed by Miyaura borylation of the corresponding bromides (2a). Pyridyl bromides (1) are obtained by reacting 2-chloropyridines (4) and 2-amino-6-bromopyridines under base-mediated $S_NAr$ conditions. Alternatively, pyridyl bromides (1) can be formed by reaction of 2-aminopyridines with 2,6-dibromopyridines under palladium-mediated C—N coupling conditions. Some compounds of formula I can also be prepared by $S_NAr$ reaction of fluoropyridine (3) with an appropriate nucleophile.

SCHEME 2

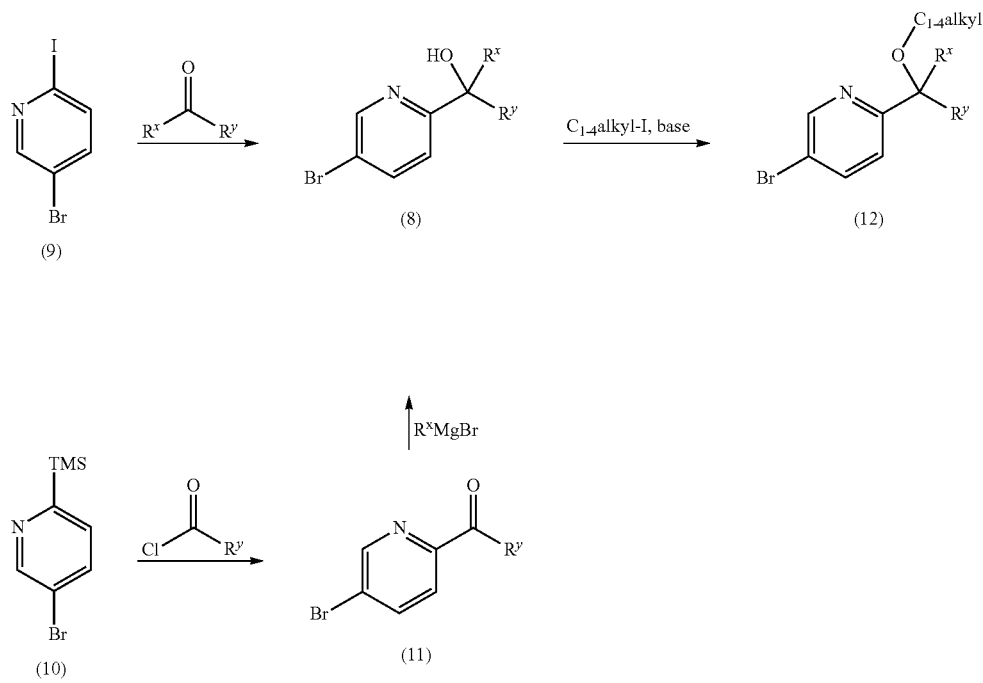

Compounds of formula (8) are prepared by metallation of 2-iodopyridine (9) and addition to a carbonyl electrophile. Alternatively, 2-trimethylsilyl pyridine (10) reacts with acyl chlorides to afford pyridyl ketones (11), which react with Grignard reagents to form compounds of formula (8). Deprotonation of alcohol (8) and treatment with an electrophile gives compounds of formula (12). Compounds of formula (8) and (12) are converted to pyridyl boronates (2) and ultimately, compounds of formula I.

SCHEME 3

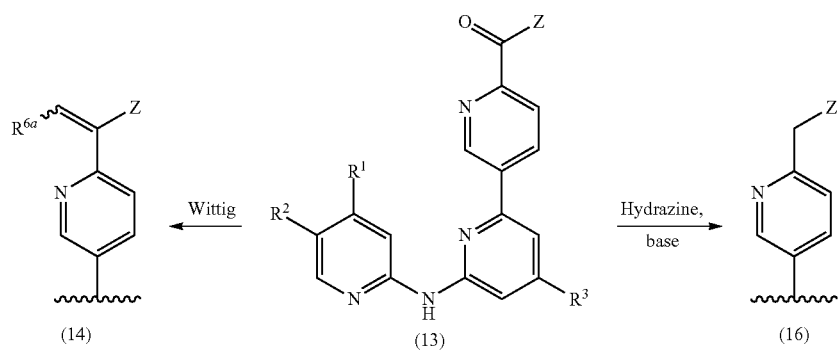

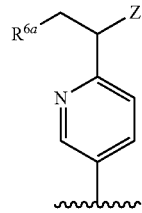

(15)

$R^{6a}$ = H, $C_{1-3}$alkyl

Compounds of formula (15) are prepared by reacting pyridyl ketones (13) under Wittig conditions to provide the corresponding olefin (14). Reduction of pyridyl olefins (14) under hydrogenation conditions provides compounds of formula (15). Also, treatment of ketone (13) under Wolff-Kishner conditions provides the reduced tripyridine (16).

SCHEME 4

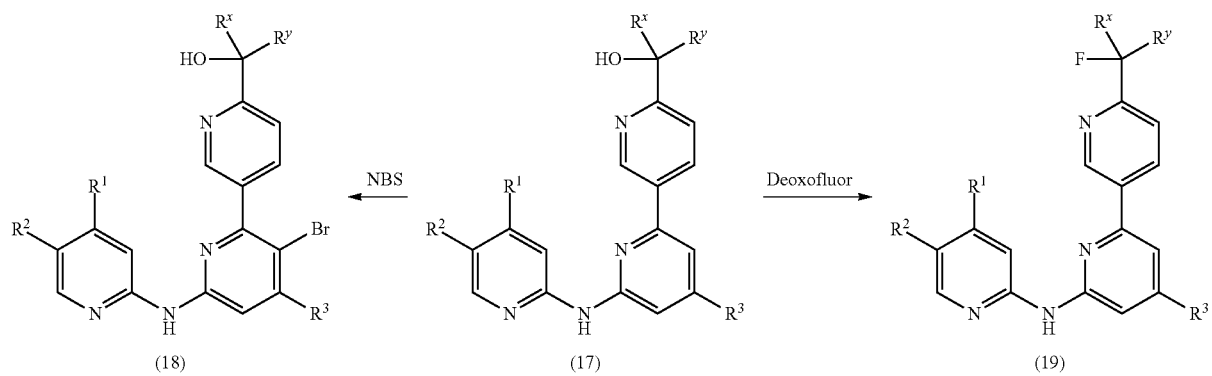

Compounds of formula (17) are brominated by treatment with NBS to afford (18) or fluorinated by treatment with Deoxofluor to give (19).

SCHEME 5

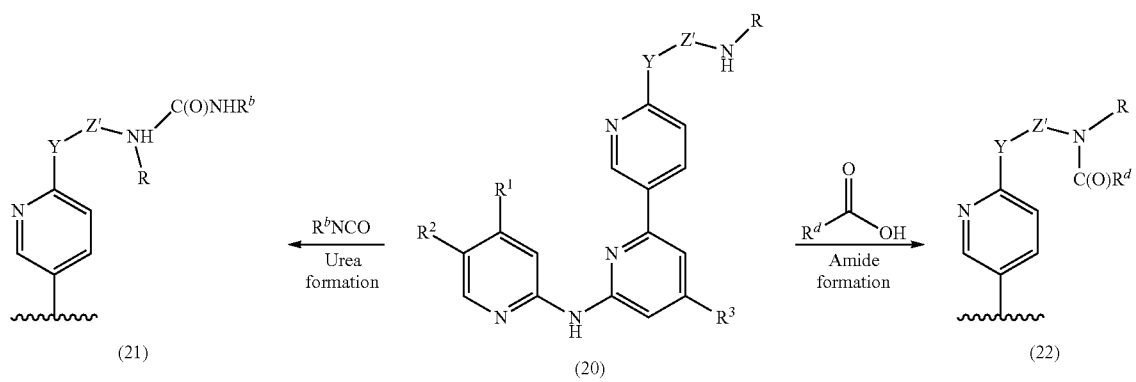

Z' (and R = H) Z'—N—R together represent an optionally substituted ring within the definition of Z Ureas (21) are formed by treatment of amine (20) with isocyanates. Alternatively, amide coupling reagents, such as DCC, are used to make amides (22) from amine (20) and the corresponding carboxylic acid.

SCHEME 6

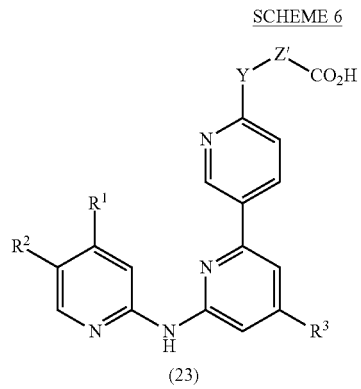

(23)

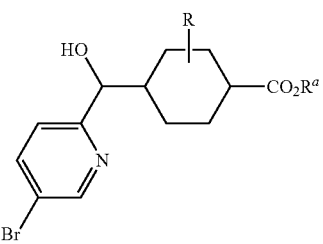

(24)

Z' represents an optionally substituted ring within the definition of Z

Amides (24) are formed by treatment of acid (23) with amide coupling reagents, such as DCC, and the corresponding amine.

SCHEME 7

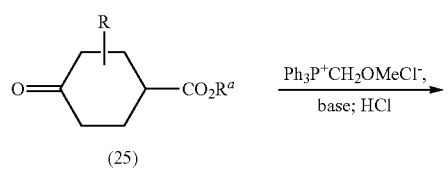

(25)

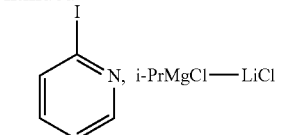

(26)

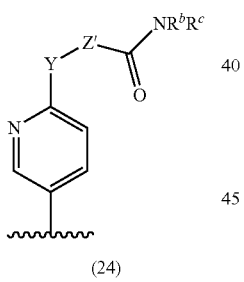

(27)

(28)

R = H, or 1 or 2 $C_{1-4}$ alkyl

Preparation of substituted cyclohexyl derivatives is illustrated in Scheme 7. Substituted keto esters (25) are homologated via a Wittig/hydrolysis sequence to the corresponding aldehydes (26). Addition of a metallated pyridine provides alcohols (27). Oxidation of the alcohol, followed by Grignard addition affords substituted cyclohexyl derivates (28), which can be used as shown in Scheme 1 to prepare compounds of formula I.

SCHEME 8
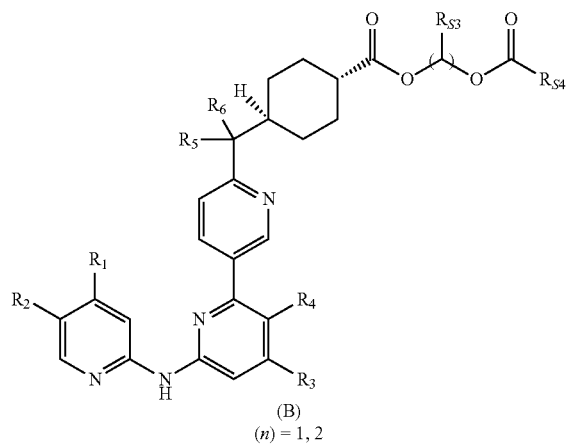
(B)
(n) = 1, 2
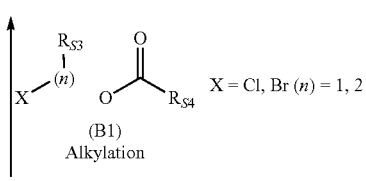
X = Cl, Br (n) = 1, 2
(B1)
Alkylation
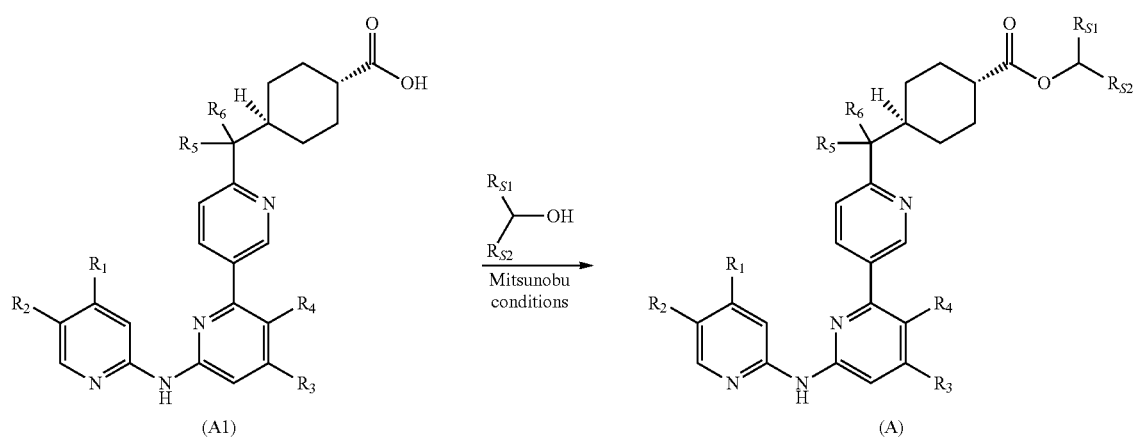
(A1) → (A)
Mitsunobu conditions
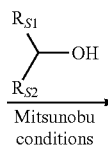
(C1)
Alkylation

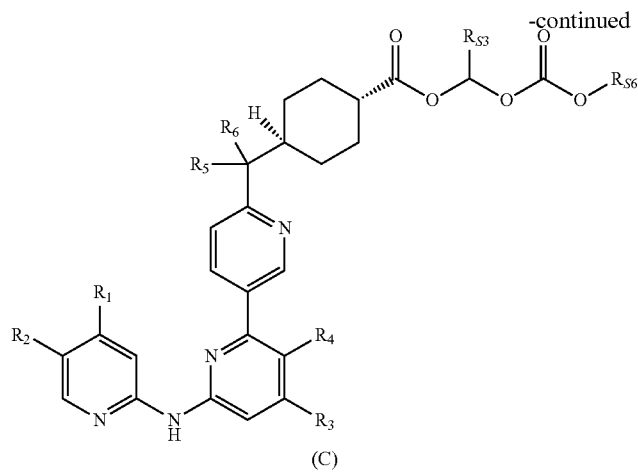

(C)

As shown in Scheme 8, compounds of structural subtype A are prepared from the trans-cyclohexane carboxylic acid (A1) by a Mitsunobu reaction with various primary and secondary alcohols. Compounds of structural subtype B are prepared by the alkylation of the trans-cyclohexane carboxylic acid (A1) by alkyl halides of formula (B1). Compounds of structural subtype C are prepared by the alkylation of the trans-cyclohexane carboxylic acid (A1) by alkyl halides of formula (C1).

As shown in Scheme 9, compounds of structural subtype D are prepared by the reaction of the trans-cyclohexane carboxylic acid (A1) with trimethylsilyldiazomethane and methanol.

SCHEME 9

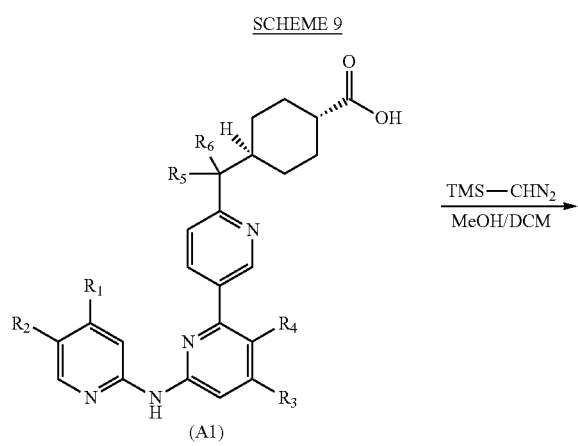

SCHEME 10

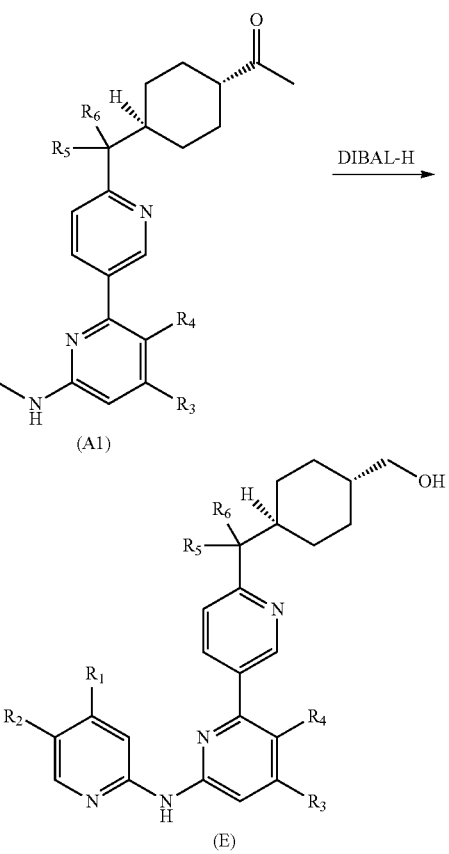

As shown in Scheme 10, compounds of structural subtype E are prepared by the reduction of the trans-cyclohexane carboxylic acid (A1) with diisobutylaluminum hydride.

Compounds of formula I can be prepared according to the procedures described in the Schemes and Examples herein, using appropriate materials and are further exemplified by the following specific examples. The compounds exemplified are illustrative of the invention and are not, however, to be construed as limiting the scope of the invention in any manner. The examples further illustrate details for the preparation of the compounds of the present invention. Those skilled in the art will readily understand that known variations of protecting groups, of reagents, as well as of the conditions and processes of the following preparative procedures, can be used to prepare these compounds. It is also understood that whenever a chemical reagent is not commercially available, such a chemical reagent can be readily prepared by those skilled in the art by either following or adapting known methods described in the literature. All temperatures are degrees Celsius unless otherwise noted. Mass spectra (MS) were measured either by electrospray ion-mass spectroscopy (ESI) or by atmospheric pressure chemical ionization mass spectroscopy (APCI).

Intermediate 1

4-Cyclopropylpyridin-2-amine

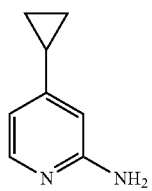

A mixture of 4-chloropyridin-2-amine (2.6 g, 15 mmol), cyclopropylboronic acid (2.6 g, 30 mmol), [1,1'-bis(diphenylphosphino)ferrocene]dichloropalladium(II) (1.2 g, 1.5 mmol), and potassium carbonate (4.0 g, 30 mmol) in 1,4-dioxane (40 mL) and water (5 mL) was stirred at 80° C. for 15 hours. After allowing to cool to room temperature, the reaction mixture was filtered, and the filtrate was concentrated under reduced pressure. The residue was purified by column chromatography on silica gel (petroleum ether:ethyl acetate=5:1) to give 4-cyclopropylpyridin-2-amine. MS ESI calcd. for $C_8H_{11}N_2$ $[M+H]^+$ 135, found 135. $^1$H NMR (400 MHz, CDCl$_3$) δ 7.91 (d, J=6.0 Hz, 1H), 6.31-6.29 (m, 1H), 6.23-6.22 (m, 1H), 4.99 (s, 2H), 1.79-1.72 (m, 1H), 1.06-1.01 (m, 2H), 0.78-0.74 (m, 2H).

Intermediate 2

2,6-Dichloro-4-cyclopropylpyridine

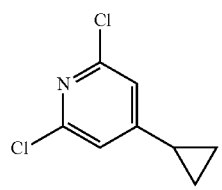 [SMILES: Clc1cc(C2CC2)cc(Cl)n1]

Cyclopropylzinc bromide (0.5 M in tetrahydrofuran, 15 mL, 7.3 mmol) was added to a mixture of 2,6-dichloro-4-iodopyridine (1.0 g, 3.65 mmol) and tetrakis(triphenylphosphine)palladium(0) (211 mg, 0.182 mmol) in anhydrous tetrahydrofuran (10 mL) at 0° C. After being stirred at room temperature for 4 hours, the reaction mixture was filtered, and the filtrate was concentrated under reduced pressure. The residue was purified by column chromatography on silica gel (petroleum ether:ethyl acetate=100:1) to provide 2,6-dichloro-4-cyclopropylpyridine. MS ESI calcd. for $C_8H_8Cl_2N$ $[M+H]^+$ 188, found 188. $^1$H NMR: (400 MHz, CDCl$_3$) δ 6.89 (s, 2H), 1.87-1.80 (m, 1H), 1.18-1.13 (m, 2H), 0.84-0.80 (m, 2H).

Intermediate 3

2-(2,6-Dibromopyridin-4-yl)propan-2-ol

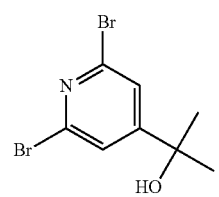

Methylmagnesium bromide (3.0 M, 14.3 mL, 43 mmol) was added to a solution of methyl 2,6-dibromopyridine-4-carboxylate (5 g, 17 mmol) in tetrahydrofuran (100 mL) at 0° C. The reaction mixture was allowed to warm to room temperature and was stirred at that temperature for 1 hour. The mixture was then diluted with saturated aqueous ammonium chloride solution, and extracted with ethyl acetate (3×100 mL). The combined organic layers were dried over sodium sulfate, filtered, and concentrated under reduced pressure. The residue was purified by column chromatography on silica gel to afford 2-(2,6-dibromopyridin-4-yl)propan-2-ol. MS ESI calcd. for $C_8H_{10}Br_2NO$ $[M+H]^+$ 294, 296, and 298. found 294, 296, and 298. $^1$H NMR (400 MHz, CDCl$_3$) δ 7.53 (s, 2H), 1.88 (s, 1H), 1.54 (s, 6H).

Intermediate 4

6-Bromo-4-methyl-N-[4-(trifluoromethyl)pyridine-2-yl]pyridine-2-amine

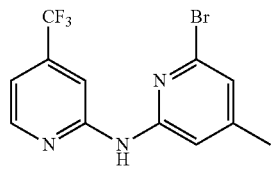 [SMILES: Cc1cc(Br)nc(Nc2cc(C(F)(F)F)ccn2)c1]

To a flask containing 2,6-dibromo-4-methylpyridine (13.9 g, 55.5 mmol) and 2-amino-4-trifluoromethylpyridine (9.0 g, 55.5 mmol) was added nitrogen sparged dioxane (180 mL). Sodium tert-butoxide (5.87 g, 61.1 mmol) and 1,1'-bis(di-tert-butylphsophino)ferrocene palladium dichloride (0.905 g, 1.4 mmol) were then added, and the slurry was evacuated and refilled with nitrogen. The mixture was stirred at 25° C. for 15 minutes and then heated to 75° C. for 12 hours. The reaction was cooled to 25° C., water (20 mL) was added, and the mixture was extracted with ethyl actetate (2×200 mL). The combined extracts were dried over Na$_2$SO$_4$, filtered, concentrated in vacuo. The residue was purified via chromatography on silica gel to afford 6-bromo-4-methyl-N-[4-(trifluoromethyl)pyridine-2-yl]pyridine-2-amine as a white solid. MS ESI calcd. for $C_{12}H_{10}BrF_3N_3$ [M+H]$^+$ 332 and 334. found 332 and 334. $^1$H NMR (600 MHz, DMSO-$d_6$) δ 10.40 (s, 1H), 8.46 (d, J=6.0 Hz, 1H), 7.90 (s, 1H), 7.60 (s, 1H), 7.18 (d, J=6.0 Hz, 1H), 7.00 (s, 1H), 2.25 (s, 3H).

The intermediates in the following Table were prepared according to the method described for intermediate 4.

| Intermediate | Structure | [M + H]+ Obs'd |
|---|---|---|
| 5 | 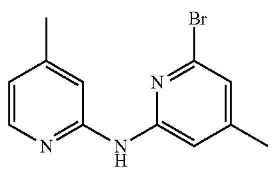 [SMILES: Cc1ccnc(Nc2cc(C)cc(Br)n2)c1] | 278, 280 |
| 6 | 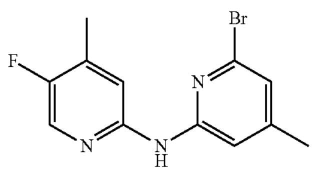 [SMILES: Cc1cc(Br)nc(Nc2cc(C)c(F)cn2)c1] | 296, 298 |
| 7 | 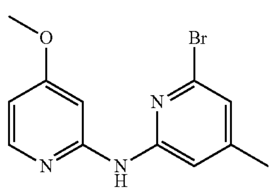 [SMILES: COc1ccnc(Nc2cc(C)cc(Br)n2)c1] | 294, 296 |
| 8 | 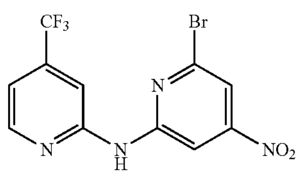 [SMILES: O=[N+]([O-])c1cc(Br)nc(Nc2cc(C(F)(F)F)ccn2)c1] | 363, 365 |
| 9 | 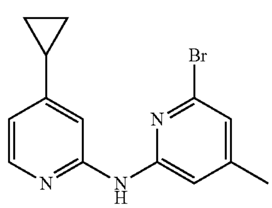 [SMILES: Cc1cc(Br)nc(Nc2cc(C3CC3)ccn2)c1] | 304, 306 |
| 10 | 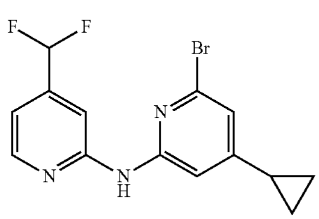 [SMILES: FC(F)c1ccnc(Nc2cc(C3CC3)cc(Br)n2)c1] | 340, 342 |
| 11 | 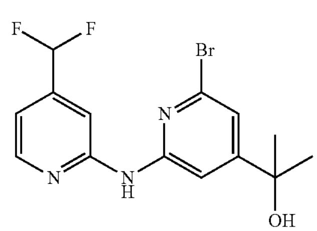 [SMILES: CC(C)(O)c1cc(Br)nc(Nc2cc(C(F)F)ccn2)c1] | 358, 360 |

Intermediate 12

6-Bromo-N-[4-(difluoromethyl)pyridin-2-yl]-4-methylpyridin-2-amine

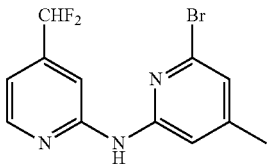 [SMILES: Cc1cc(Br)nc(Nc2cc(C(F)F)ccn2)c1]

Potassium t-butoxide (1.0 M in THF, 198 mL, 198 mmol) was added to a solution of 6-bromo-4-methylpyridine-2-amine (37 g, 198 mmol) and 2-chloro-4-(difluoromethyl)pyridine (42.1 g, 257 mmol) in THF (60 mL) at 0° C. The resulting mixture was heated to reflux for 30 minutes then cooled to 0° C., and a second portion of potassium t-butoxide (1.0 M in THF, 80 mL, 80 mmol) was added. The mixture was again heated to reflux for 30 minutes, cooled to 0° C., and a third portion of potassium t-butoxide (1.0 M in THF, 80 mL, 80 mmol) was added. The mixture was again heated to reflux for 30 minutes. After cooling to 0° C., a fourth portion of potassium t-butoxide (1.0 M in THF, 20 mL, 20 mmol) was added. Upon refluxing for 30 minutes, the reaction was allowed to cool to room temperature, then diluted with saturated aqueous NH$_4$Cl (500 mL) and diluted with DCM (500 mL). The layers were separated, and the aqueous layer was extracted a second time with DCM (500 mL). The combined organic layers were dried with Na$_2$SO$_4$, filtered through a pad of CELITE (150 g), and concentrated in vacuo. The residue was triturated with DCM (100 mL), filtered, and washed with hexanes (2×50 mL) to afford one portion of 6-bromo-N-[4-(difluoromethyl)pyridin-2-yl]-4-methylpyridin-2-amine.

The filtrate was concentrated, absorbed on silica gel and purified via silica gel column chromatography (EtOAc/Hex) to afford a second portion of 6-bromo-N-[4-(difluoromethyl)pyridin-2-yl]-4-methylpyridin-2-amine. MS ESI calcd. for $C_{12}H_{11}BrF_2N_3$ [M+H]$^+$ 314 and 316. found 314 and 316. $^1$H NMR (600 MHz, DMSO-$d_6$) δ 10.20 (s, 1H), 8.35 (d, J=5.1 Hz, 1H), 7.69 (s, 1H), 7.64 (s, 1H), 7.01 (d, J=5.1 Hz, 1H), 6.96 (t, J=22.3 Hz, 1H), 6.95 (s, 1H), 2.24 (s, 3H).

Intermediate 13

6-Bromo-N$^2$-[4-(trifluoromethyl)pyridin-2-yl]pyridine-2,4-diamine

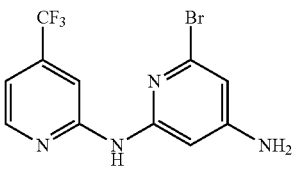

A suspension of 6-bromo-4-nitro-N-[4-(trifluoromethyl)pyridin-2-yl]pyridin-2-amine (586 mg, 1.614 mmol) and iron (361 mg, 6.46 mmol) in acetic acid (7 mL) was heated to 50° C. for 1 hour. The reaction mixture was partitioned between ethyl acetate (70 mL) and water (70 mL). The aqueous layer was further extracted with ethyl acetate (70 mL), and the combined organic layers were washed with water (70 mL), saturated aqueous sodium bicarbonate solution (2×70 mL), brine (50 mL), dried over sodium sulfate, filtered, and concentrated under reduced pressure. The residue was purified by chromatography on silica gel (10-60% ethyl acetate/hexanes) to afford 6-bromo-$N^2$-[4-(trifluoromethyl)pyridin-2-yl]pyridine-2,4-diamine. MS ESI calcd. for $C_{11}H_9BrF_3N_4$ $[M+H]^+$ 333 and 335. found 333 and 335. $^1H$ NMR (500 MHz, DMSO-$d_6$) δ 11.08 (s, 1H), 8.63 (s, 1H), 8.59 (d, J=5.4 Hz, 1H), 7.85 (s, 1H), 7.83-7.76 (m, 2H), 7.48-7.42 (m, 1H), 7.37-7.32 (m, 1H).

Intermediate 14

Methyl 2,2-dimethyl-4-oxocyclohexanecarboxylate

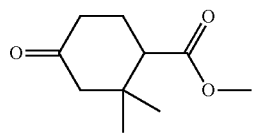

Step 1:

Methyl 3-oxobutanoate (232 g, 2.00 mol) and paraformaldehyde (30 g, 999 mmol) were combined, and to the mixture was added piperidine (10 g, 117.44 mmol). The resulting solution was stirred for 2 h at 0° C. The solution was heated to 60° C. for 2 hours. Extracted with $Et_2O$ (3×), and the organic layers were combined and dried over $Na_2SO_4$, filtered, and concentrated in vacuo. Dimethyl 2-methyl-6-oxocyclohex-1-ene-1,3-dicarboxylate was obtained as a brown oil. MS ESI calcd. for $C_{11}H_{15}O_5$ $[M+H]^+$ 227. found 227.

Step 2:

To a solution of sodium methanolate (90 g, 1.67 mol) in methanol (300 mL) was added dimethyl 2-methyl-6-oxocyclohex-1-ene-1,3-dicarboxylate (150 g, 663.04 mmol) in methanol (150 mL) dropwise with stirring over 30 minutes. The resulting solution was heated to 80° C. for 30 minutes, and the mixture was concentrated in vacuo. The reaction mixture was diluted with $H_2O$/ice (120 mL); then diluted further with acetic acid (130 mL). The resulting solution was extracted with $Et_2O$ (3×), and the organic layers were combined and dried over $Na_2SO_4$, filtered, and concentrated in vacuo. The final product was purified by distillation under reduced pressure (5 mm Hg), and the fraction was collected at 110~120° C. Methyl 2-methyl-4-oxocyclohex-2-enecarboxylate was obtained as a yellow oil. MS ESI calcd. for $C_9H_{13}O_3$ $[M+H]^+$ 169. found 169.

Step 3:

Copper iodide (121.8 g, 639.54 mmol) was suspended in $Et_2O$ (800 mL). Methyllithium (1.6 M in diethyl ether, 800 mL, 1.28 mol) was added dropwise at −40° C. over 3 hours. A solution of methyl 2-methyl-4-oxocyclohex-2-enecarboxylate (53.8 g, 319.88 mmol) in $Et_2O$ (400 mL) was added at −40° C. over 2 minutes. The resulting solution was stirred 5 hours at −20° C. The mixture was diluted with saturated aqueous ammonium chloride (2.5 L) and extracted with EtOAc (3×2 L). The combined organic extracts were dried over $Na_2SO_4$, filtered, and concentrated in vacuo. The residue was purified via silica gel column chromatography (1:20 EtOAc/petroleum ether). Methyl 2,2-dimethyl-4-oxocyclohexanecarboxylate was obtained as a yellow oil. MS ESI calcd. for $C_{10}H_{17}O_3$ $[M+H]^+$ 185. found 185. $^1H$ NMR (600 MHz, CDCl$_3$) δ 3.49 (s, 3H), 2.43-2.40 (m, 1H), 2.35-2.29 (m, 1H), 2.21-2.17 (m, 1H), 2.11-2.04 (m, 1H), 2.00-1.96 (m, 1H), 1.91-1.85 (m, 1H), 0.85 (s, 3H), 0.77 (s, 3H).

Intermediate 15

Butyl trans-4-acetylcyclohexanecarboxylate

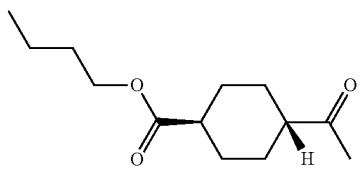 [SMILES: CCCCOC(=O)[C@H]1CC[C@H](C(C)=O)CC1]

To a cooled solution (0° C.) under nitrogen of trans-4-(butoxycarbonyl)cyclohexanecarboxylic-acid (18.9 g, 83 mmol) in $CH_2Cl_2$ (150 mL) was added a catalytic amount of DMF (30 μL) followed by oxalyl chloride (7.97 mL, 91 mmol). The reaction mixture was then allowed to slowly warm to room temperature where it was stirred for 14 hours at which point it was concentrated to a yellow oil and dried under vacuum for 3 hours. The residue (consisting primarily of butyl trans-4-(chlorocarbonyl)cyclohexanecarboxylate) was diluted with THF (200 mL) and cooled in an ice bath. To this solution was added $PdCl_2$(dppf)-$CH_2Cl_2$ (3.38 g, 4.14 mmol, 5 mol %) followed by dimethyl zinc (2 M in $PhCH_3$, 29 mL, 58 mmol, 0.7 equiv) at such a rate that the internal temperature did not exceed 15° C. The cooling bath was then removed and after 2 hours of stirring at room temperature the reaction mixture was re-cooled to 0° C. where it was diluted carefully with $H_2O$. After the initial exotherm had subsided, sufficient 1N HCl and EtOAc were introduced such that a homogenous biphasic mixture formed. The layers were separated, the organic washed a second time with $H_2O$ then dried with $MgSO_4$, filtered and concentrated in vacuo. The crude residue was absorbed on silica and purified by flash chromatography to afford butyl trans-4-acetylcyclohexanecarboxylate as a non-viscous orange oil. MS ESI calcd. for $C_{13}H_{23}O_3$ $[M+H]^+$ 227. found 227. $^1H$ NMR (500 MHz, CDCl$_3$) δ 4.06 (t, J=6.6 Hz, 2H), 2.33 (m, J=3.4, 11.8 Hz, 1H), 2.24 (tt, J=3.6, 12.1 Hz, 1H), 2.14 (s, 3H), 2.11-2.02 (m, 2H), 1.99 (d, J=13.8 Hz, 2H), 1.66-1.55 (m, 2H), 1.51-1.40 (m, 2H), 1.39-1.29 (m, 4H), 0.93 (t, J=7.4 Hz, 3H).

The intermediate in the following Table was prepared according to the method described for intermediate 15.

| Intermediate | Structure | [M + H]+ Obs'd |
|---|---|---|
| 16 | 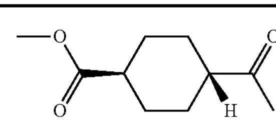 | 185 |

Intermediate 17 trans-Butyl 4-(1-(5-chloropyridin-2-yl)-1-hydroxy-ethyl)cyclohexanecarboxylate

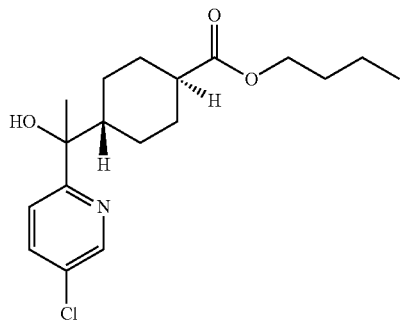 [SMILES: CCCCOC(=O)[C@H]1CC[C@H](C(C)(O)c2ccc(Cl)cn2)CC1]

Tert-butyllithium (1.6 M in hexane, 3.3 mL, 5.28 mmol) was added dropwise over a period of 1 minute to a solution of 2-bromo-5-chloropyridine (0.8 g, 4.16 mmol) in dichloromethane (21 mL) at −78° C. The mixture was stirred for 90 minutes at −78° C., then a solution of trans-butyl 4-acetylcyclohexanecarboxylate (1.035 g, 4.57 mmol) in dichloromethane (1 mL) was added. The reaction was then allowed to warm to 23° C. over a period of 16 hours and subsequently diluted with saturated aqueous ammonium chloride solution. The resulting slurry was extracted with dichloromethane (3×70 mL), and the combined organic fractions were dried over sodium sulfate, filtered, and concentrated in vacuo. Purification of the residue by silica gel column chromatography (EtOAc/hexanes) afforded racemic trans-butyl 4-(1-(5-chloropyridin-2-yl)-1-hydroxyethyl)cyclohexanecarboxylate as a brown oil. MS ESI calcd. for $C_{18}H_{27}ClNO_3$ [M+H]$^+$ 340. found 340. $^1$H NMR (500 MHz, CDCl$_3$) δ 8.47 (s, 1H), 7.68 (d, J=8.4 Hz, 1H), 7.26 (d, J=8.4 Hz, 1H), 4.68 (s, 1H), 4.03 (t, J=6.6 Hz, 2H), 2.22-1.85 (m, 4H), 1.66-1.53 (m, 4H), 1.48 (s, 3H), 1.42-1.05 (m, 6H), 0.91 (t, J=7.5 Hz, 3H).

Intermediate 18

Methyl trans-4-[1-(5-bromopyridin-2-yl)-1-hydroxy-ethyl]cyclohexanecarboxylate

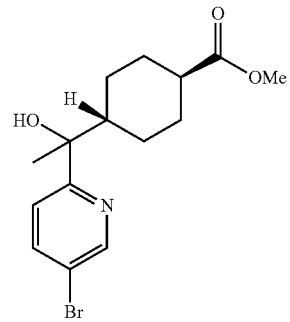 [SMILES: COC(=O)[C@H]1CC[C@H](C(C)(O)c2ccc(Br)cn2)CC1]

To a solution of 5-bromo-2-iodopyridine (18.5 g, 65.1 mmol) in THF (33 mL) at −5° C. was slowly added a solution of i-PrMgCl—LiCl (1.3 M in THF, 50.1 mL, 65.1 mmol) at such a rate that the internal temperature did not exceed −2° C. The reaction mixture was allowed to stir for 1.25 hours at 0° C., and methyl trans-4-acetylcyclohexanecarboxylate (6 g, 32.6 mmol) was added dropwise via syringe. The reaction mixture was stirred for an additional 1 hour at 0° C., then sodium borohydride (0.62 g, 16.3 mmol) was added. The reaction mixture was slowly allowed to warm to room temperature and stirred for 14 hours. The mixture was diluted by addition of saturated aqueous NH$_4$Cl (200 mL) and DCM (250 mL). The layers were separated and the aqueous layer extracted with DCM (250 mL). The combined organic layers were dried with MgSO$_4$, filtered, and concentrated in vacuo. The crude residue was absorbed on silica, gel and purified via silica gel column chromatography (EtOAc/Hexanes) to afford racemic methyl trans-4-[1-(5-bromopyridin-2-yl)-1-hydroxyethyl]cyclohexane carboxylate as a yellow oil. MS ESI calcd. for $C_{15}H_{21}BrNO_3$ [M+H]$^+$ 342 and 344. found 342 and 344. $^1$H NMR (600 MHz, CDCl$_3$) δ 8.54 (d, J=1.8 Hz, 1H), 7.79 (dd, J=8.4, 2.3 Hz, 1H), 7.19 (d, J=8.4 Hz, 1H), 4.65 (s, 1H), 3.61 (s, 3H), 2.16 (m, 1H), 2.05-1.97 (m, 1H), 1.97-1.90 (m, 1H), 1.90-1.83 (m, 1H), 1.56 (m, 1H), 1.45 (s, 3H), 1.37 (m, 1H), 1.31-1.15 (m, 3H), 1.09 (m, 1H).

The intermediates in the following Table were prepared according to the method described for intermediate 18.

| Intermediate | Structure | [M + H]+ Obs'd |
|---|---|---|
| 19 | ![structure](trans, enantiomer 1) | 342, 344 |
| 20 | ![structure](trans enantiomer 2) | 342, 344 |

-continued

| Intermediate | Structure | [M + H]+ Obs'd |
|---|---|---|
| 21 | (cis enantiomer 1) | 342, 344 |
| 22 | (cis, enantiomer 2) | 342, 344 |
| 23 | (trans) | 328, 330 |
| 24 | (cis) | 328, 330 |
| 25 | (enantiomer 1) | 362, 364 |
| 26 | (enantiomer 2) | 362, 364 |
| 27 | 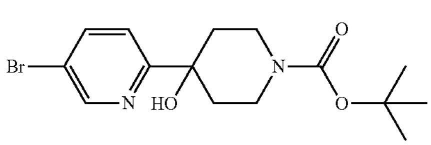 [SMILES: CC(C)(C)OC(=O)N1CCC(O)(c2ccc(Br)cn2)CC1] | 357, 359 |

| Intermediate | Structure | [M + H]+ Obs'd |
|---|---|---|
| 28 | 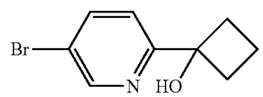 [SMILES: OC1(c2ccc(Br)cn2)CCC1] | 228, 230 |
| 29 | 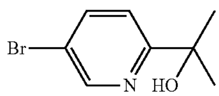 | 198, 200 (dehydration product observed on LCMS) |
| 30 | (1,2-cis, mixture of 8 diastereomers) | 356, 358 |

Intermediates 31a and 31b

Separation of methyl trans-4-[(1R)-1-(5-bromopyridin-2-yl)-1-hydroxyethyl]cyclohexane carboxylate and methyl trans-4-[(1S)-1-(5-bromopyridin-2-yl)-1-hydroxyethyl]cyclohexanecarboxylate

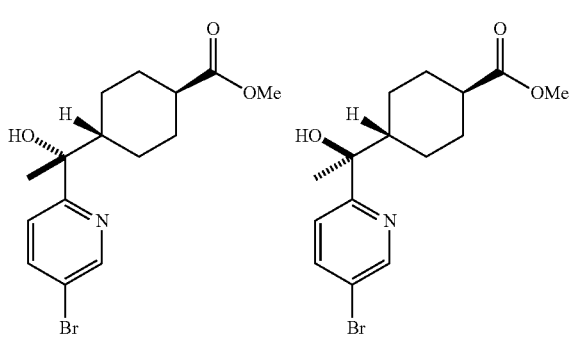 [SMILES: COC(=O)[C@H]1CC[C@H]([C@@](C)(O)c2ccc(Br)cn2)CC1 ; COC(=O)[C@H]1CC[C@H]([C@](C)(O)c2ccc(Br)cn2)CC1]

A racemic mixture of methyl trans-4-[1-(5-bromopyridin-2-yl)-1-hydroxyethyl]cyclohexane carboxylate was separated by chiral SFC purification [Thar 350 preparative SFC, ChiralPak AD-10 um, 300×50 mm I.D., 40% EtOH/$CO_2$ mobile phase, sample dissolved in MeOH ~300 mg/mL, 4.5 mL per injection] to afford methyl trans-4-[(1R)-1-(5-bromopyridin-2-yl)-1-hydroxyethyl]cyclohexane carboxylate and methyl trans-4-[(1S)-1-(5-bromopyridin-2-yl)-1-hydroxyethyl]cyclohexanecarboxylate as single enantiomers.
31a, Faster eluting enantiomer (R or S): MS ESI calcd for $C_{15}H_{21}BrNO_3$ [M+H$^+$ 342 and 344. found 342 and 344.
31b, Slower eluting enantiomer (R or S): MS ESI calcd for $C_{15}H_{21}BrNO_3$ [M+H$^+$ 342 and 344. found 342 and 344.

Intermediate 32

Methyl trans-4-[(5-bromopyridin-2-yl)carbonyl]cyclohexartecarboxylate and Methyl cis-4-[(5-bromopyridin-2-yl)carbonyl]cyclohexanecarboxylate

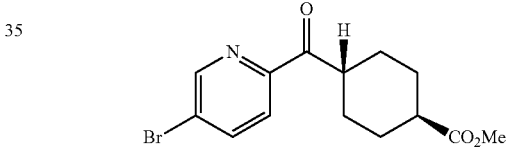

Step 1:

To a flask containing methyl trans-4-(chlorocarbonyl)cyclohexanecarboxylate (8.19 g, 40 mmol) was added 5-bromo-2-(trimethylsilyl)pyridine (8.4 g, 36.4 mmol). The resulting mixture was heated to 110° C. for 10 hours. The reaction was allowed to cool to 70° C., and hexane (30 mL) was added dropwise. The resulting mixture was stirred for 14 hours at room temperature, filtered, and the residue was washed with hexane (20 mL). The beige solid was dried under nitrogen to afford methyl trans-4-[(5-bromopyridin-2-yl)carbonyl]cyclohexanecarboxylate. MS ESI calcd for $C_{14}H_{17}BrNO_3$ [M+H]$^+$ 326 and 328. found 326 and 328. $^1$H NMR (600 MHz, CDCl$_3$) δ 8.70 (d, J=1.8 Hz, 1H), 7.94 (dd, J=8.4, 2.3 Hz, 1H), 7.88 (d, J=8.3 Hz, 1H), 3.78 (tt, J=11.9, 3.4 Hz, 1H), 3.66 (s, 3H), 2.32 (tt, J=12.2, 3.6 Hz, 1H), 2.08 (dd, J=13.8, 3.5 Hz, 2H), 1.99 (dd, J=13.9, 3.1 Hz, 2H), 1.60 (m, 2H), 1.45 (m, 2H).

Step 2:

The filtrate above was concentrated in vacuo to afford a ~3:1 mixture of cis-4-[(5-bromopyridin-2-yl)carbonyl]cyclohexanecarboxylate to trans-4-[(5-bromopyridin-2-yl)carbonyl]cyclohexanecarboxylate, which was used in the next step without further purification. MS ESI calcd for $C_{14}H_{17}BrNO_3$ [M+H]$^+$ 326 and 328. found 326 and 328.

Intermediate 33

Methyl cis-4-[1-(5-bromopyridin-2-yl)-1-hydroxyethyl]cyclohexanecarboxylate

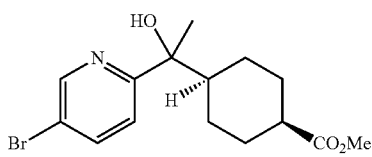 [SMILES: COC(=O)[C@H]1CC[C@@H](C(C)(O)c2ccc(Br)cn2)CC1]

To the 3:1 diastereomeric mixture from step 2 above of cis-4-[(5-bromopyridin-2-yl)carbonyl]cyclohexanecarboxylate and trans-4-[(5-bromopyridin-2-yl)carbonyl]cyclohexanecarboxylate (490 mg, 1.50 mmol) in THF (5 mL) at −40° C. was added methyl magnesium bromide (3 M in Et$_2$O, 0.55 mL, 1.65 mmol). The reaction was aged at −40° C. for 30 min then diluted with saturated aqueous NH$_4$Cl (25 mL). The mixture was extracted with EtOAc (2×50 mL), and the combined organic layers were dried with MgSO$_4$, filtered, and concentrated in vacuo. The crude residue was absorbed on silica gel and purified via silica gel column chromatography to afford a 3:1 mixture of racemic methyl cis-4-[1-(5-bromopyridin-2-yl)-1-hydroxyethyl]cyclohexane carboxylate to racemic methyl trans-4-[1-(5-bromopyridin-2-yl)-1-hydroxyethyl]cyclohexane carboxylate. This mixture was used in a subsequent reaction without further purification. The stereoisomers were separated via chiral SFC and/or reverse phase HPLC chromatography to afford the corresponding examples. Cis isomer: MS ESI calcd. for C$_{15}$H$_{21}$BrNO$_3$ [M+H]$^+$ 342 and 344. found 342 and 344.

The intermediates in the following Table were prepared according to the method described for intermediate 33.

| Intermediate | Structure | [M + H]+ Obs'd |
|---|---|---|
| 34 | 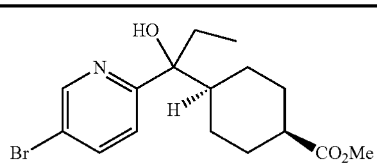 | 356, 358 |
| 35 | 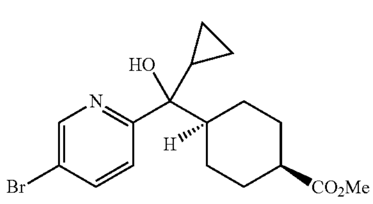 [SMILES: COC(=O)[C@H]1CC[C@@H](C(O)(c2ccc(Br)cn2)C2CC2)CC1] | 368, 370 |
| 36 | 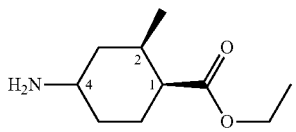 (1,2-cis, mixture of 8 diastereomers) | 356, 358 |

Intermediate 37

Ethyl (1,2-cis)-4-amino-2-methylcyclohexanecarboxylate

Step 1:

To a solution of racemic ethyl (1,2-cis)-2-methyl-4-oxocyclohexanecarboxylate (2.0 g, 10.86 mmol) in 1,2-dichloroethane (110 ml) was added benzylamine (1.221 g, 11.40 mmol) and sodium triacetoxyborohydride (3.34 g, 15.74 mmol). After being stirred for 18 hours at 20° C., the reaction mixture was diluted with aqueous saturated sodium bicarbonate solution (30 mL) and aqueous saturated sodium carbonate solution (30 mL). The layers were separated and the aqueous layer was extracted with 9:1 chloroform:isopropanol (50 mL). The combined organic layers were washed with brine, dried over sodium sulfate, filtered, and concentrated under reduced pressure to racemic ethyl (1,2-cis)-4-(benzylamino)-2-methylcyclohexanecarboxylate as a 2:1 mixture of diastereomers. MS ESI calcd. for C$_{17}$H$_{26}$NO$_2$ [M+H]$^+$ 276. found 276.

Step 2:

Racemic ethyl (1,2-cis)-4-(benzylamino)-2-methylcyclohexanecarboxylate (3.24 g, 12.40 mmol, 2:1 mixture of diastereomers) and palladium hydroxide on carbon (20 weight %, 0.435 g, 0.620 mmol) in methanol (60 mL) were combined. The vessel was fitted with a hydrogen balloon, and the atmosphere was exchanged for hydrogen via four vacuum hydrogen flush cycles. After 18 hours at 20° C., the reaction mixture was filtered through diatomaceous earth and the resulting clear solution was concentrated to provide racemic ethyl (1,2-cis)-4-amino-2-methylcyclohexanecarboxylate as a 2:1 mixture of diastereomers that was used without further purification. MS ESI calcd. for C$_{10}$H$_{20}$NO$_2$ [M+H]$^+$ 186. found 186.

The intermediate in the following Table was prepared according to the method described for intermediate 37.

| Intermediate | Structure | [M + H]+ Obs'd |
|---|---|---|
| 38 | <br>mixture of 4 diastereomers | 186 |

Intermediate 39

Methyl (1,2-trans, 1,4-trans)-4-[(5-bromopyridin-2-yl)amino]-2-methoxycyclohexanecarboxylate

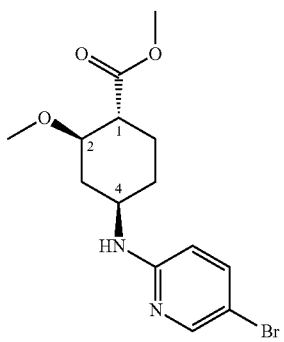 [SMILES: COC(=O)[C@@H]1CC[C@@H](Nc2ccc(Br)cn2)C[C@H]1OC]

Step 1:

Methyl 4-(benzylamino)-2-methoxycyclohexanecarboxylate (1.84 g, 6.63 mmol, racemic mixture of diastereomers) and palladium hydroxide on carbon (20 weight %, 0.233 g, 0.332 mmol) in methanol (35 mL) were combined, and the atmosphere was exchanged for hydrogen (balloon) via four vacuum hydrogen flush cycles. After 24 hours, additional palladium hydroxide on carbon (20 weight %, 0.233 g, 0.332 mmol) was added, and the reaction mixture was again placed under a hydrogen atmosphere. Following another 24 hours, the reaction mixture was filtered through diatomaceous earth and concentrated under reduced pressure to give methyl 4-amino-2-methoxycyclohexanecarboxylate as a racemic mixture of three diastereomers, which was carried forward without further purification. MS ESI calcd. for $C_9H_{18}NO_3$ $[M+H]^+$ 188. found 188.

Step 2:

A suspension of methy 4-amino-2-methoxycyclohexanecarboxylate (1.0 g, 5.34 mmol, racemic mixture of three diastereomers), 5-bromo-2fluoropyridine (2.75 ml, 26.7 mmol), and potassium carbonate (1.476 g, 10.68 mmol) in N,N-dimethylformamide (8 ml) was heated to 130° C. for 7 hours. After allowing to cool to room temperature, the reaction mixture was diluted with diethyl ether (100 mL), ethyl acetate (50 mL), and water (50 mL). The layers were separated, and the organic layer was washed with additional water (2×50 mL) and brine (50 mL), dried over sodium sulfate, filtered, and concentrated under reduced pressure. The residue was purified by chromatography on silica gel (10-30% ethyl acetate/hexanes) to provide the major diastereomer, which was determined to be racemic methyl (1,2-trans, 1,4-trans)-4-[(5-bromopyridin-2-yl)amino]-2-methoxycyclohexanecarboxylate. MS ESI calcd. for $C_{14}H_{20}BrN_2O_3$ $[M+H]^+$ 343 and 345. found 343 and 345. $^1H$ NMR (500 MHz, $CDCl_3$) δ 8.09 (d, J=2.4 Hz, 1H), 7.45 (dd, J=2.5, 8.8 Hz, 1H), 6.26 (d, J=8.8 Hz, 1H), 4.50-4.46 (m, 1H), 3.72 (s, 3H), 3.57 (m, 1H), 3.35 (s, 3H), 2.57-2.48 (m, 1H), 2.45-2.34 (m, 1H), 2.12-2.03 (m, 1H), 2.02-1.93 (m, 1H), 1.67-1.60 (m, 1H), 1.24-1.10 (m, 2H).

Intermediate 40

[3-(1H-Pyrazol-4-yl)phenyl]acetic acid

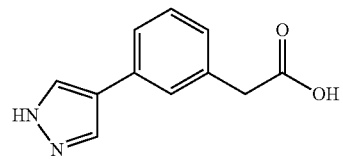 [SMILES: O=C(O)Cc1cccc(-c2cn[nH]c2)c1]

Step 1:

A mixture of 4-bromo-1-(tetrahydro-2H-pyran-2-yl)-1H-pyrazole (5 g, 21.6 mmol), ethyl [3-(4,4,5,5-tetramethyl-1,3,2-dioxaborolan-2-yl)phenyl]acetate (6.5 g, 22.7 mmol), sodium carbonate (7 g, 64.8 mmol) and [1,1-bis(diphenylphosphino)ferrocene]dichloropalladium(II) (0.513 g, 0.648 mmol) in dioxane (60 mL) and water (30 mL) was stirred at 80° C. for 14 hours. After allowing to cool to room temperature, ethyl acetate and water were added to the mixture, and the resultant mixture was filtered. The organic layer was separated, washed with brine, dried over $Na_2SO_4$, and concentrated under reduced pressure. The residue was purified by silica gel column chromatography to afford ethyl {3-[1-(tetrahydro-2H-pyran-2-yl)-1H-pyrazol-4-yl]phenyl}acetate as an oil.

Step 2:

A mixture of ethyl {3-[1-(tetrahydro-2H-pyran-2-yl)-1H-pyrazol-4-yl]phenyl}acetate (160 g, 0.50 mol) in MeOH/HCl (800 mL) was stirred at room temperature for 3 hours. The mixture was concentrated under reduced pressure and washed with $Et_2O$ (300 mL) to afford ethyl [3-(1H-pyrazol-4-yl)phenyl]acetate as a solid.

Step 3:

NaOH (57 g, 1.43 mol) was added to a solution of ethyl [3-(1H-pyrazol-4-yl)phenyl]acetate (110 g, 0.478 mol) in $H_2O$/THF/MeOH (250 mL/250 mL/250 mL). The mixture was stirred at room temperature for 3 hours. The mixture was concentrated in vacuo and the pH was adjusted to 3 to 4 via the addition of 3 M HCl, The solid was collected via filtration and dried to afford [3-(1H-pyrazol-4-yl)phenyl]acetic acid. MS ESI calcd. for $C_{11}H_{11}N_2O_2$ $[M+H]^+$ 203. found 203. $^1H$-NMR (500 MHz, DMSO-$d_6$) δ: 7.94 (s, 2H), 7.41-7.24 (m, 2H), 7.13 (t, J=7.6 Hz, 1H), 6.99 (d, J=7.6 Hz, 1H), 3.13 (s, 2H).

Intermediate 41

Ethyl (1,2-cis)-4-formyl-2-methylcyclohexanecarboxylate

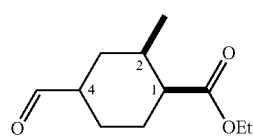

To a solution of (methoxymethyl)triphenylphosphonium chloride (67.8 g, 0.2 mol) in tetrahydrofuran (700 mL) was added sodium hydride (60% dispersion in mineral oil, 7.1 g, 0.18 mol) in several portions at 0° C. After the resulting mixture was stirred at 0° C. for 1 hour, racemic ethyl (1,2-cis)-2-methyl-4-oxocyclohexanecarboxylate (20.0 g, 0.11 mol) in tetrahydrofuran (40 mL) was added dropwise at 0° C. The reaction mixture was stirred at room temperature for 14 hours and then cooled back to 0° C. Water (500 mL) was added dropwise. The resulting mixture was extracted with ethyl acetate (3×300 mL), and the combined organic layers were washed with brine, dried over sodium sulfate, filtered, and concentrated under reduced pressure. The residue was purified by column chromatography on silica gel (petroleum ether:ethyl acetate=50:1) to give racemic ethyl (1,2-cis)-4-(methoxymethylidene)-2-methylcyclohexanecarboxylate. This material was dissolved in tetrahydrofuran (150 mL) and a solution of hydrochloric acid (6 M in water, 35 mL, 0.21 mol) was added dropwise at 0° C. After being stirred for 2 hours at room temperature, the reaction mixture was extracted with ethyl acetate (3×300 mL). The combined organic layers were washed with brine, dried over sodium sulfate, filtered, and concentrated under reduced pressure to afford racemic ethyl (1,2-cis)-4-formyl-2-methylcyclohexanecarboxylate. $^1$H NMR (400 MHz, CDCl$_3$) δ 9.62-9.60 (m, 1H), 4.14-4.10 (m, 2H), 2.46-2.41 (m, 2H), 2.08-2.00 (m, 2H), 1.84-1.70 (m, 4H), 1.61-1.55 (m, 1H), 1.27-1.23 (m, 3H), 1.02-0.91 (m, 3H).

Intermediate 42

Ethyl (1,2-cis)-4-[(5-bromopyridin-2-yl)carbonyl]-2-methylcyclohexanecarboxylate

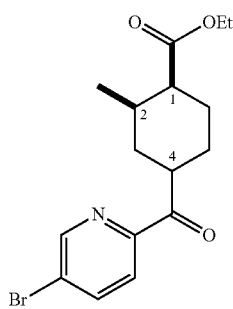 [SMILES: CCOC(=O)[C@H]1CCC(C(=O)c2ccc(Br)cn2)C[C@H]1C]

To a solution of racemic ethyl (1,2-cis)-4-[(5-bromopyridin-2-yl)(hydroxy)methyl]-2-methylcyclohexanecarboxylate (5 g, 14.1 mmol) in 100 mL dichloromethane at 0° C. was added Dess-Martin periodinane (6.6 g, 15.5 mol) in several portions. The reaction mixture was stirred at room temperature for 1 hour and then diluted with saturated aqueous sodium bicarbonate solution (40 mL). The layers were separated, and the organic layer was concentrated under reduced pressure. The residue was purified by column chromatography on silica gel (petroleum ether:ethyl acetate=10:1) to afford racemic ethyl rac-(1,2-cis)-4-[(5-bromopyridin-2-yl)carbonyl]-2-methylcyclohexanecarboxylate as a mixture of four diastereomers. MS ESI calcd. for C$_{16}$H$_{21}$BrNO$_3$ [M+H]$^+$ 354 and 356. found 354 and 356. $^1$H NMR (400 MHz, CDCl$_3$) δ 8.73-8.71 (m, 1H), 7.97-7.89 (m, 2H), 4.15-4.10 (m, 2H), 3.83-3.77 (m, 1H), 2.66 (s, 1H), 2.12-2.19 (m, 1H), 1.89-1.66 (m, 6H), 1.28-1.25 (m, 3H), 1.05-0.95 (m, 3H).

Intermediate 43

Methyl trans-4-[1-(5-bromopyridin-2-yl)-1-methoxyethyl]cyclohexanecarboxylate

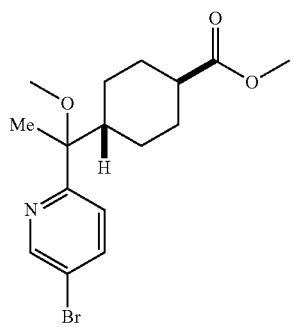 [SMILES: COC(=O)[C@H]1CC[C@H](C(C)(OC)c2ccc(Br)cn2)CC1]

Racemic methyl trans-4-[1-(5-bromopyridin-2-yl)hydroxyethyl]cyclohexanecarboxylate (500 mg, 1.461 mmol) was dissolved in DMF (7.3 mL) and cooled to 0° C. Sodium hydride (60 wt %, 117 mg, 2.92 mmol) was added in one portion. The mixture was stirred and allowed to warm to room temperature. After 20 minutes, methyl iodide (0.183 mL, 2.92 mmol) was added, and the reaction was stirred at room temperature for 30 minutes. The mixture was diluted with water, ethyl acetate, and brine. The layers were separated, and the organic portion dried over magnesium sulfate, filtered, and concentrated in vacuo. Purification via silica gel column chromatography (20% EtOAc:hexanes) gave racemic methyl trans-4-[1-(5-bromopyridin-2-yl)-1-methoxyethyl]cyclohexanecarboxylate as a colorless oil. MS ESI calcd. for C$_{16}$H$_{23}$BrNO$_3$ [M+H]$^+$ 356 and 358. found 356 and 358. $^1$H NMR (500 MHz, DMSO-d$_6$) 8.64 (d, J=2.2 Hz, 1H), 8.01 (dd, J=2.3, 8.5 Hz, 1H), 7.37 (d, J=9.1 Hz, 1H), 3.54 (s, 3H), 2.98 (s, 3H), 2.20-1.50 (m, 5H), 1.55 (s, 3H), 1.40-0.75 (m, 5H).

Intermediate 44

Methyl trans-4-{(1R or 1S)-1-hydroxy-1-[5-(4,4,5,5-tetramethyl-1,3,2-dioxaborolan-2-yl)pyridin-2-yl]ethyl}cyclohexanecarboxylate

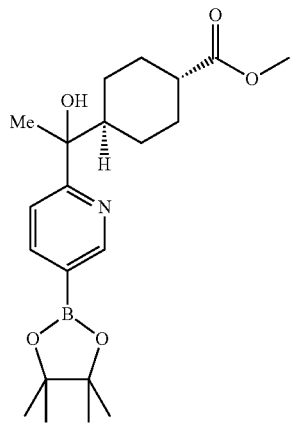

Methyl trans-4-[(1R or 1S)-1-(5-bromopyridin-2-yl)-1-hydroxyethyl]cyclohexanecarboxylate (200 mg, 0.555 mmol), bis(pinacolato)diboron (162 mg, 0.638 mmol), 2-dicyclohexylphosphino-2',4',6'-triisopropylbiphenyl (27 mg, 0.057 mmol), tris(dibenzylideneacetone)dipalladium(0) (25 mg, 0.027 mmol), and dioxane (2.22 mL) were combined in a sealed vial and heated to a temperature of 90° C. for 1 hour with stirring. The reaction mixture was subsequently allowed to cool to room temperature and filtered over CELITE. The filtrate was diluted with ethyl acetate and washed successively with water and brine. The organic fraction was dried over sodium sulfate, filtered, and concentrated to afford crude methyl trans-4-{(1R or 1S)-1-hydroxy-1-[5-(4,4,5,5-tetramethyl-1,3,2-dioxaborolan-2-yl)pyridin-2-yl]ethyl}cyclohexanecarboxylate as an orange oil, which was used in the subsequent synthetic transformation without further purification. MS ESI calcd. for $C_{15}H_{23}BNO_5$ $[M—C_6H_{10}+H]^+$ 308. found 308.

Example 1 trans-4-((1R or 1S)-1-Hydroxy-1-(4-methyl-6-(4-(trifluoromethyl)pyridin-2-ylamino)-2,3'-bipyridin-6'-yl)ethyl)cyclohexanecarboxylic acid

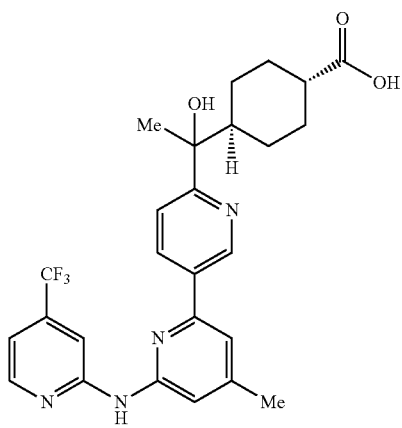 [SMILES: Cc1cc(Nc2cc(C(F)(F)F)ccn2)nc(-c2ccc(C(C)(O)[C@H]3CC[C@H](C(=O)O)CC3)nc2)c1]

Step 1:
6-Bromo-4-methyl-N-(4-(trifluoromethyl)pyridin-2-yl)pyridin-2-amine (97 mg, 0.291 mmol), crude methyl trans-4-{(1R or 1S)-1-hydroxy-1-[5-(4,4,5,5-tetramethyl-1,3,2-dioxaborolan-2-yl)pyridin-2-yl]ethyl}cyclohexanecarboxylate (108 mg, 0.277 mmol), [1,1-bis(diphenylphosphino)ferrocene]dichloropalladium(II) (20 mg, 0.027 mmol), dioxane (600 μL) and potassium carbonate (2M in water, 350 μL, 0.700 mmol) were placed in a sealed vial and heated to a temperature of 100° C. for 2 hours with stirring. The mixture was subsequently allowed to cool to room temperature and loaded directly onto a silica samplet. Purification by chromatography on silica gel, (EtOAc/isohexane 7-100%) afforded methyl trans-4-[(1R or 1S)-1-hydroxy-1-(4-methyl-6-{[4-(trifluoromethyl)pyridin-2-yl]amino}-2,3'-bipyridin-6'-yl)ethyl]cyclohexanecarboxylate as a nearly colorless oil. MS ESI calcd. for $C_{27}H_{30}F_3N_4O_3$ $[M+H]^+$ 515. found 515.

Step 2:
To a solution of methyl trans-4-[(1R or 1S)-1-hydroxy-1-(4-methyl-6-{[4-(trifluoromethyl)pyridin-2-yl]amino}-2,3'-bipyridin-6'-yl)ethyl]cyclohexanecarboxylate (83 mg, 0.161 mmol) in methanol (1.5 ml) was added sodium hydroxide (1.0 M in water, 560 μl, 0.560 mmol). The mixture was then heated to a temperature of 80° C. for 60 minutes. The reaction was subsequently allowed to cool to room temperature and the pH was lowered to 5-6 by dropwise addition of hydrochloric acid (2N in water). The resulting suspension was filtered to afford trans-4-((1R or 1S)-1-hydroxy-1-(4-methyl-6-(4-(trifluoromethyl)pyridin-2-ylamino)-2,3'-bipyridin-6'-yl)ethyl)cyclohexanecarboxylic acid (52 mg, 0.104 mmol, 64.4% yield) as a colorless solid. MS ESI calcd. for $C_{26}H_{28}F_3N_4O_3$ $[M+H]^+$ 501. found 501. $^1$H NMR (500 MHz, DMSO-$d_6$) δ 11.94 (br s, 1H), 10.21 (s, 1H), 9.12 (s, 1H), 8.58 (s, 1H), 8.49 (d, J=5.1 Hz, 1H), 8.33 (d, J=8.3 Hz, 1H), 7.68 (d, J=8.3 Hz, 1H), 7.45 (s, 1H), 7.29 (s, 1H), 7.20 (d, J=5.1 Hz, 1H), 5.05 (s, 1H), 2.35 (s, 3H), 2.05-1.66 (m, 5H), 1.43 (s, 3H), 1.15-1.0 (m, 5H). rhSyk IC$_{50}$=<0.5 nM The following compounds were prepared according to the method described for Example 1, step 1, and where appropriate, step 2 as well.

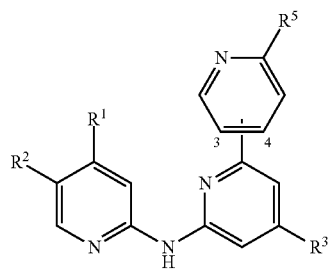

(attachment is on the 3-carbon except where marked with *, in which case attachment is on the 4-carbon)

| Ex. | $R^1/R^2$ | $R^3$ | $R^5$ | IC50 (nM) | [M + H]+ Obs'd |
|---|---|---|---|---|---|
| 1-1 | CF$_3$/H | CH$_3$ | F | 38 | 349 |
| 1-2 | CH$_3$/H | CH$_3$ | F | 111 | 295 |
| 1-3* | CH$_3$/H | CH$_3$ | F | 135 | 295 |
| 1-4* | CF$_3$/H | CH$_3$ | F | 87 | 349 |
| 1-5 | CF$_3$/H | CH$_3$ | 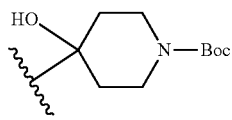 [SMILES: *C1(O)CCN(C(=O)OC(C)(C)C)CC1] | 406 | 530 |

-continued

| Ex. | R¹/R² | R³ | R⁵ | IC50 (nM) | [M + H]+ Obs'd |
|---|---|---|---|---|---|
| 1-6 | CF₃/H | CH₃ | 4-hydroxy-3,3-dimethyl-cyclohexyl-CO₂CH₃ (anti, enantiomer 1) | 405 | 515 |
| 1-7 | CF₃/H | CH₃ | 4-hydroxy-3,3-dimethyl-cyclohexyl-CO₂CH₃ (anti, enantiomer 2) | 245 | 515 |
| 1-8 | CH₃/H | H | O-benzyl | ** | 369 |
| 1-9 | CF₃/H | CH₃ | 4-hydroxy-3,3-dimethyl-cyclohexyl-CO₂CH₃ (syn, enantiomer 1) | 100 | 515 |
| 1-10 | CF₃/H | CH₃ | 4-hydroxy-cyclohexyl-CO₂Et (syn) | 45 | 501 |
| 1-11 | CF₃/H | CH₃ | 4-hydroxy-cyclohexyl-CO₂Et (anti) | 47 | 501 |
| 1-12 | CF₃/H | CH₃ | 4-(CO₂CH₃)-cyclohexyl-carbonyl (trans) | 643 | 499 |
| 1-13 | CHF₂/H | CH₃ | 1-hydroxy-cyclobutyl | 5 | 383 |
| 1-14 | CHF₂/H | CH₃ | —C(OH)(CH₃)₂ | 8 | 371 |
| 1-15 | CF₃/H | CH₃ | H₃C,OH-C(*)-cyclohexyl-CO₂nBu (* = R or S) (trans) | 19 | 557 |

-continued
| Ex. | $R^1/R^2$ | $R^3$ | $R^5$ | IC50 (nM) | [M + H]+ Obs'd |
|---|---|---|---|---|---|
| 1-16 | CF$_3$/H | CH$_3$ | 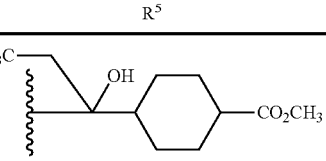<br>(trans, racemic) | 12 | 529 |
| 1-17 | CF$_3$/H | CH$_3$ | 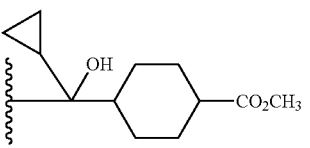<br>(trans, racemic) | 16 | 541 |
| 1-18 | CF$_3$/H | CH$_3$ | 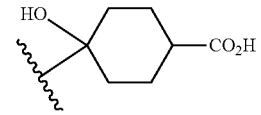<br>(syn) | 1 | 473 |
| 1-19 | CF$_3$/H | CH$_3$ | 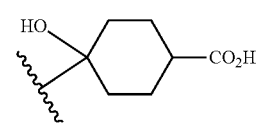 [SMILES: *C1(O)CCC(C(=O)O)CC1]<br>(anti) | 3 | 473 |
| 1-20 | CF$_3$/H | CH$_3$ | 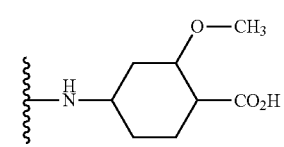 [SMILES: *NC1CCC(C(=O)O)C(OC)C1]<br>(racemic) | <0.5 | 502 |
| 1-21 | CF$_3$/H | CH$_3$ | 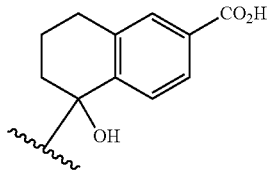 [SMILES: *C1(O)CCCc2cc(C(=O)O)ccc21]<br>(enantiomer 1) | 2 | 521 |
| 1-22 | CF$_3$/H | CH$_3$ | 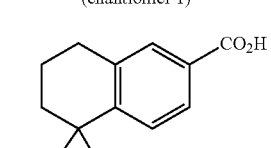<br>(enantiomer 2) | 1 | 521 |
| 1-23 | CF$_3$/H | CH$_3$ | 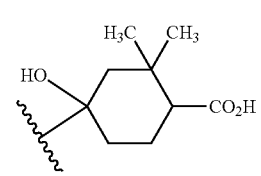 [SMILES: *C1(O)CCC(C(=O)O)C(C)(C)C1]<br>(anti, enantiomer 1) | 29 | 501 |

-continued

| Ex. | R¹/R² | R³ | R⁵ | IC50 (nM) | [M + H]+ Obs'd |
|---|---|---|---|---|---|
| 1-24 | CF₃/H | CH₃ | (anti, enantiomer 2) | 8 | 501 |
| 1-25 | CF₃/H | CH₃ | (syn, enantiomer 1) | 1 | 501 |
| 1-26 | CF₃/H | CH₃ | (syn, enantiomer 2) | 1 | 501 |
| 1-27 | CH₃/F | CH₃ | (* = R or S) (trans) | 1 | 465 |
| 1-28 | CH₃/H | CH₃ | (* = R or S) (trans) | 1 | 447 |
| 1-29 | OCH₃/H | CH₃ | (* = R or S) (trans) | 1 | 463 |
| 1-30 | CF₃/H | CH₃ | (trans, racemic) | <0.5 | 515 |
| 1-31 | CF₃/H | CH₃ | (trans, racemic) | <0.5 | 527 |

-continued

| Ex. | R¹/R² | R³ | R⁵ | IC50 (nM) | [M + H]+ Obs'd |
|---|---|---|---|---|---|
| 1-32 | c-Pr/H | $CH_3$ | H₃C, OH group with cyclohexyl-$CO_2H$ (* = R or S) (trans) | 1 | 473 |
| 1-33 | $CHF_2$/H | cPr | H₃C, OH group with cyclohexyl-$CO_2H$ (* = R or S) (trans) | <0.5 | 509 |
| 1-34 | $CHF_2$/H | $C(CH_3)_2OH$ | H₃C, OH group with cyclohexyl-$CO_2H$ (* = R or S) (trans) | 1 | 527 |
| 1-35 | $CHF_2$/H | $CH_3$ | H₃C, OH group with 2-$CH_3$-cyclohexyl-$CO_2H$ (1,2-cis, mixture of 8 diastereomers) | <0.5 | 497 |
| 1-36 | $CHF_2$/H | $CH_3$ | H₃CO, $CH_3$ group with cyclohexyl-$CO_2H$ (racemic, trans) | 1 | 497 |

** 58% inhibition at 10 uM

Example 2

3-[(4-Amino-6-{[4-(trifluoromethyl)pyridin-2-yl]amino}-2,3'-bipyridin-6'-yl)amino]pyrrolidin-2-one

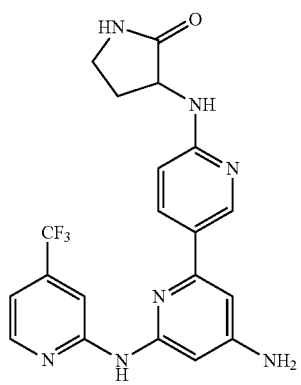 [SMILES: Nc1cc(Nc2cc(C(F)(F)F)ccn2)nc(-c2ccc(NC3CCNC3=O)nc2)c1]

6'-Fluoro-$N^6$-[4-(trifluoromethyl)pyridin-2-yl]-2,3'-bipyridine-4,6-diamine (50 mg, 0.143 mmol), 3-aminopyrrolidin-2-one (39.1 mg, 0.286 mmol), tribasic potassium phosphate (60.8 mg, 0.286 mmol), and N,N-diisopropylethylamine (0.050 ml, 0.286 mmol) were dissolved in dimethylsulfoxide (0.5 mL). The mixture was heated to 130° C. with stirring for three days. After allowing to cool to room temperature, the reaction mixture was partitioned between ethyl acetate (30 mL) and saturated aqueous sodium bicarbonate solution (15 mL). The layers were separated, and the organic layer was washed with water (3×5 mL) and brine (10 mL), dried over sodium sulfate, filtered, and concentrated under reduced pressure. The crude residue was purified using reverse phase HPLC (15 to 85% acetonitrile/water with 0.1% TFA gradient). The fractions containing the product were partitioned between 10% isopropanol/chloroform and 1:1 saturated aqueous sodium bicarbonate solution:brine. The layers were separated, and the aqueous layer was extracted with additional 10% isopropanol/chloroform. The combined organic layers were dried over sodium sulfate, filtered, and concentrated under reduced pressure to afford 3-[(4-amino-6-{[4-(trifluoromethyl)pyridin-2-yl]amino}-2,3'-bipyridin-6'-yl)amino]pyrrolidin-2-one. MS ESI calcd. for $C_{20}H_{19}F_3N_7O$ $[M+H]^+$ 430. found 430. $^1$H NMR (500 MHz, DMSO-$d_6$) δ 9.74 (s, 1H), 8.62 (s, 1H), 8.50 (d, J=2.2 Hz, 1H), 8.40 (d, J=5.1 Hz, 1H), 7.88 (dd, J=2.4, 8.8 Hz, 1H), 7.83 (s, 1H), 7.08 (d, J=5.3 Hz, 1H), 6.94 (d, J=7.3 Hz, 1H), 6.61 (d, J=8.8 Hz, 1H), 6.53 (d, J=1.6 Hz, 1H), 6.46 (s, 1H), 5.97 (s, 2H), 4.60-4.52 (m, 1H), 3.25-3.20 (m, 2H), 2.52-2.46 (m, 1H), 1.87-1.79 (m, 1H). rhSyk $IC_{50}$=4 nM.

The following compounds were prepared according to the method described for Example 2.

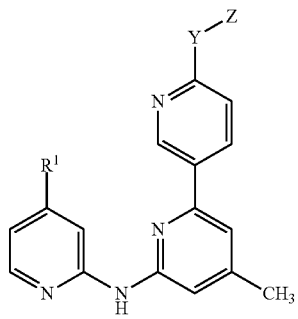
| Ex. | R¹ | Y—Z | IC50 (nM) | [M + H]+ Obs'd |
|---|---|---|---|---|
| 2-1 | CF$_3$ | piperazine-C(O)-indole | 61 | 558 |
| 2-2 | CF$_3$ | 1-methyl-3-(NHBoc)piperidine | 271 | 529 |
| 2-3 | CF$_3$ | 3-(NHBoc)pyrrolidine | 248 | 515 |
| 2-4 | CF$_3$ | NH-(1-Boc-piperidin-4-yl) | 91 | 529 |
| 2-5 | CH$_3$ | NH-(2-oxopyrrolidin-3-yl) (racemic) | 27 | 375 |
| 2-6 | CH$_3$ | 2-(CO$_2$H)pyrrolidine (racemic) | 45 | 390 |
| 2-7 | CH$_3$ | 2-(CO$_2$H)azetidine (racemic) | 43 | 376 |

-continued
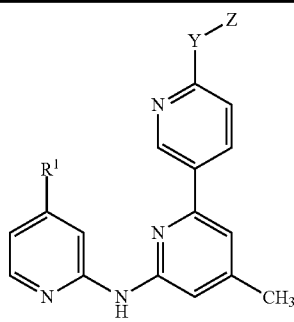
| Ex. | R¹ | Y—Z | IC50 (nM) | [M + H]+ Obs'd |
|---|---|---|---|---|
| 2-8 | CH₃ | —NHC(CH₃)₂CO₂H | 16 | 378 |
| 2-9 | CF₃ | 3-(2-oxopyrrolidinyl)amino (racemic) | 4 | 429 |
| 2-10 | CF₃ | 2-carboxypyrrolidin-1-yl (racemic) | 3 | 444 |
| 2-11 | CF₃ | 2-carboxyazetidin-1-yl (racemic) | 3 | 430 |
| 2-12 | CF₃ | —NHC(CH₃)₂CO₂H | 1 | 432 |
| 2-13 | CH₃ | 2-carboxypyrrolidin-1-yl (racemic) | 226 | 390 |
| 2-14 | CH₃ | 2-carboxyazetidin-1-yl (racemic) | 234 | 376 |
| 2-15 | CH₃ | —NHC(CH₃)₂CO₂H | 298 | 378 |
| 2-16 | CF₃ | 3-(2-oxopyrrolidinyl)amino (racemic) | 6 | 429 |

-continued

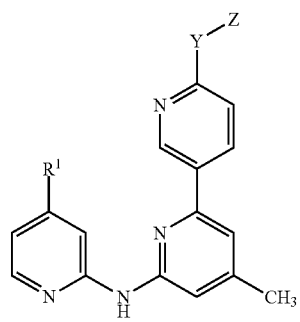

| Ex. | R¹ | Y—Z | IC50 (nM) | [M + H]+ Obs'd |
|---|---|---|---|---|
| 2-17 | $CF_3$ | (pyrrolidine-2-carboxylic acid, N-linked, racemic) | 39 | 444 |
| 2-18 | $CF_3$ | (azetidine-2-carboxylic acid, N-linked, racemic) | 33 | 430 |
| 2-19 | $CF_3$ | —NHC(CH₃)₂CO₂H | 19 | 432 |
| 2-20 | $CF_3$ | (piperazine-N-carbonyl-piperidine-3-carboxylic acid, racemic) | 2 | 570 |
| 2-21 | $CF_3$ | (N-azetidinyl-cyclohexane-3-carboxylic acid) | 2 | 512 |
| 2-22 | $CF_3$ | (N-azetidinyl-cyclohexane-4-carboxylic acid) | 3 | 512 |
| 2-23 | $CF_3$ | (—NH—CH₂-cyclohexane-CO₂H) | 3 | 486 |
| 2-24 | $CF_3$ | (—NH-cyclohexane-CO₂H, trans) | 1 | 472 |

-continued
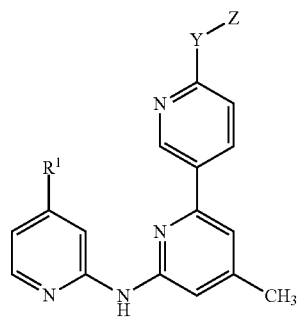
| Ex. | R¹ | Y—Z | IC50 (nM) | [M + H]+ Obs'd |
|---|---|---|---|---|
| 2-25 | $CF_3$ | HN-cyclohexyl-$CO_2H$ (cis) | 7 | 472 |
| 2-26 | $CF_3$ | N-piperidinyl-C(O)-N-piperidinyl-$CO_2H$ | 3 | 569 |
| 2-27 | $CF_3$ | (R)-piperidinyl-C(O)-(S)-piperidinyl-$CO_2H$ | 2 | 569 |
| 2-28 | $CF_3$ | (R)-piperidinyl-C(O)-(R)-piperidinyl-$CO_2H$ | 3 | 569 |
| 2-29 | $CF_3$ | decahydroisoquinolinyl-$CO_2H$ (racemic) | 6 | 512 |
| 2-30 | $CF_3$ | morpholinyl | 14 | 416.2 |
| 2-31 | $CF_3$ | 5-oxopyrrolidinyl-$CO_2H$ (racemic) | 1 | 541 |

Example 3 trans-4-{[(4-Methyl-6-{[4-(trifluoromethyl)pyridin-2-yl]amino}-2,3'-bipyridin-6'-yl)oxy]methyl}cyclohexanecarboxylic acid

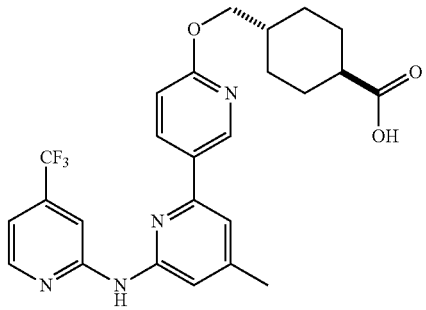

A flask was charged with potassium carbonate (0.028 g, 0.200 mmol), methyl trans-4-(hydroxymethyl)cyclohexanecarboxylate (0.034 g, 0.200 mmol), 6'-fluoro-4-methyl-N-[4-(trifluoromethyl)pyridin-2-yl]-2,3'-bipyridin-6-amine (0.032 g, 0.1 mmol), NMP (1 mL), and DIEA (0.035 mL, 0.20 mmol). The vial was sealed and heated to 130° C. for 72 hours. Aqueous NaOH (1M, 0.5 mL) was added, and the vial was heated in a microwave for 10 minutes at 110° C. The mixture was filtered through a CELITE cartridge, washing with NMP (3 mL). The residue, dissolved in 3 mL of NMP, was purified by mass triggered reverse phase HPLC (21-55% Acetonitrile/Water with a 0.1% Ammonium Hydroxide modifier on a Waters X-Bridge C18 19 mm×100 mm) to yield trans-4-{[(4-methyl-6-{[4-(trifluoromethyl)pyridin-2-yl]amino}-2,3'-bipyridin-6'-yl)oxy]methyl}cyclohexanecarboxylic acid. MS ESI calcd. for $C_{25}H_{26}F_3N_4O_3$ $[M+H]^+$ 487. found 487. rhSyk $IC_{50}$=3 nM.

The following compounds were prepared using the method described for Example 2, followed by the method described for Example 3.

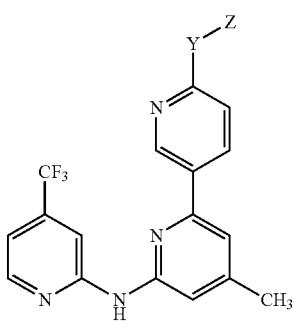

| Ex. | Y—Z | IC50 (nM) | [M + H]+ Obs'd |
|---|---|---|---|
| 3-1 | piperidine-cyclohexane-CO₂H (1R,2S) | 3 | 540 |
| 3-2 | NH-cyclohexane(2-CH₃)-CO₂H (1,2-cis) | <0.5 | 486 |
| 3-3 | NH-cyclohexane(2-CH₃)-CO₂H (1,2-cis) | 1 | 486 |
| 3-4 | NH-cyclohexane(2,2-diCH₃)-CO₂H (racemic, mixture of diastereomers) | <0.5 | 500 |
| 3-5 | NH-cyclohexane(2,2-diCH₃)-CO₂H (racemic, mixture of diastereomers) | 2 | 500 |

Example 4

(6-Fluoroquinolin-3-yl)(4-(4-methyl-6-(4-(trifluoromethyl)pyridin-2-ylamino)-2,3'-bipyridin-6'-ylamino)piperidin-1-yl)methanone

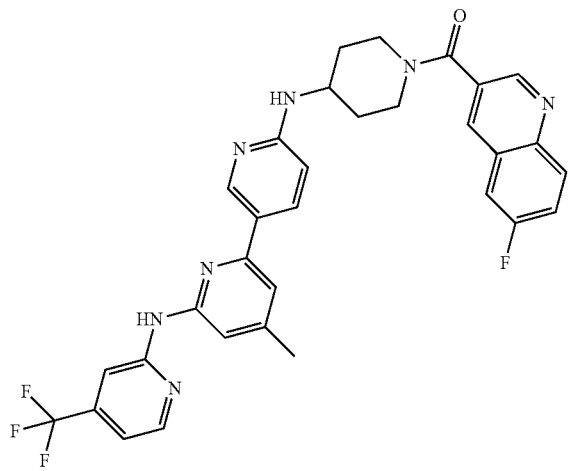 [SMILES: Cc1cc(Nc2cc(C(F)(F)F)ccn2)nc(-c2ccc(NC3CCN(C(=O)c4cnc5ccc(F)cc5c4)CC3)nc2)c1]

4-Methyl-N6'-(piperidin-4-yl)-N6-(4-(trifluoromethyl)pyridin-2-yl)-2,3'-bipyridine-6,6'-diamine (30 mg, 0.07 mmol) was dissolved in DMF (500 µL). The solution was then treated with DIEA (24 µL, 0.14 mmol), 6-fluoroquinoline-3-carboxylic acid (20 mg. 0.11 mmol), and 2,4,6-tripropyl-1,3,5,2,4,6-trioxatriphosphorinane-2,4,6-trioxide (42 µL, 0.07 mmol). The reaction was warmed to 40° C. and stirred for 16 hours. The reaction was allowed to cool to room temperature: The mixture was diluted with DMSO (1.0 mL) and purified by mass-triggered reverse phase high pressure liquid chromatography, eluting with a 1% ammonium hydroxide buffered water/acetonitrile gradient over a Waters X-Bridge C-18 column, to afford (6-fluoroquinolin-3-yl)(4-(4-methyl-6-(4-(trifluoromethyl)pyridin-2-ylamino)-2,3'-bipyridin-6'-ylamino)piperidin-1-yl)methanone. MS ESI calcd. for $C_{32}H_{28}F_4N_7O$ $[M+H]^+$ 602. found 602. $^1$H NMR (600 MHz, DMSO-$d_6$) δ 10.05 (s, 1H), 8.87 (d, J=2.0 Hz, 1H), 8.66 (d, J=2.1 Hz, 1H), 8.60 (s, 1H), 8.44 (d, J=5.2 Hz, 1H), 8.42 (d, J=1.8 Hz, 1H), 8.11 (dd, J=5.4, 9.2 Hz, 1H), 8.00 (dd, J=2.4, 8.8 Hz, 1H), 7.86 (dd, J=2.9, 9.3 Hz, 1H), 7.73 (m, 1H), 7.20 (s, 1H), 7.14 (d, J=5.1 Hz, 1H), 7.07 (s, 1H), 6.87 (d, J=7.6 Hz, 1H), 6.56 (d, J=8.8 Hz, 1H), 4.37 (s, 1H), 4.06 (s, 1H), 3.32 (s, 1H), 2.47-2.45 (m, 1H), 2.27 (s, 3H), 2.04 (s, 1H), 1.90 (s, 1H), 1.49 (s, 1H), 1.42 (s, 2H). rhSyk $IC_{50}$=8 nM.

The following compounds were prepared according to the method described for Example 4:

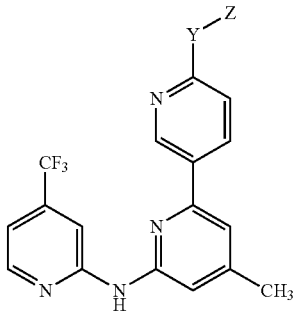

| Ex. | Y—Z | IC50 (nM) | [M + H]+ Obs'd |
|---|---|---|---|
| 4-1 | ![structure] | 9 | 613 |
| 4-2 | ![structure] | 1 | 600 |

-continued

[Core structure: 4-(trifluoromethyl)pyridin-2-yl amino linked to a methylpyridine bearing a pyridyl-Y-Z substituent]

| Ex. | Y—Z | IC50 (nM) | [M + H]+ Obs'd |
|---|---|---|---|
| 4-3 | piperidin-4-ylamino-N-acyl-CH2-(1H-indazol-6-yl) | 8 | 587 |
| 4-4 | piperidin-4-ylamino-N-acyl-(3-oxoisoindolin-5-yl) | 1 | 588 |
| 4-5 | piperidin-4-ylamino-N-acyl-(1-oxoisoindolin-5-yl) | 2 | 588 |
| 4-6 | piperidin-4-ylamino-N-acyl-(3-methyl-1H-indol-2-yl) | 22 | 586 |
| 4-7 | piperidin-4-ylamino-N-acyl-(3-methyl-1H-indol-5-yl) | 10 | 586 |
| 4-8 | piperidin-4-ylamino-N-acyl-CH2-(1H-indazol-3-yl) | 7 | 587 |
| 4-9 | piperidin-4-ylamino-N-acyl-[3-(1H-pyrazol-4-yl)phenyl] | 12 | 599 |

-continued
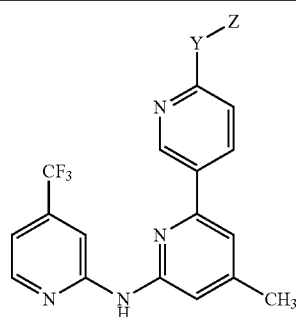
| Ex. | Y—Z | IC50 (nM) | [M + H]+ Obs'd |
|---|---|---|---|
| 4-10 | 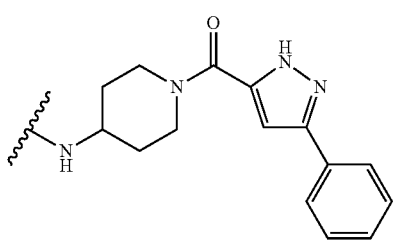 [SMILES: *NC1CCN(C(=O)c2cc(-c3ccccc3)n[nH]2)CC1] | 14 | 599 |
| 4-11 | 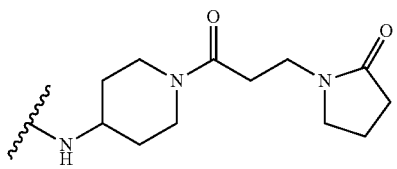 [SMILES: *NC1CCN(C(=O)CCN2CCCC2=O)CC1] | 2 | 568 |
| 4-12 | 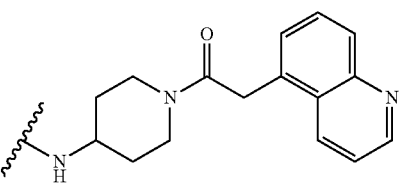 [SMILES: *NC1CCN(C(=O)Cc2cccc3ncccc23)CC1] | 4 | 598 |
| 4-13 | 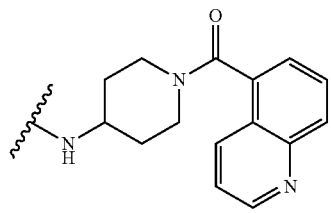 [SMILES: *NC1CCN(C(=O)c2cccc3ncccc23)CC1] | 9 | 584 |
| 4-14 | 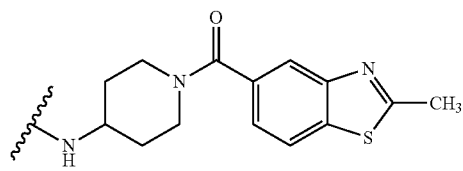 [SMILES: *NC1CCN(C(=O)c2ccc3sc(C)nc3c2)CC1] | 6 | 604 |
| 4-15 | 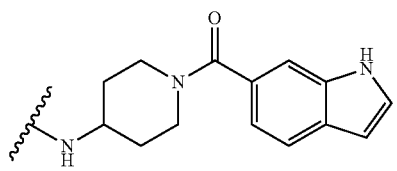 [SMILES: *NC1CCN(C(=O)c2ccc3cc[nH]c3c2)CC1] | 7 | 572 |

-continued
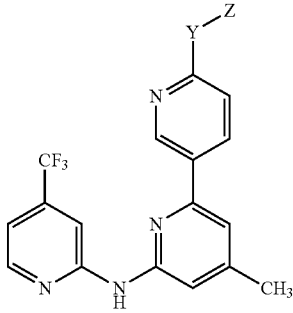
| Ex. | Y—Z | IC50 (nM) | [M + H]+ Obs'd |
|---|---|---|---|
| 4-16 | 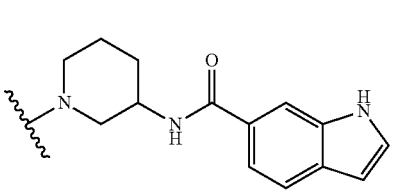 [SMILES: *N1CCCC(NC(=O)c2ccc3cc[nH]c3c2)C1] | 4 | 471 |
| 4-17 | 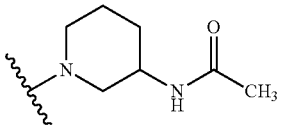 [SMILES: *N1CCCC(NC(C)=O)C1] | 32 | 572 |
| 4-18 | 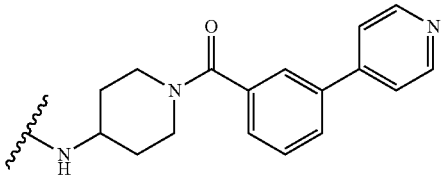 [SMILES: *NC1CCN(C(=O)c2cccc(-c3ccncc3)c2)CC1] | 14 | 471 |
| 4-19 | 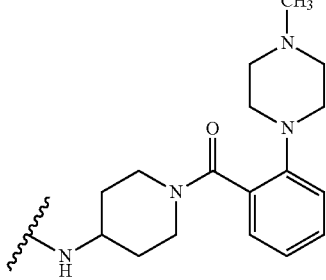 | 12 | 610 |
| 4-20 | 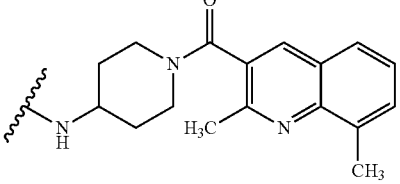 | 4 | 631 |
| 4-21 |  | 89 | 612 |

-continued
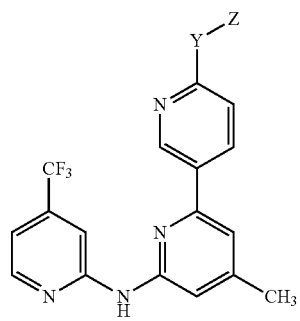
| Ex. | Y—Z | IC50 (nM) | [M + H]+ Obs'd |
|---|---|---|---|
| 4-22 | | 3 | 614 |
| 4-23 | | 3 | 576 |
| 4-24 | | 7 | 584 |
| 4-25 | | 209 | 639 |
| 4-26 | | 7 | 614 |
| 4-27 | | 3 | 576 |

-continued
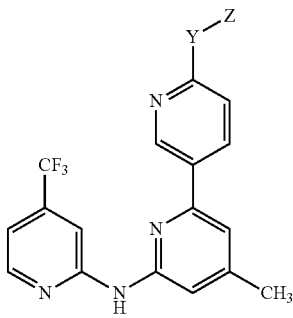
| Ex. | Y—Z | IC50 (nM) | [M + H]+ Obs'd |
|---|---|---|---|
| 4-28 | 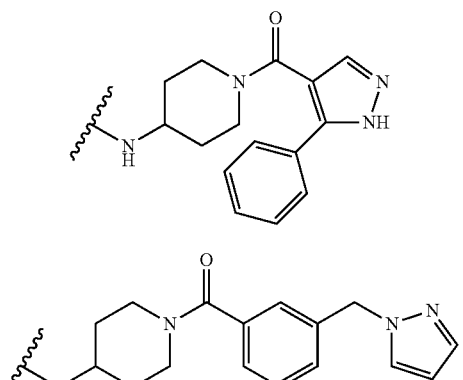 | 27 | 599 |
| 4-29 | 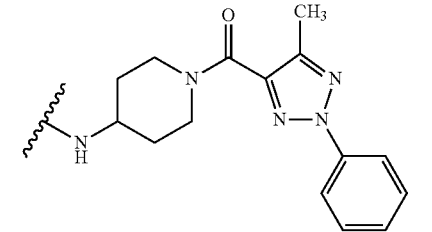 [SMILES: *NC1CCN(C(=O)c2nn(-c3ccccc3)nc2C)CC1] | 7 | 613 |
| 4-30 | 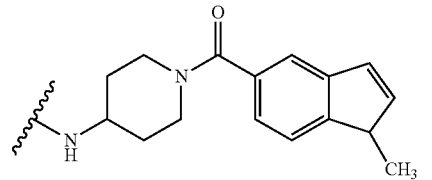 [SMILES: *NC1CCN(C(=O)c2ccc3c(c2)C=CC3C)CC1] | 137 | 614 |
| 4-31 | 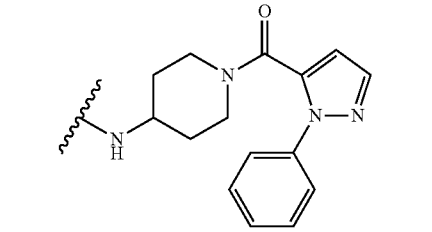 [SMILES: *NC1CCN(C(=O)c2ccnn2-c2ccccc2)CC1] | 3 | 586 |
| 4-32 | 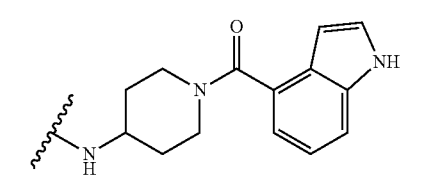 [SMILES: *NC1CCN(C(=O)c2cccc3[nH]ccc23)CC1] | 54 | 599 |
| 4-33 | | 7 | 572 |

-continued
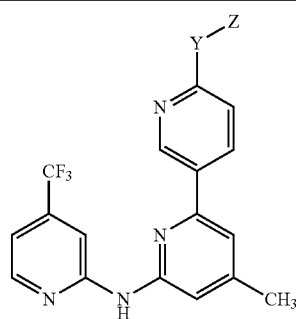
| Ex. | Y—Z | IC50 (nM) | [M + H]+ Obs'd |
|---|---|---|---|
| 4-34 | (4-piperidinyl-NH linked to C(=O)CH2-(2,3-dimethyl-1H-indol-5-yl)) | 8 | 614 |
| 4-35 | (4-piperidinyl-NH linked to C(=O)-1,6-naphthyridin-5-yl) | 3 | 585 |
| 4-36 | (4-piperidinyl-NH linked to C(=O)-3-(1H-pyrazol-1-yl)phenyl) | 10 | 599 |
| 4-37 | (4-piperidinyl-NH linked to C(=O)-pyrazolo[1,5-a]pyrimidin-3-yl) | 1 | 574 |
| 4-38 | (4-piperidinyl-NH linked to C(=O)-2-(N(CH3)2)phenyl) | 40 | 576 |
| 4-39 | (4-piperidinyl-NH linked to C(=O)-6-hydroxynaphthalen-1-yl) | 7 | 599 |

-continued
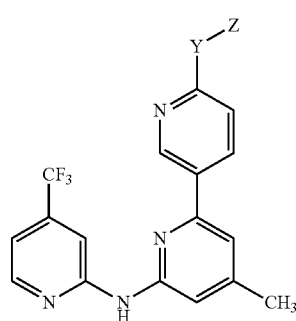
| Ex. | Y—Z | IC50 (nM) | [M + H]+ Obs'd |
|---|---|---|---|
| 4-40 | piperidine-N-C(O)-phenyl-CF3 | 102 | 601 |
| 4-41 | piperidine-N-C(O)-CH2-naphthyl | 58 | 597 |
| 4-42 | piperidine-N-C(O)-phenyl-N(CH3)2 | 4 | 576 |
| 4-43 | piperidine-N-C(O)-fluorenone | 29 | 635 |
| 4-44 | piperidine-N-C(O)-1,8-naphthyridinyl | <0.5 | 585 |
| 4-45 | piperidine-N-C(O)-quinolin-8-yl | 7 | 584 |

-continued
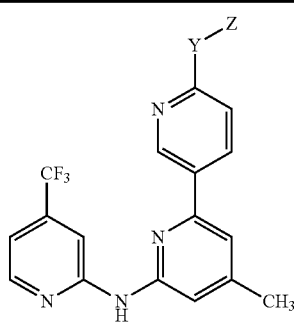
| Ex. | Y—Z | IC50 (nM) | [M + H]+ Obs'd |
|---|---|---|---|
| 4-46 | piperidine-NH linker, N-C(=O)-phenyl-SO2CH3 | 4 | 611 |
| 447 | piperidine-NH linker, N-C(=O)-(2-oxoindolin-7-yl) | 6 | 588 |
| 4-48 | piperidine-NH linker, N-C(=O)-(2-chloro-5-pyrazol-1-yl-phenyl) | 30 | 633 |
| 4-49 | piperidine-NH linker, N-C(=O)-isoquinolin-3-yl | 19 | 583 |
| 4-50 | piperidine-NH linker, N-C(=O)-(3-phenoxyphenyl) | 97 | 625 |
| 4-51 | piperidine-NH linker, N-C(=O)-(6-methylquinolin-3-yl) | 10 | 598 |

-continued
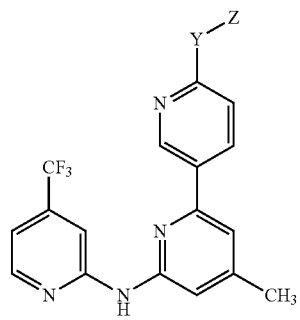
| Ex. | Y—Z | IC50 (nM) | [M + H]+ Obs'd |
|---|---|---|---|
| 4-52 | | 53 | 597 |
| 4-53 | | 78 | 627 |
| 4-54 | | 149 | 621 |
| 4-55 | (* = (S)) | 223 | 641 |
| 4-56 | | 39 | 591 |
| 4-57 | | 175 | 639 |

-continued
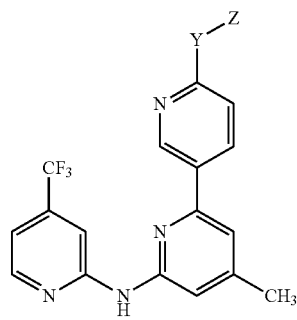
| Ex. | Y—Z | IC50 (nM) | [M + H]+ Obs'd |
|---|---|---|---|
| 4-58 | piperidine-NH- linked, C(O)-phenyl-NHC(O)CH3 | 4 | 590 |
| 4-59 | piperidine-NH- linked, C(O)-naphthyl | 61 | 583 |
| 4-60 | piperidine-NH- linked, C(O)-(1-benzyl-indol-3-yl) | 422 | 662 |
| 4-61 | piperidine-NH- linked, C(O)-isoquinolin-3-yl | 4 | 584 |
| 4-62 | piperidine-NH- linked, C(O)-phenyl-(1H-pyrazol-3-yl) | 15 | 599 |
| 4-63 | piperidine-NH- linked, C(O)-imidazo[1,2-a]pyridin-3-yl | 7 | 573 |

-continued
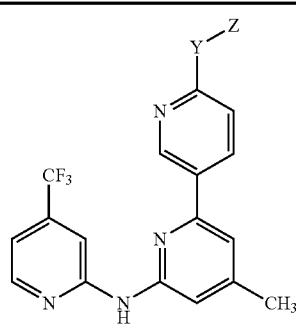
| Ex. | Y—Z | IC50 (nM) | [M + H]+ Obs'd |
|---|---|---|---|
| 4-64 | | 83 | 613 |
| 4-65 | | 20 | 584 |
| 4-66 | | 24 | 584 |
| 4-67 | | 178 | 623 |
| 4-68 | | 2 | 548 |
| 4-69 | | 138 | 623 |

-continued
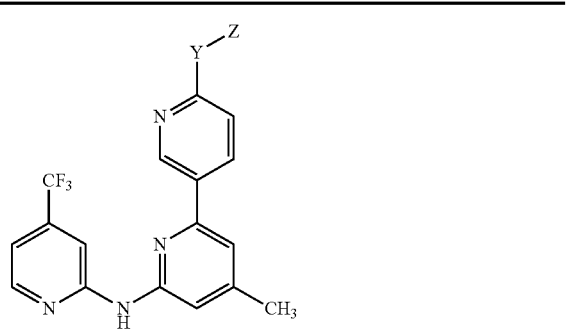
| Ex. | Y—Z | IC50 (nM) | [M + H]+ Obs'd |
|---|---|---|---|
| 4-70 | | 6 | 572 |
| 4-71 | | 21 | 567 |
| 4-72 | | 56 | 601 |
| 4-73 | | 21 | 581 |
| 4-74 | | 57 | 639 |
| 4-75 | | 39 | 615 |

-continued
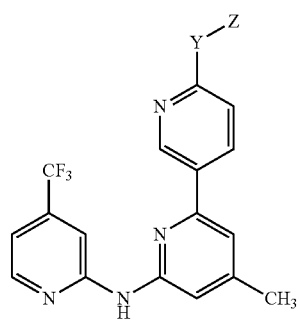
| Ex. | Y—Z | IC50 (nM) | [M + H]+ Obs'd |
|---|---|---|---|
| 4-76 | 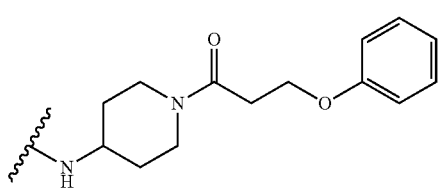 [SMILES: *NC1CCN(C(=O)CCOc2ccccc2)CC1] | 10 | 577 |
| 4-77 | 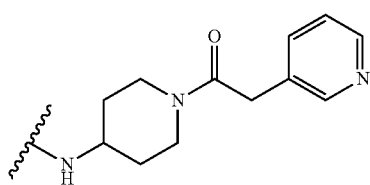 [SMILES: *NC1CCN(C(=O)Cc2cccnc2)CC1] | 1 | 548 |
| 4-78 | 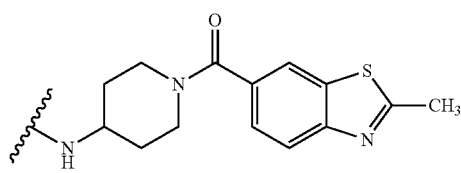 [SMILES: *NC1CCN(C(=O)c2ccc3nc(C)sc3c2)CC1] | 4 | 604 |
| 4-79 | 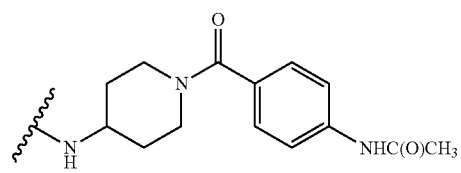 | 4 | 590 |
| 4-80 | 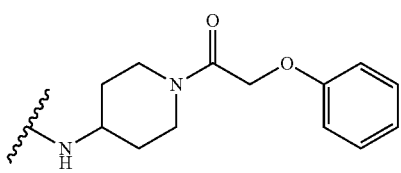 [SMILES: *NC1CCN(C(=O)COc2ccccc2)CC1] | 28 | 563 |
| 4-81 | 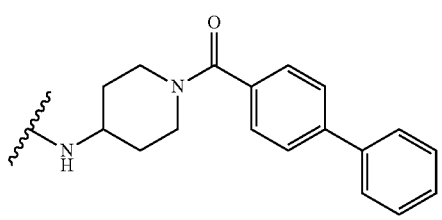 [SMILES: *NC1CCN(C(=O)c2ccc(-c3ccccc3)cc2)CC1] | 44 | 609 |

-continued
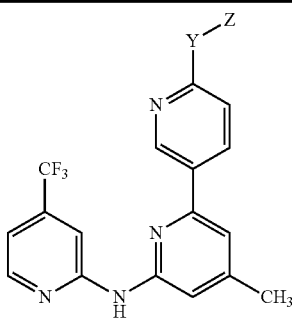
| Ex. | Y—Z | IC50 (nM) | [M + H]+ Obs'd |
|---|---|---|---|
| 4-82 | piperidine-N-C(O)-CH2-(3-cyanophenyl), linked via 4-NH | 3 | 572 |
| 4-83 | piperidine-N-C(O)-CH2-(3-hydroxyphenyl), linked via 4-NH | 3 | 563 |
| 4-84 | piperidine-N-C(O)-(4-pyridyl), linked via 4-NH | 4 | 534 |
| 4-85 | piperidine-N-C(O)-(3-cyanophenyl), linked via 4-NH | 7 | 558 |
| 4-86 | piperidine-N-C(O)-(1H-indazol-3-yl), linked via 4-NH | 7 | 573 |
| 4-87 | piperidine-N-C(O)-(2-methoxyphenyl), linked via 4-NH | 6 | 563 |
| 4-88 | piperidine-N-C(O)-CH2-(2-methyl-1H-indol-3-yl), linked via 4-NH | 11 | 600 |

-continued
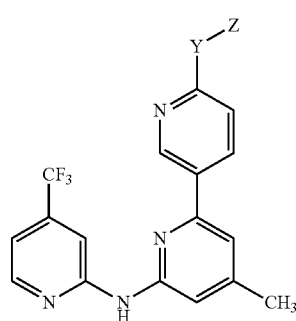
| Ex. | Y—Z | IC50 (nM) | [M + H]+ Obs'd |
|---|---|---|---|
| 4-89 | piperidine-NH linked, N-C(O)-CH2CH2CH2-N(2-oxopyrrolidinyl) | 1 | 582 |
| 4-90 | piperidine-NH linked, N-C(O)-C6H4-CN (para) | 4 | 558 |
| 4-91 | piperidine-NH linked, N-C(O)-CH2-C6H4-CN (para) | 4 | 572 |
| 4-92 | piperidine-NH linked, N-C(O)-quinolin-3-yl | 4 | 584 |
| 4-93 | piperidine-NH linked, N-C(O)-C6H4-OCH3 (para) | 5 | 563 |
| 4-94 | piperidine-NH linked, N-C(O)-pyridin-3-yl | 2 | 534 |

-continued
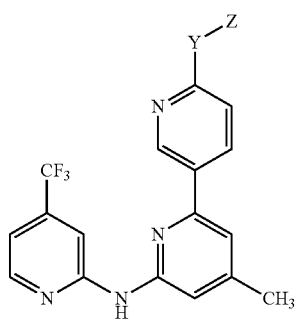
| Ex. | Y—Z | IC50 (nM) | [M + H]+ Obs'd |
|---|---|---|---|
| 4-95 | 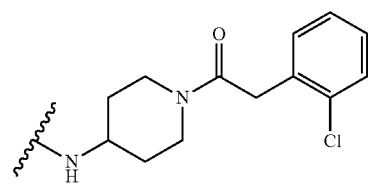 [SMILES: *NC1CCN(C(=O)Cc2ccccc2Cl)CC1] | 12 | 581 |
| 4-96 | 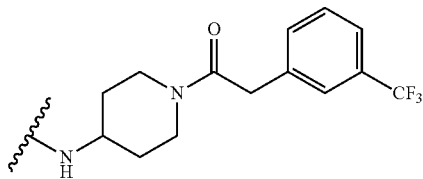 [SMILES: *NC1CCN(C(=O)Cc2cccc(C(F)(F)F)c2)CC1] | 103 | 615 |
| 4-97 | 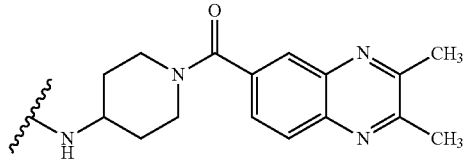 [SMILES: *NC1CCN(C(=O)c2ccc3nc(C)c(C)nc3c2)CC1] | 2 | 613 |
| 4-98 | 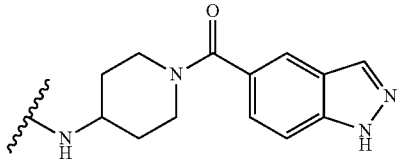 [SMILES: *NC1CCN(C(=O)c2ccc3[nH]ncc3c2)CC1] | 5 | 573 |
| 4-99 | 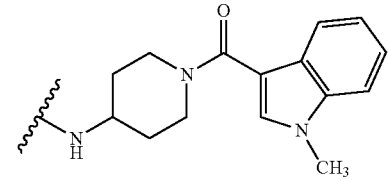 [SMILES: *NC1CCN(C(=O)c2cn(C)c3ccccc23)CC1] | 11 | 586 |
| 4-100 | 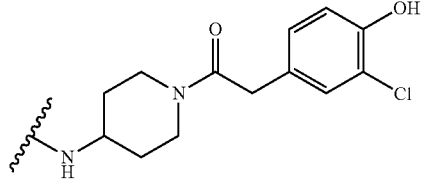 [SMILES: *NC1CCN(C(=O)Cc2ccc(O)c(Cl)c2)CC1] | 9 | 597 |

-continued
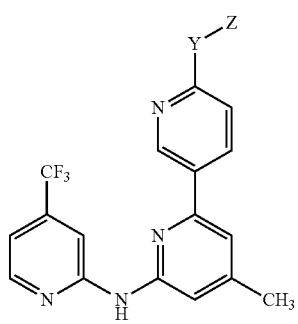
| Ex. | Y—Z | IC50 (nM) | [M + H]+ Obs'd |
|---|---|---|---|
| 4-101 | ![piperidine-N-C(O)-phenyl-3-OH] | 8 | 549 |
| 4-102 | ![piperidine-N-C(O)-CH2-(1-methylindol-3-yl)] | 7 | 600 |
| 4-103 | ![piperidine-N-C(O)-(2,3-dimethylindol-5-yl)] | 11 | 600 |
| 4-104 | ![piperidine-N-C(O)-pyridin-2-yl] | 2 | 534 |
| 4-105 | ![piperidine-N-C(O)-(3-chloropyridin-6-yl)] | 245 | 567 |
| 4-106 | ![piperidine-N-C(O)-phenyl-4-OH] | 6 | 549 |

-continued
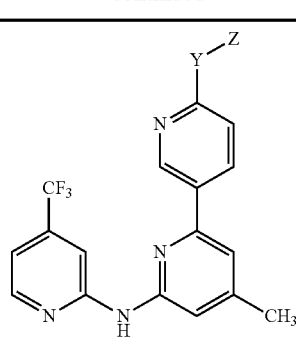
| Ex. | Y—Z | IC50 (nM) | [M + H]+ Obs'd |
|---|---|---|---|
| 4-107 | piperidine-N-C(O)CH2-(3-Cl-phenyl), NH linker | 13 | 581 |
| 4-108 | piperidine-N-C(O)CH2-(4-OH-phenyl), NH linker | 3 | 563 |
| 4-109 | piperidine-N-C(O)-(3-OCH3-phenyl), NH linker | 6 | 563 |
| 4-110 | piperidine-N-C(O)CH2-(3-OCH3-phenyl), NH linker | 6 | 577 |
| 4-111 | piperidine-N-C(O)-quinolin-6-yl, NH linker | 3 | 584 |
| 4-112 | piperidine-N-C(O)-(2-CN-phenyl), NH linker | 6 | 558 |
| 4-113 | piperidine-N-C(O)-(1-methyl-indol-2-yl), NH linker | 26 | 586 |

-continued
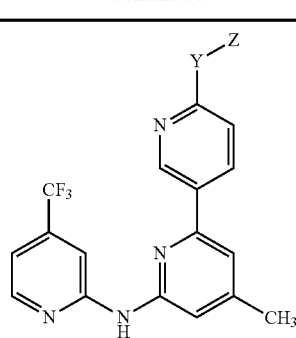
| Ex. | Y—Z | IC50 (nM) | [M + H]+ Obs'd |
|---|---|---|---|
| 4-114 | 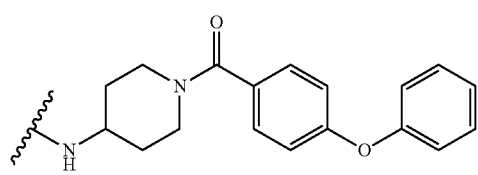 [SMILES: *NC1CCN(C(=O)c2ccc(Oc3ccccc3)cc2)CC1] | 23 | 625 |
| 4-115 | 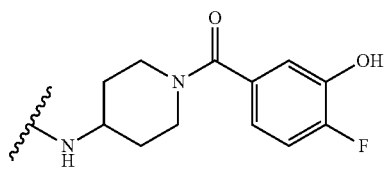 [SMILES: *NC1CCN(C(=O)c2ccc(F)c(O)c2)CC1] | 4 | 567 |
| 4-116 | 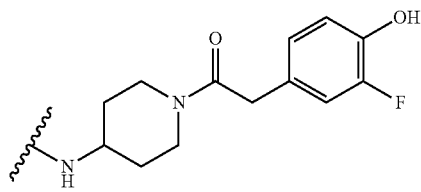 [SMILES: *NC1CCN(C(=O)Cc2ccc(O)c(F)c2)CC1] | 4 | 581 |
| 4-117 | 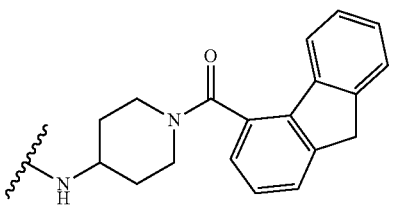 [SMILES: *NC1CCN(C(=O)c2cccc3c2-c2ccccc2C3)CC1] | 141 | 621 |
| 4-118 | 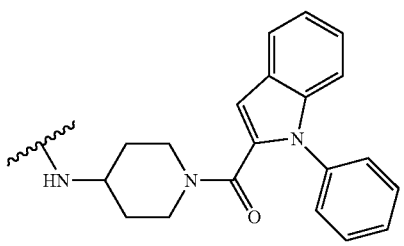 [SMILES: *NC1CCN(C(=O)c2cc3ccccc3n2-c2ccccc2)CC1] | 176 | 648 |
| 4-119 | 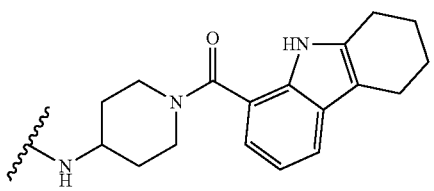 [SMILES: *NC1CCN(C(=O)c2cccc3c4c([nH]c23)CCCC4)CC1] | 19 | 626 |

-continued
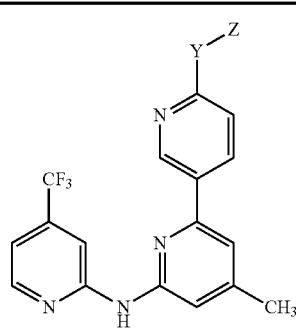
| Ex. | Y—Z | IC50 (nM) | [M + H]+ Obs'd |
|---|---|---|---|
| 4-120 | 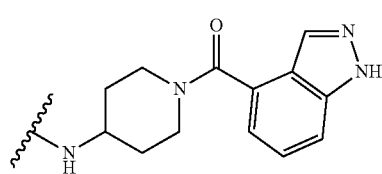 [SMILES: *NC1CCN(C(=O)c2cccc3[nH]ncc23)CC1] | 9 | 573 |
| 4-121 | 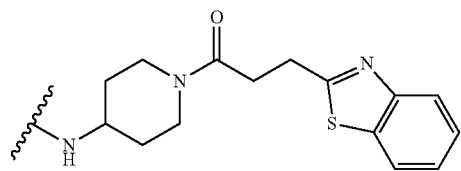 [SMILES: *NC1CCN(C(=O)CCc2nc3ccccc3s2)CC1] | 5 | 618 |
| 4-122 | 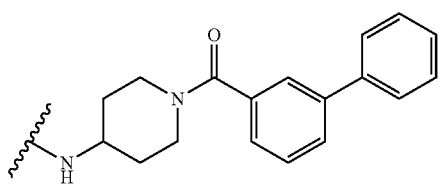 [SMILES: *NC1CCN(C(=O)c2cccc(-c3ccccc3)c2)CC1] | 3 | 609 |
| 4-123 | 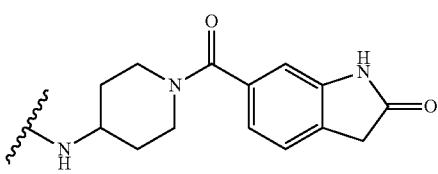 [SMILES: *NC1CCN(C(=O)c2ccc3c(c2)NC(=O)C3)CC1] | | 588 |

Example 5

6'-[(3S)-3-aminopyrrolidin-1-yl]-4-methyl-N-[4-(trifluoromethyl)pyridin-2-yl]-2,3'-bipyridin-6-amine

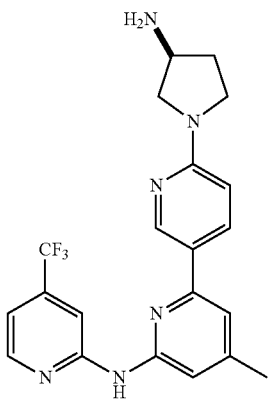 [SMILES: Cc1cc(Nc2cc(C(F)(F)F)ccn2)nc(-c2ccc(N3CC[C@H](N)C3)nc2)c1]

2,2,2-Trifluoroacetic acid (728 μL, 9.45 mmol) was added to tert-butyl [(3S)-1-(4-methyl-6-{[4-(trifluoromethyl)pyridin-2-yl]amino}-2,3'-bipyridin-6'-yl)pyrrolidin-3-yl]carbamate (243 mg, 0.472 mmol). The mixture was stirred at room temperature for 3 hours.

Saturated sodium bicarbonate solution was added, then the product was extracted with ethyl acetate (3×) to afford 6'-[(3S)-3-aminopyrrolidin-1-yl]-4-methyl-N-[4-(trifluoromethyl)pyridin-2-yl]-2,3'-bipyridin-6-amine, which was used without further purification. MS ESI calcd for $C_{21}H_{22}F_3N_6$ [M+H]+ 415. found 415. $^1$H NMR (500 MHz, DMSO-$d_6$) δ 10.24 (s, 1H), 8.50 (d, J=5.5 Hz, 1H), 8.47-8.42 (m, 2H), 8.32 (s, 1H), 7.38 (s, 1H), 7.36 (s, 1H), 7.21 (d, J=5.1, 1H), 7.11 (m, 1H), 3.96-3.85 (m, 3H), 2.83 (t, J=11.6 Hz, 2H), 2.35 (s, 3H), 1.97-1.86 (m, 2H), 1.40-1.32 (m, 2H). rhSyk IC$_{50}$=1 nM.

The compounds in the following Table were prepared according to the method described for Example 5.

| Ex. | Y—Z | IC50 (nM) | rhSyk Activity | [M + H]+ Observed | Example |
|---|---|---|---|---|---|
| 5-1 | ![NH2 piperidine, racemic] | 2 | +++ | 429 | 5-1 |
| 5-2 | ![piperidine-NH2] | 6 | +++ | 429 | 5-2 |
| 5-3 | ![HO-piperidine] | 9 | +++ | 430 | 5-3 |

Example 6

N-[(3S)-1-(4-methyl-6-{[4-(trifluoromethyl)pyridin-2-yl]amino}-2,3'-bipyridin-6'-yl)pyrrolidin-3-yl]acetamide

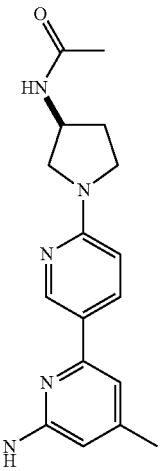

N,N-Diisopropylethylamine (0.032 mL, 0.181 mmol), acetic anhydride (6.26 μL, 0.066 mmol), 6'-[(3S)-3-aminopyrrolidin-1-yl]-4-methyl-N-[4-(trifluoromethyl)pyridin-2-yl]-2,3'-bipyridin-6-amine (Example 5, 25 mg, 0.060 mmol), and THF (1 mL) were added to a flask and stirred at room temperature for 16 hours. The crude solution was purified via reverse phase high pressure liquid chromatography to afford N-[(3S)-1-(4-methyl-6-{[4-(trifluoromethyl)pyridin-2-yl]amino}-2,3'-bipyridin-6'-yl)pyrrolidin-3-yl]acetamide. MS ESI calcd. for $C_{23}H_{24}F_3N_6O$ [M+H]+ 457. found 457. $^1$H NMR (500 MHz, DMSO-$d_6$) δ 10.08 (s, 1H), 8.76 (s, 1H), 8.60 (s, 1H), 8.47 (d, J=5.0 Hz, 1H), 8.11 (m, 1H), 7.24 (s, 1H), 7.17 (d, J=5.0 Hz, 1H) 7.12 (s, 1H), 6.46 (d, J=8.8 Hz, 1H), 3.52-3.60 (m, 3H), 3.43 (m, 1H), 3.12 (m, 1H), 2.30 (s, 3H), 2.05 (s, 1H), 1.87-1.80 (m, 2H), 1.72 (s, 1H). rhSyk IC$_{50}$=17 nM.

The compound in the following Table was prepared according to the method described for Example 6.

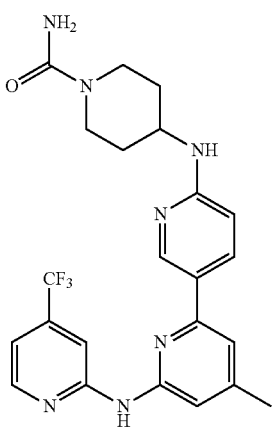 [SMILES: Cc1cc(Nc2cc(C(F)(F)F)ccn2)nc(-c2ccc(NC3CCN(C(N)=O)CC3)nc2)c1]

| Ex. | R$^d$ | IC$_{50}$ (nM) | [M + H]+ Observed |
|---|---|---|---|
| 6-1 | indol-6-yl | 17 | 558 |

Example 7

4-(4-Methyl-6-(4-(trifluoromethyl)pyridin-2-ylamino)-2,3'-bipyridin-6'-ylamino)piperidine-1-carboxamide Potassium cyanate (9.47 mg, 0.117 mmol), acetic acid (0.017 mL, 0.292 mmol), 4-methyl-N6'-(piperidin-4-yl)-N6-(4-(trifluoromethyl)pyridin-2-yl)-2,3'-bipyridine-6,6'-diamine (25 mg, 0.058 mmol), and THF (1 mL) were combined. The mixture was stirred at room temperature for 16 hours. The crude solution was purified via reverse phase high pressure liquid chromatography to afford 4-(4-methyl-6-(4-(trifluoromethyl)pyridin-2-ylamino)-2,3'-bipyridin-6'-ylamino)piperidine-1-carboxamide. MS ESI calcd. for $C_{23}H_{25}F_3N_7O$ [M+H]$^+$ 472. found 472. $^1$H NMR (500 MHz, DMSO-d$_6$) δ 10.25 (s, 1H), 8.53-8.49 (m, 3H), 8.28 (s, 1H), 8.24 (d, J=6.5 Hz, 1H), 7.44 (s, 1H), 7.39 (s, 1H), 7.22-7.16 (m, 2H), 4.42 (m, 1H), 3.80 (m, 1H), 3.72-3.65 (m, 2H), 3.45 (dd, J=11.0, 4.0 Hz, 1H), 2.36 (s, 3H), 2.22 (m, 1H), 2.00 (m, 1H), 1.82 (s, 3H). rhSyk IC$_{50}$=4 nM.

The compound in the following Table was prepared according to the method described for Example 7.

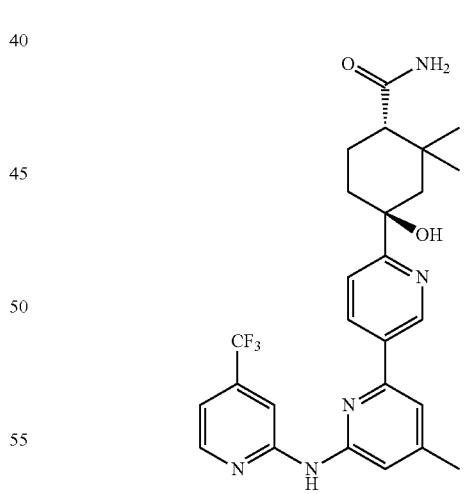

| Ex. | Y—Z | IC$_{50}$ (nM) | [M + H]+ Observed |
|---|---|---|---|
| 7-1 | NHC(O)NH$_2$ racemic | 5 | 472 |

Example 8

(1S,4S or 1R,4R)-4-Hydroxy-2,2-dimethyl-4-(4-methyl-6-{[4-(trifluoromethyl)pyridin-2-yl]amino}-2,3'-bipyridin-6'-yl)cyclohexanecarboxamide (Enantiomer 1)

To a flask containing (1S,4S or 1R,4R)-4-hydroxy-2,2-dimethyl-4-(4-methyl-6-{[4-(trifluoromethyl)pyridin-2-yl]amino}-2,3'-bipyridin-6'-yl)cyclohexanecarboxylic acid (267 mg, 0.366 mmol), EDC (141 mg, 0.733 mmol), HOBt (112 mg, 0.733 mmol) and DIEA (0.320 mL, 1.832 mmol) in DMF (3.66 mL) was added ammonium chloride (59 mg, 1.099 mmol). The solution was stirred at room temperature for 16 hours. Water was added, and the mixture extracted with ethyl acetate (3×). The organic layers were combined, dried with magnesium sulfate, filtered, and concentrated under reduced pressure. The residue was purified by chromatography on silica gel (6% methanol:dichloromethane) to afford (1S,4S or 1R,4R)-4-hydroxy-2,2-dimethyl-4-(4-methyl-6-{[4-(trifluoromethyl)pyridin-2-yl]amino}-2,3'-bipyridin-6'-yl)cyclohexanecarboxamide as a white solid. MS ESI calcd. for $C_{26}H_{29}F_3N_5O_2$ [M+H]$^+$ 500. found 500. $^1$H NMR (600 MHz, DMSO-d$_6$) δ 10.19 (s, 1H), 9.10 (d, J=1.7 Hz, 1H), 8.54 (s, 1H), 8.47 (d, J=5.2 Hz, 1H), 8.33 (dd, J=8.4, 2.3 Hz, 1H), 7.65 (d, J=8.4 Hz, 1H), 7.43 (s, 1H), 7.30 (s, 1H), 7.17 (d, J=5.2 Hz, 1H), 7.16 (s, 1H), 6.54 (s, 1H), 4.99 (s, 1H), 2.63-2.57 (m, 1H), 2.36 (d, J=13.6 Hz, 1H), 2.34 (s, 3H), 2.10 (t, J=5.1 Hz, 1H), 1.96-1.90 (m; 1H), 1.75-1.65 (m, 1H), 1.41-1.35 (m, 1H), 1.32 (d, J=13.4 Hz, 1H), 1.09 (s, 3H), 0.61 (s, 3H). rhSyk IC$_{50}$=23 nM.

The second enantiomer (Ex. 8-1) of the compound of Example 8 was prepared according to the method described for Example 8. MS ESI calcd. for $C_{26}H_{29}F_3N_5O_2$ [M+H]$^+$ 500. found 500. rhSyk IC$_{50}$=25 nM.

Example 9

4-(4-Methyl-6-{[4-(trifluoromethyl)pyridin-2-yl]amino}-2,3'-bipyridin-6'-yl)-1-(1H-pyrrolo[2,3-b]pyridin-6-ylcarbonyl)piperidin-4-ol

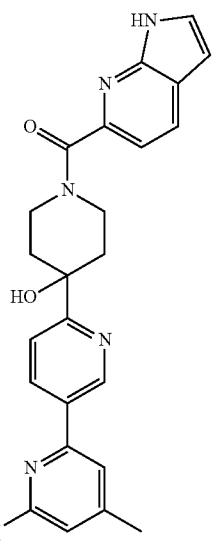

To a flask containing 4-(4-methyl-6-{[4-(trifluoromethyl)pyridin-2-yl]amino}-2,3'-bipyridin-6'-yl)piperidin-4-ol (35 mg, 0.0.082 mmol), EDC (31 mg, 0.0.163 mmol), HOBt (25 mg, 0.163 mmol) and DIEA (0.071 mL, 0.408 mmol) in DMF (1.63 mL) was added 7-quinoline carboxylic acid (42 mg, 0.245 mmol). The solution was stirred at room temperature for 16 hours. The reaction solution was then filtered and purified by mass triggered reverse phase high pressure liquid chromatography to provide 4-(4-methyl-6-{[4-(trifluoromethyl)pyridin-2-yl]amino}-2,3'-bipyridin-6'-yl)-1-(1H-pyrrolo[2,3-b]pyridin-6-ylcarbonyl)piperidin-4-ol as a white solid. MS ESI calcd. for $C_{30}H_{26}F_3N_7O_2$ [M+H]$^+$ 574. found 574. $^1$H NMR (600 MHz, DMSO-d$_6$) δ 11.79 (s, 1H), 10.22 (s, 1H), 9.15 (s, 1H), 8.53 (s, 1H), 8.48 (d, J=5.2 Hz, 1H), 8.45-8.37 (m, 1H), 8.03 (d, J=8.0 Hz, 1H), 7.83-7.79 (m, 1H), 7.54 (s, 1H), 7.47 (s, 1H), 7.31 (s, 1H), 7.25 (d, J=8.0 Hz, 1H), 7.31-7.27 (m, 1H), 6.48 (s, 1H), 4.54-4.43 (m, 2H), 3.30-3.20 (m, 2H), 2.34 (s, 3H), 2.24-2.10 (m, 2H), 1.75-1.68 (m, 1H), 1.60-1.46 (m, 1H). rhSyk IC$_{50}$=9 nM.

The compounds in the following Table were prepared according to the method described for Example 9:

| Ex. | R$^d$ | IC50 (nM) | [M + H]+ Obs'd |
|---|---|---|---|
| 9-1 | quinolin-7-yl | 30 | 585 |
| 9-2 | indol-6-yl | 13 | 573 |
| 9-3 | 6-methyl-indol-3-yl | 10 | 587 |
| 9-4 | 2,3-dimethyl-quinoxalin-6-yl | 5 | 614 |
| 9-5 | 3-methyl-indol-2-yl | 112 | 587 |
| 9-6 | 5-(4-pyridyl)-pyrazol-3-yl | 12 | 601 |

Example 10 trans-4-[(4-methyl-6-{[4-(trifluoromethyl)pyridin-2-yl]amino}-2,3'-bipyridin-6'-yl)methyl]cyclohexanecarboxylic acid cis-4-[(4-methyl-6-{[4-(trifluoromethyl)pyridin-2-yl]amino}-2,3'-bipyridin-6'-yl)methyl]cyclohexanecarboxylic acid

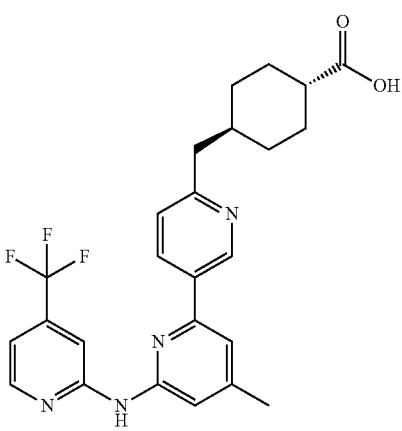

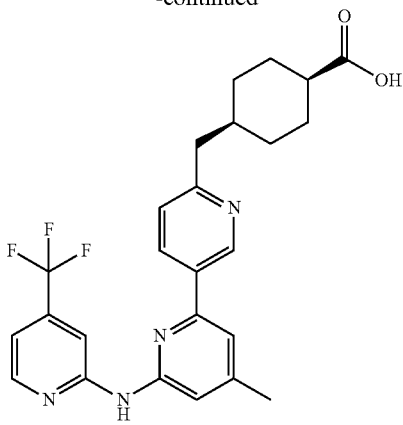

To a flask containing methyl 4-[(4-methyl-6-{[4-(trifluoromethyl)pyridin-2-yl]amino}-2,3'-bipyridin-6'-yl)carbonyl]cyclohexanecarboxylate (50 mg, 0.10 mmol) in DMSO (1 mL) was added potassium hydroxide (113 mg, 2.01 mmol) and hydrazine (57 µL, 1.81 mmol). The reaction was heated in a sealed vessel to 140° C. for 3 hours. The reaction mixture was then cooled to ambient temperature and filtered. The solution was then purified directly by reverse phase column chromatography (acetonitrile/water with 0.1% TFA modifier) to afford trans-4-[(4-methyl-6-{[4-(trifluoromethyl)pyridin-2-yl]amino}-2,3'-bipyridin-6'-yl)methyl]cyclohexanecarboxylic acid and cis-4-[(4-methyl-6-{[4-(trifluoromethyl)pyridin-2-yl]amino}-2,3'-bipyridin-6'-yl)methyl]cyclohexanecarboxylic acid.

Characterization data for the trans isomer: MS ESI calcd. for $C_{25}H_{26}F_3N_4O_2$ [M+H]$^+$ 471. found 471. $^1$H NMR (500 MHz, DMSO-$d_6$) δ 10.36-10.24 (m, 1H), 9.22 (s, 1H), 8.72 (s, 1H), 8.51 (d, J=5.1 Hz, 1H), 8.43 (s, 1H), 7.79 (d, J=7.9 Hz, 1H), 7.57 (s, 1H), 7.42 (s, 1H), 7.22 (d, J=5.2 Hz, 1H), 2.83 (d, J=6.9 Hz, 2H), 2.38 (s, 3H), 2.17-2.10 (m, 1H), 1.87 (d, J=11.0 Hz, 2H), 1.80-1.70 (m, 1H), 1.69-1.61 (m, 2H), 1.32-1.18 (m, 2H), 1.13-1.00 (m, 2H). rhSyk IC$_{50}$=<0.5 nM.

Characterization data for the cis isomer: MS ESI calcd. for $C_{25}H_{26}F_3N_4O_2$ [M+H]$^+$ 471. found 471. $^1$H NMR (500 MHz, DMSO-$d_6$) δ 10.28 (s, 1H), 9.21 (s, 1H), 8.65 (s, 1H), 8.50 (d, J=5.2 Hz, 1H), 8.45 (s, 1H), 7.72 (d, J=7.7 Hz, 1H), 7.55 (s, 1H), 7.40 (s, 1H), 7.22 (d, J=5.1 Hz, 1H), 2.83 (d, J=7.4 Hz, 2H), 2.37 (s, 3H), 1.95-1.84 (m, 2H), 1.56-1.39 (m, 4H), 1.31-1.13 (m, 4H). rhSyk IC$_{50}$=1 nM.

Example 11

Methyl trans-4-[(1R or 1S)-(6-{[4-(difluoromethyl)pyridin-2-yl]amino}-4-methyl-2,3'-bipyridin-6'-yl)-1-hydroxyethyl]cyclohexanecarboxylate To a nitrogen degassed solution of methyl trans-4-[(1R or 1S)-(5-bromopyridin-2-yl)-1-hydroxyethyl]cyclohexane carboxylate (35 g, 102 mmol, Intermediate 31a, faster eluting isomer from chiral SFC separation of the racemate) in dioxane (350 mL) was added potassium acetate (20.1 g, 205 mmol), bis(pinacolate)diboron (28.6 g, 112 mmol), and [1,1-bis(diphenylphosphino)ferrocene]dichloropalladium (II)-dichloromethane complex (4.2 g, 5.11 mmol). The mixture was degassed by sparging with nitrogen for 30 minutes and the reaction was heated to 90° C. for 2 hours. The reaction mixture was allowed to cool to room temperature. 6-Bromo-N-[4-(difluoromethyl)pyridin-2-yl]-4-methylpyridin-2-amine (32.8 g, 104 mmol) was added followed by aqueous potassium carbonate (2M, 128 mL, 256 mmol). The resulting mixture was degassed by sparging for 5 minutes with nitrogen and heated at 90° C. for 2.5 hours. The reaction was allowed to cool to room temperature, then diluted with water (50 mL) and EtOAc (50 mL). The reaction was filtered through a pad of CELITE. The residue was washed with water (200 mL) and EtOAc (200 mL). The filtered suspension was transferred into a separatory funnel. The layers were separated, and the aqueous layer was washed with EtOAc (2×150 mL). The organic layers were combined, dried with MgSO$_4$, filtered, and concentrated in vacuo to afford a light red oil. The oil was absorbed on silica gel and purified via silica gel column chromatography (EtOAc/Hexanes). Fractions containing the desired product were concentrated, reabsorbed on silica gel and purified again via silica gel column chromatography (EtOAc/Hexanes). The desired product fractions were concentrated in vacuo. The residue was dissolved in EtOAc (1.5 L) and stirred for 1 hour with DARCO 174 KB-G (50 g). The mixture was filtered through a pad of Celite (200 g), and the residue was washed with EtOAc (1500 mL). The filtrate was concentrated in vacuo to afford methyl trans-4-[(1R or 1S)-(6-{[4-(difluoromethyl)pyridin-2-yl]amino}-4-methyl-2,3'-bipyridin-6'-yl)-1-hydroxyethyl]cyclohexanecarboxylate.

MS ESI calcd. for $C_{27}H_{31}F_2N_4O_3$ [M+H]$^+$ 497. found 497. $^1$H NMR (600 MHz, CDCl$_3$) δ 9.05 (d, J=1.5 Hz, 1H), 8.35 (d, J=5.1 Hz, 1H), 8.33 (dd, J=8.3, 2.2 Hz, 1H), 8.15 (s, 1H), 7.51 (s, 1H), 7.36 (d, J=8.3 Hz, 1H), 7.19 (s, 1H), 7.09 (s, 1H), 6.97 (d, J=5.1 Hz, 1H), 6.63 (t, J=56.0 Hz, 1H), 5.24 (s, 1H), 3.61 (s, 3H), 2.40 (s, 3H), 2.18 (tt, J=12.3, 3.4 Hz, 1H), 2.10-1.97 (m, 2H), 1.92-1.83 (m, 1H), 1.64 (tt, J=11.8, 3.2 Hz, 1H), 1.51 (s, 3H), 1.46-1.35 (m, 1H), 1.33-1.20 (m, 3H), 1.15 (m, 1H). rhSyk IC$_{50}$=9 nM.

Example 12 trans-4-[(1R or 1S)-(6-{[4-(Difluoromethyl)pyridin-2-yl]amino}-4-methyl-2,3'-bipyridin-6'-yl)-1-hydroxyethyl]cyclohexanecarboxylic acid

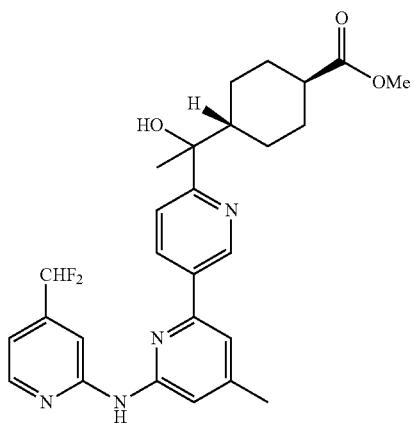 [SMILES: COC(=O)[C@H]1CC[C@H](C(C)(O)c2ccc(-c3cc(C)cc(Nc4cc(C(F)F)ccn4)n3)cn2)CC1]
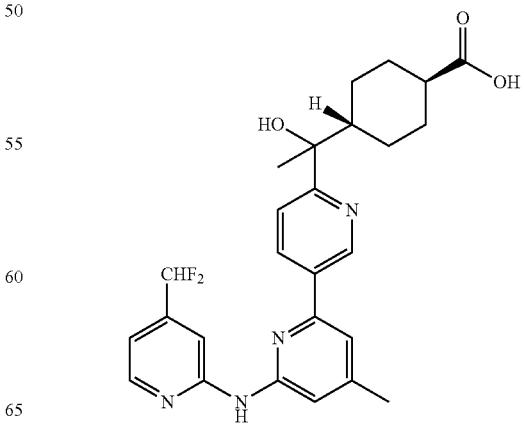

To a solution of methyl trans-4-[(1R or 1S)-(6-{[4-(difluoromethyl)pyridin-2-yl]amino}-4-methyl-2,3'-bipyridin-6'-yl)-1-hydroxyethyl]cyclohexanecarboxylate (Example 11, 18.66 g, 37.6 mmol) from the previous step in methanol (186 mL) was slowly added aqueous sodium hydroxide (1 M, 132 mL, 132 mmol). An exotherm (~15° C.) was observed and the reaction changed from a yellow solution to a milky white heterogenous mixture. The reaction was then heated to 65° C. for 1 hour. The reaction was allowed to cool to 50° C., and aqueous hydrochloric acid (1 M, 132 mL, 132 mmol) was added via addition funnel (~30 min). Crystallization occurred upon neutralization and stirring was continued for 1 hour. The reaction was filtered at 30° C. The residue was washed with water (2×250 mL) and dried under nitrogen to give a solid. The solid was transferred to a flask, diluted with EtOAc (170 mL) and heated to 65° C. with stirring for 2 hours. Hexane (170 mL) was added, and the mixture was allowed to cool to room temperature and aged for 1 hour. The mixture was filtered, the residue was washed with hexanes (170 mL) and dried under nitrogen to afford trans-4-[(1R or 1S)-(6-{[4-(difluoromethyl)pyridin-2-yl]amino}-4-methyl-2,3'-bipyridin-6'-yl)-1-hydroxyethyl]cyclohexanecarboxylic acid as a white solid. MS ESI calcd. for $C_{26}H_{29}F_2N_4O_3$ [M+H]$^+$ 483. found 483. $^1$H NMR (500 MHz, $CD_3OD$) δ 9.16 (s, 1H), 8.44 (d, J=8.4 Hz, 1H), 8.34 (d, J=5.2 Hz, 1H), 8.28 (s, 1H), 7.71 (d, J=8.4 Hz, 1H), 7.36 (s, 1H), 7.30 (s, 1H), 7.02 (d, J=5.2 Hz, 1H), 6.82 (t, J=55.8 Hz, 1H), 2.42 (s, 3H), 2.20-1.79 (m; 5H), 1.56 (s, 3H), 1.47-1.14 (m, 5H). rhSyk $IC_{50}$=<0.5 nM.

The following isomers of Example 12 were similarly prepared:

| Ex. | Compound Name | IC50 (nM) | [M + H]+ Obs'd |
|---|---|---|---|
| 12-1 | trans-4-[(1R or 1S)-(6-{[4-(difluoromethyl)pyridin-2-yl]-amino}-4-methyl-2,3'-bipyridin-6'-yl)-1-hydroxyethyl]-cyclohexanecarboxylic acid (from the slower eluting isomer of Intermediate 31b) (enantiomer 2) | 1 | 483 |
| 12-2 | cis-4-[(1R or 1S)-(6-{[4-(difluoromethyl)pyridin-2-yl]amino}-4-methyl-2,3'-bipyridin-6'-yl)-1-hydroxyethyl]cyclohexane-carboxylic acid (from the faster eluting isomer of the SFC chrial resolution of Intermediate 33) (enantiomer 1) | <0.5 | 483 |
| 12-3 | cis-4-[(1R or 1S)-(6-{[4-(difluoromethyl)pyridin-2-yl]amino}-4-methyl-2,3'-bipyridin-6'-yl)-1-hydroxyethyl]cyclohexane-carboxylic acid (from the slower eluting isomer of the SFC chrial resolution of Intermediate 33) (enantiomer 2) | 1 | 483 |

Example 13 trans-4-(1R or 1S)-(6-(4-(Difluoromethyl)pyridin-2-ylamino)-4-methyl-2,3'-bipyridin-6'-yl)-1-fluoroethyl)cyclohexanecarboxylic acid

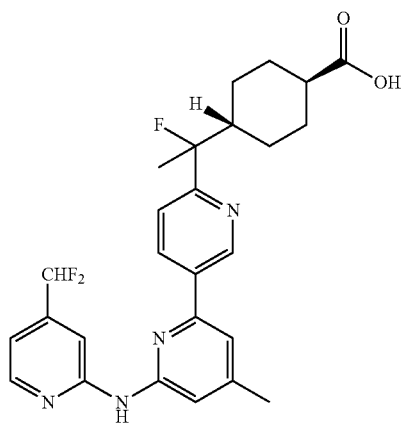 [SMILES: Cc1cc(Nc2cc(C(F)F)ccn2)nc(-c2ccc(C(C)(F)[C@H]3CC[C@H](C(=O)O)CC3)nc2)c1]

Step 1:
Methyl trans-4-(1R or 1S)-(6-(4-(difluoromethyl)pyridin-2-ylamino)-4-methyl-2,3'-bipyridin-6'-yl)-1-hydroxyethyl)cyclohexanecarboxylate (Example 11, 51 mg, 0.103 mmol) was dissolved in DCM (198 µL) and ethanol (1 µL). Deoxofluor (95 µL, 0.514 mmol) was added slowly, and the resulting mixture was stirred at room temperature for 15 minutes. The reaction was quenched slowly with water and then diluted with EtOAc. The organic layer was separated, dried over sodium sulfate, filtered, and concentrated under reduced pressure. The residue was purified by column chromatography on silica gel (10-100% EtOAc/hexanes) to afford methyl trans-4-(1R or 1S)-(6-(4-(difluoromethyl)pyridin-2-ylamino)-4-methyl-2,3'-bipyridin-6'-yl)-1-fluoroethyl)cyclohexanecarboxylate. MS ESI calcd. for $C_{27}H_{30}F_3N_4O_2$ [M+H]$^+$ 499. found 499.

Step 2:
To methyl trans-4-(1R or 1S)-(6-(4-(difluoromethyl)pyridin-2-ylamino)-4-methyl-2,3'-bipyridin-6'-yl)-1-fluoroethyl)cyclohexanecarboxylate (40 mg, 0.080 mmol) in MeOH (400 µL), sodium hydroxide (1M in water, 400 µL, 0.400 mmol) was added. The reaction mixture was heated in a microwave at 100° C. for 20 minutes. The pH was adjusted to 3-4 with HCl (1M in water). The reaction mixture was diluted with 10% IPA/CHCl$_3$, and water, then extracted with 10% IPA/CHCl$_3$. The organic layer was separated, washed with brine, dried over sodium sulfate, filtered and concentrated under reduced pressure. The residue was purified by reverse phase-HPLC using a 15-60% ACN/H$_2$O gradient with a 0.1% TFA modifier to afford trans-4-(1R or 1S)-(6-(4-(difluoromethyl)pyridin-2-ylamino)-4-methyl-2,3'-bipyridin-6'-yl)-1-fluoroethyl)cyclohexanecarboxylic acid as a pale yellow solid. MS ESI calcd. for $C_{26}H_{28}F_3N_4O_2$ [M+H]$^+$ 485. found 485. $^1$H NMR (500 MHz, DMSO-d$_6$) δ 10.22 (s, 1H), 9.20 (s, 1H), 8.50-8.34 (m, 2H), 8.22 (s, 1H), 7.57 (d, J=7.8 Hz, 1H), 7.48 (s, 1H), 7.35 (s, 1H), 7.10 (t, J=55.5 Hz, 1H), 7.06 (d, J=4.7 Hz, 1H), 2.36 (s, 3H), 2.08-1.78 (m, 5H), 1.63 (d, J=23.2 Hz, 3H), 1.43-0.96 (m, 5H). rhSyk $IC_{50}$=<0.5 nM.

Example 14 trans-4-[(1R or 1S)-(4-Methyl-6-{[4-(trifluoromethyl)pyridin-2-yl]amino}-2,3'-bipyridin-6'-yl)ethyl]cyclohexanecarboxylic acid

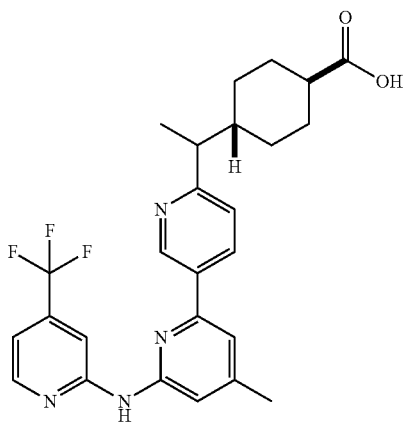 [SMILES: Cc1cc(Nc2cc(C(F)(F)F)ccn2)nc(-c2ccc(C(C)[C@H]3CC[C@H](C(=O)O)CC3)nc2)c1]

Step 1:

To a flask was added methyltriphenylphosphonium bromide (444 mg, 1.24 mmol) and THF (3.1 mL). The mixture was cooled to 0° C., and potassium tert-butoxide (1.0 M in THF, 1.39 mL, 1.39 mmol) was added. The mixture was stirred at 0° C. for 30 minutes. A solution of methyl trans-4-[(4-methyl-6-{[4-(trifluoromethyl)pyridin-2-yl]amino}-2,3'-bipyridin-6'-yl)carbonyl]cyclohexanecarboxylate (310 mg, 0.622 mmol) in THF (2 mL) was added dropwise at 0° C., and the mixture was stirred at 0° C. for 30 minutes. The reaction was diluted with ethyl acetate and water, and the mixture was extracted with ethyl acetate. The combined organic fractions were washed with brine, dried over sodium sulfate, filtered, and concentrated under reduced pressure. The residue was purified by column chromatography on silica gel, eluting with EtOAc/hexane (0-60%) to afford methyl trans-4-[1-(4-methyl-6-{[4-(trifluoromethyl)pyridin-2-yl]amino}-2,3'-bipyridin-6'-yl)ethenyl]cyclohexanecarboxylate as a white solid. MS ESI calcd. for $C_{27}H_{28}F_3N_4O_2$ [M+H]$^+$ 497. found 497.

Step 2:

To a flask was added methyl trans-4-[1-(4-methyl-6-{[4-(trifluoromethyl)pyridin-2-yl]amino}-2,3'-bipyridin-6'-yl)ethenyl]cyclohexanecarboxylate (21 mg, 0.042 mmol) and 10% palladium on carbon (0.450 mg, 4.23 µmol). The flask was evacuated and backfilled with nitrogen (5×). Methanol (846 µL) was added and the flask was evacuated and backfilled with nitrogen (5×). A balloon of hydrogen was attached and the mixture was stirred under an atmosphere of hydrogen at room temperature for 2 hours. The reaction was filtered through Celite, washing with methanol to afford methyl trans-4-[(1R or 1S)-(4-methyl-6-{[4-(trifluoromethyl)pyridin-2-yl]amino}-2,3'-bipyridin-6'-yl)ethyl]cyclohexanecarboxylate as a mixture of isomers. MS ESI calcd. for $C_{27}H_{30}F_3N_4O_2$ [M+H]$^+$ 499. found 499.

Step 3:

To methyl trans-4-[(1R or 1S)-(4-methyl-6-{[4-(trifluoromethyl)pyridin-2-yl]amino}-2,3'-bipyridin-6'-yl)ethyl]cyclohexanecarboxylate (20 mg, 0.080 mmol) in methanol (201 µL) was added sodium hydroxide (1 M in water, 201 µL, 0.201 mmol). The reaction mixture was heated in a microwave at 100° C. for 20 minutes. The pH was adjusted to 3-4 with HCl (1M in water). The reaction mixture was diluted with 10% IPA/CHCl$_3$, and water. The layers were separated, and the aqueous portion was extracted with 10% IPA/CHCl$_3$. The combined organic layers were washed with brine, dried over sodium sulfate, filtered, and concentrated under reduced pressure. The residue was purified by reverse phase-HPLC (15-60% ACN/H$_2$O gradient with a 0.1% TFA modifier) to afford trans-4-[(1R or 1S)-(4-methyl-6-{[4-(trifluoromethyl)pyridin-2-yl]amino}-2,3'-bipyridin-6'-yl)ethyl]cyclohexanecarboxylic acid as a mixture of isomers. MS ESI calcd. for $C_{26}H_{28}F_3N_4O_2$ [M+H]$^+$ 485. found 485. $^1$H NMR (500 MHz, DMSO-d$_6$) δ 10.29 (s, 1H), 9.19 (s, 1H), 8.65 (br s, 1H), 8.51 (d, J=5.0 Hz, 1H), 8.44 (s, 1H), 7.72 (br s, 1H), 7.55 (s, 1H), 7.41 (s, 1H), 7.22 (d, J=4.5 Hz, 1H), 2.84-2.80 (m, 1H), 2.38 (s, 3H), 2.12-2.04 (m, 1H), 1.94-1.88 (m, 2H), 1.82-1.76 (m, 1H), 1.66-1.58 (m, 1H), 1.34-1.24 (m, 2H), 1.29 (d, J=6.5 Hz, 3H), 1.24-1.12 (m, 1H), 1.04-0.90 (m, 2H). rhSyk IC$_{50}$=<0.5 nM.

Example 15 trans-4-((1R or 1S)-(3-Bromo-6-(4-(difluoromethyl)pyridin-2-ylamino)-4-methyl-2,3'-bipyridin-6'-yl)-1-hydroxyethyl)cyclohexanecarboxylic acid

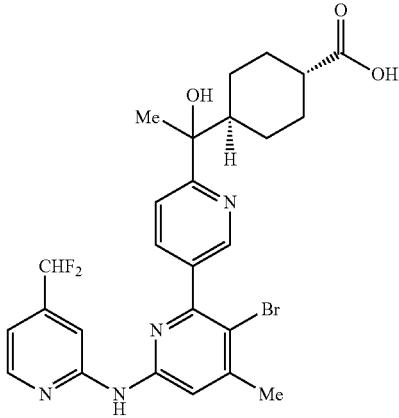 [SMILES: Cc1cc(Nc2cc(C(F)F)ccn2)nc(-c2ccc(C(C)(O)[C@H]3CC[C@H](C(=O)O)CC3)nc2)c1Br]

N-bromosuccinimide (12 mg, 0.067 mmol) was added to a solution of trans-4-((1R or 1S)-(6-(4-(difluoromethyl)pyridin-2-ylamino)-4-methyl-2,3'-bipyridin-6'-yl)-1-hydroxyethyl)cyclohexanecarboxylic acid (Example 12, 16 mg, 0.033 mmol) in DMF (350 µL) at 23° C. After stirring for 5 minutes, the reaction was diluted with water. The residue was purified directly by reverse phase preparative HPLC (acetonitrile:water+0.1% TFA) to give trans-4-((R or S)-1-(3-bromo-6-(4-(difluoromethyl)pyridin-2-ylamino)-4-methyl-2,3'-bipyridin-6'-yl)-1-hydroxyethyl)cyclohexanecarboxylic acid (28 mg, 0.035 mmol) as a colorless solid. MS ESI calcd for $C_{26}H_{28}BrF_2N_4O_3$ [M+H]$^+$ 561 and 563. found 561 and 563. $^1$H NMR (600 MHz, DMSO-d$_6$) δ 10.22 (s, 1H), 8.78 (s, 1H), 8.37 (d, J=5.1 Hz, 1H), 8.22 (s, 1H), 7.82 (s, 1H), 7.80 (s, 1H), 7.76 (s, 1H), 7.00 (d, J=5.1, 1H), 6.97 (t, J=55.5 Hz, 1H), 2.41 (s, 3H), 2.05-1.66 (m, 5H), 1.48 (s, 3H), 1.29-1.03 (m, 5H). rhSyk IC$_{50}$=1 nM.

Example 16

Sodium trans-4-[(1R or 1S)-1-(6-{[4-(difluoromethyl)pyridin-2-yl]amino}-4-methyl-2,3'-bipyridin-6'-yl)-1-hydroxyethyl]cyclohexanecarboxylate

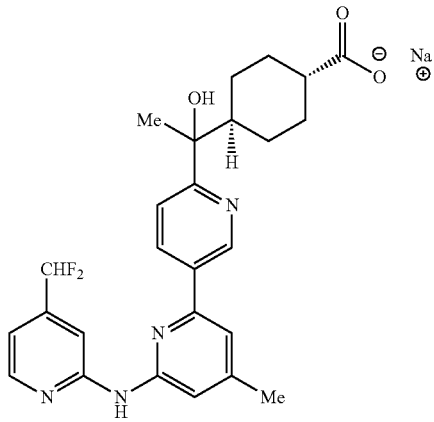 [SMILES: Cc1cc(Nc2cc(C(F)F)ccn2)nc(-c2ccc(C(C)(O)[C@H]3CC[C@H](C(=O)[O-])CC3)nc2)c1 ; [Na+]]

Sodium methoxide (25 wt % in MeOH, 52 µL, 0.21 mmol) was added to a solution of trans-4-[(1R or 1S)-1-(6-{[4-(difluoromethyl)pyridin-2-yl]amino}-4-methyl-2,3'-bipyridin-6'-yl)-1-hydroxyethyl]cyclohexanecarboxylic acid (Example 12, 100 mg, 0.21 mmol) in isopropanol (2.5 mL), and the resulting mixture heated to 70° C. for 1 hour. After allowing to cool to room temperature, EtOAc (5 mL) was added, and the mixture was concentrated in vacuo. This dilution and evaporation was repeated twice more. The residue was diluted with EtOAc (4 mL) and water (20 uL). The mixture was heated at 75° C. for 14 hours, then allowed to cool to room temperature. The resultant solids were collected by filtration. The white residue was washed with EtOAc:Hex (2 mL, 1:1) then dried for 14 hours in vacuo to afford sodium trans-4-[(1R or 1S)-1-(6-{[4-(difluoromethyl)pyridin-2-yl]amino}-4-methyl-2,3'-bipyridin-6'-yl)-1-hydroxyethyl]cyclohexanecarboxylate as a white solid. MS ESI calcd for $C_{26}H_{28}F_2N_4O_3$ [M+H]$^+$ 483. found 483. $^1$H NMR (500 MHz, DMSO-$d_6$) δ 10.00 (s, 1H), 9.12 (s, 1H), 8.43-8.26 (m, 3H), 7.66 (d, J=8.2 Hz, 1H), 7.42 (s, 1H), 7.34 (s, 1H), 7.09 (t, J=55.7 Hz, 1H), 7.02 (d, J=4.7 Hz, 1H), 4.93 (s, 1H), 2.34 (s, 3H), 1.88-1.56 (m, 5H), 1.42 (s, 3H), 1.14-0.93 (m, 5H). rhSyk IC$_{50}$=<0.5 nM.

Example 17

Ethyl trans-4-[(1R or 1S)-1-(6-{[4-(difluoromethyl)pyridin-2-yl]amino}-4-methyl-2,3'-bipyridin-6'-yl)-1-hydroxyethyl]cyclohexanecarboxylate

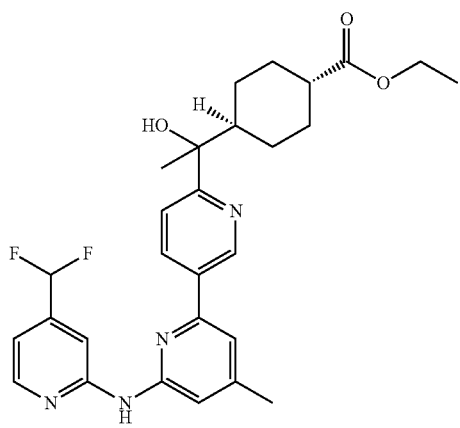

17

This example describes the procedure for conversion of (A1) to to (A) as shown in Scheme 8. To a mixture of trans-4-[(1R or 1S)-1-(6-{[4-(difluoromethyl)pyridin-2-yl]amino}-4-methyl-2,3'-bipyridin-6'-yl)-1-hydroxyethyl]cyclohexanecarboxylic acid (125 mg, 0.259 mmol), ethanol (0.076 ml, 1.295 mmol), and triphenylphosphine (resin-bound, 1.6 mmol g loading, 324 mg, 0.518 mmol) in tetrahydrofuran (3 mL) was added di-tert-butyl azodicarboxylate (119 mg, 0.518 mmol) at 20° C. The reaction mixture was stirred at 20° C. for 16 hours. The reaction mixture was diluted with TFA (1 mL) and water (1 drop). The mixture was stirred for 30 minutes. The mixture was then filtered through CELITE, washing with dichloromethane (3×10 mL). The filtrate was concentrated under reduced pressure to afford the crude residue TFA salt. The residue was diluted carefully with saturated aqueous sodium bicarbonate solution (25 mL) and ethyl acetate (100 mL). The organic layer was separated, washed with brine (25 mL), dried over magnesium sulfate, filtered, and concentrated under reduced pressure to afford the crude residue free base. The residue was purified by silica gel chromatography (0-75% ethyl acetate in hexanes, linear gradient) to afford ethyl trans-4-[(1R or 1S)-1-(6-{[4-(difluoromethyl)pyridin-2-yl]amino}-4-methyl-2,3'-bipyridin-6'-yl)-1-hydroxyethyl]cyclohexanecarboxylate. The product was dissolved in acetonitrile (1 mL) and diluted with water (3 mL). The resulting suspension was frozen and lyophilized to afford ethyl trans-4-[(1R or 1S)-1-(6-{[4-(difluoromethyl)pyridin-2-yl]amino}-4-methyl-2,3'-bipyridin-6'-yl)-1-hydroxyethyl]cyclohexanecarboxylate. MS ESI calcd. for $C_{28}H_{33}F_2N_4O_3$ [M+H]$^+$ 511. found 511. $^1$H NMR (500 MHz, DMSO-$d_6$) δ 10.00 (s, 1H), 9.13 (d, J=2.0 Hz, 1H), 8.39-8.35 (m, 2H), 8.32 (s, 1H), 7.67 (d, J=8.5 Hz, 1H), 7.42 (s, 1H), 7.33 (s, 1H), 7.09 (t, J=55.5 Hz, 1H), 7.02 (d, J=5.5 Hz, 1H), 5.06 (s, 1H), 3.99 (q, J=7.0 Hz, 2H), 2.34 (s, 3H), 2.12-2.04 (m, 1H), 1.94-1.88 (m, 1H), 1.86-1.70 (m, 3H), 1.43 (s, 3H), 1.30-1.08 (m, 8H). rhSyk IC$_{50}$=18 nM.

Example 18

2-Hydroxyethyl trans-4-[(1R or 1S)-1-(6-{[4-(difluoromethyl)pyridin-2-yl]amino}-4-methyl-2,3'-bipyridin-6'-yl)-1-hydroxyethyl]cyclohexanecarboxylate

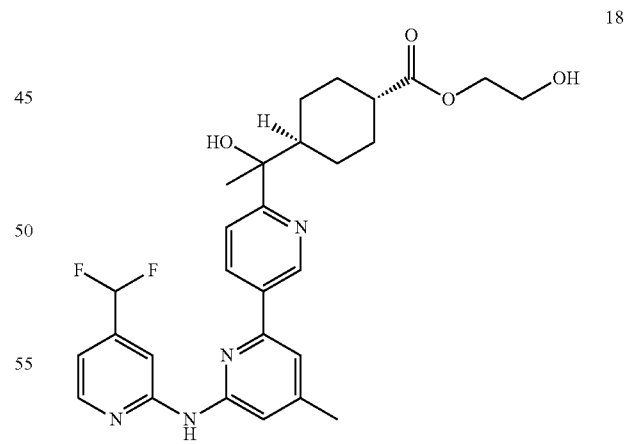

18

To a mixture of trans-4-[(1R or 1S)-1-(6-{[4-(difluoromethyl)pyridin-2-yl]amino}-4-methyl-2,3'-bipyridin-6'-yl)-1-hydroxyethyl]cyclohexanecarboxylic acid (150 mg, 0.311 mmol), 2-hydroxyethyl acetate (162 mg, 1.554 mmol), and triphenylphosphine (resin-bound, 1.6 mmol/g loading, 389 mg, 0.622 mmol) in tetrahydrofuran (3 mL) was added di-tert-butyl azodicarboxylate (143 mg, 0.622 mmol) at 20° C. The reaction mixture was stirred at 20° C. for 16 hours. The reaction mixture was diluted with TFA (1 mL) and water (1 drop). The mixture was stirred for 30 minutes. The mixture was then filtered through CELITE, washing with dichloromethane (3×10 mL). The filtrate was concentrated under reduced pressure to afford the crude residue TFA salt. The residue was diluted carefully with saturated aqueous sodium bicarbonate solution (25 mL) and ethyl acetate (100 mL). The organic layer was separated, washed with brine (25 mL), dried over magnesium sulfate, filtered, and concentrated under reduced pressure to afford the crude residue free base. The residue was purified by silica gel chromatography (0-100% ethyl acetate in hexanes, linear gradient, followed by 0-10% methanol in ethyl acetate, linear gradient) to afford 2-hydroxyethyl trans-4-[(1R or 1S)-1-(6-{[4-(difluoromethyl)pyridin-2-yl]amino}-4-methyl-2,3'-bipyridin-6'-yl)-1-hydroxyethyl]cyclohexanecarboxylate. The product was dissolved in acetonitrile (2 mL) and diluted with water (6 mL). The resulting suspension was frozen and lyophilized to afford 2-hydroxyethyl trans-4-[(1R or 1S)-1-(6-{[4-(difluoromethyl)pyridin-2-yl]amino}-4-methyl-2,3'-bipyridin-6'-yl)-1-hydroxyethyl]cyclohexanecarboxylate. MS ESI calcd. for $C_{28}H_{33}F_2N_4O_4$ $[M+H]^+$ 527. found 527. $^1H$ NMR (500 MHz, DMSO-$d_6$) δ 10.00 (s, 1H), 9.13 (d, J=2.0 Hz, 1H), 8.39-8.35 (m, 2H), 8.32 (s, 1H), 7.68 (d, J=8.0 Hz, 1H), 7.42 (s, 1H), 7.33 (s, 1H), 7.09 (t, J=56.0 Hz, 1H), 7.02 (d, J=5.0 Hz, 1H), 5.06 (s, 1H), 4.74 (t, J=5.5 Hz, 1H), 3.96 (t, J=5.0 Hz, 2H), 3.53-3.48 (m, 2H), 2.34 (s, 3H), 2.14-2.06 (m, 1H), 1.96-1.90 (m, 1H), 1.86-1.70 (m, 3H), 1.43 (s, 3H), 1.32-1.09 (m, 5H). rhSyk $IC_{50}$=3.4 nM.

Example 19

The following compounds were prepared according to procedures which were analogous to those described in Examples 17 and 18.

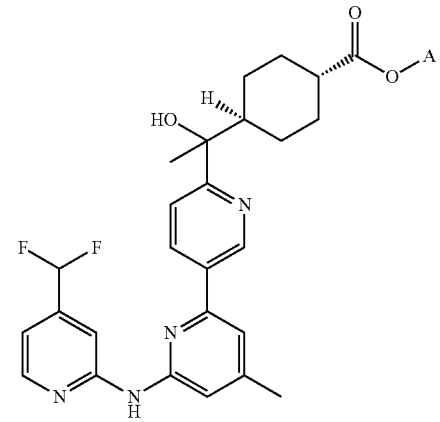

| Ex. No. | A | $IC_{50}$ (nM) | $[M+H]^+$ Calc'd | $[M+H]^+$ Obsv'd | Form | Name |
|---|---|---|---|---|---|---|
| 19-1 | benzyl | 35 | 573 | 573 | Free base | benzyl trans-4-[(1R or 1S)-1-(6-{[4-(difluoromethyl)pyridin-2-yl]amino}-4-methyl-2,3'-bipyridin-6'-yl)-1-hydroxyethyl]cyclohexanecarboxylate |
| 19-2 | propyl | 32 | 525 | 525 | Free base | propyl trans-4-[(1R or 1S)-1-(6-{[4-(difluoromethyl)pyridin-2-yl]amino}-4-methyl-2,3'-bipyridin-6'-yl)-1-hydroxyethyl]cyclohexanecarboxylate |
| 19-3 | propan-2-yl | 50 | 525 | 525 | Free base | propan-2-yl trans-4-[(1R or 1S)-1-(6-{[4-(difluoromethyl)pyridin-2-yl]amino}-4-methyl-2,3'-bipyridin-6'-yl)-1-hydroxyethyl]cyclohexanecarboxylate |
| 19-4 | butyl | 65 | 539 | 539 | Free base | butyl trans-4-[(1R or 1S)-1-(6-{[4-(difluoromethyl)pyridin-2-yl]amino}-4-methyl-2,3'-bipyridin-6'-yl)-1-hydroxyethyl]cyclohexanecarboxylate |

-continued

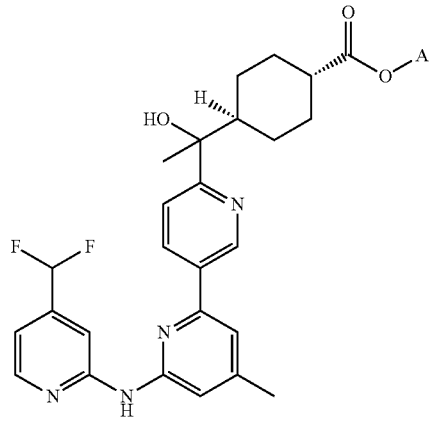

| Ex. No. | A | IC$_{50}$ (nM) | [M + H]$^+$ Calc'd | [M + H]$^+$ Obsv'd | Form | Name |
|---|---|---|---|---|---|---|
| 19-5 | ![](racemic sec-butyl) "Racemic" | 7 | 539 | 539 | Free base | butan-2-yl trans-4-[(1R or 1S)-1-(6-{[4-(difluoromethyl)pyridin-2-yl]amino}-4-methyl-2,3'-bipyridin-6'-yl)-1-hydroxyethyl] cyclohexanecarboxylate |
| 19-6 | isobutyl | 74 | 539 | 539 | Free base | 2-methylpropyl trans-4-[(1R or 1S)-1-(6-{[4-(difluoromethyl)pyridin-2-yl]amino}-4-methyl-2,3'-bipyridin-6'-yl)-1-hydroxyethyl] cyclohexanecarboxylate |
| 19-7 | pentyl | 100 | 553 | 553 | Free base | pentyl trans-4-[(1R or 1S)-1-(6-{[4-(difluoromethyl)pyridin-2-yl]amino}-4-methyl-2,3'-bipyridin-6'-yl)-1-hydroxyethyl] cyclohexanecarboxylate |
| 19-8 | neopentyl | 150 | 553 | 553 | Free base | 2,2-dimethylpropyl trans-4-[(1R or 1S)-1-(6-{[4-(difluoromethyl)pyridin-2-yl]amino}-4-methyl-2,3'-bipyridin-6'-yl)-1-hydroxyethyl] cyclohexanecarboxylate |
| 19-9 | hexyl | 190 | 567 | 567 | Free base | hexyl trans-4-[(1R or 1S)-1-(6-{[4-(difluoromethyl)pyridin-2-yl]amino}-4-methyl-2,3'-bipyridin-6'-yl)-1-hydroxyethyl] cyclohexanecarboxylate |
| 19-10 | heptyl | 670 | 581 | 581 | Free base | heptyl trans-4-[(1R or 1S)-1-(6-{[4-(difluoromethyl)pyridin-2-yl]amino}-4-methyl-2,3'-bipyridin-6'-yl)-1-hydroxyethyl] cyclohexanecarboxylate |
| 19-11 | octyl | >10,000 | 595 | 595 | Free base | octyl trans-4-[(1R or 1S)-1-(6-{[4-(difluoromethyl)pyridin-2-yl]amino}-4-methyl-2,3'-bipyridin-6'-yl)-1-hydroxyethyl] cyclohexanecarboxylate |

-continued

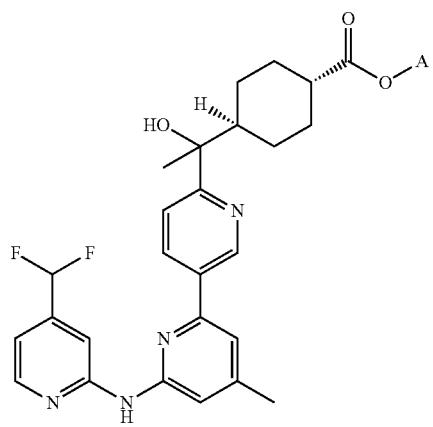

| Ex. No. | A | IC$_{50}$ (nM) | [M + H]$^+$ Calc'd | [M + H]$^+$ Obsv'd | Form | Name |
|---|---|---|---|---|---|---|
| 19-12 | cyclohexyl | 47 | 565 | 565 | Free base | cyclohexyl trans-4-[(1R or 1S)-1-(6-{[4-(difluoromethyl)pyridin-2-yl]amino}-4-methyl-2,3'-bipyridin-6'-yl)-1-hydroxyethyl] cyclohexanecarboxylate |
| 19-13 | tetrahydropyran-4-yl | 8.7 | 567 | 567 | Free base | tetrahydro-2H-pyran-4-yl trans-4-[(1R or 1S)-1-(6-{[4-(difluoromethyl)pyridin-2-yl]amino}-4-methyl-2,3'-bipyridin-6'-yl)-1-hydroxyethyl] cyclohexanecarboxylate |
| 19-14 | cyclohexylmethyl | 210 | 579 | 579 | Free base | cyclohexylmethyl trans-4-[(1R or 1S)-1-(6-{[4-(difluoromethyl)pyridin-2-yl]amino}-4-methyl-2,3'-bipyridin-6'-yl)-1-hydroxyethyl] cyclohexanecarboxylate |
| 19-15 | 2-methoxyethyl | 6.4 | 541 | 541 | Free base | 2-methoxyethyl trans-4-[(1R or 1S)-1-(6-{[4-(difluoromethyl)pyridin-2-yl]amino}-4-methyl-2,3'-bipyridin-6'-yl)-1-hydroxyethyl] cyclohexanecarboxylate |

-continued

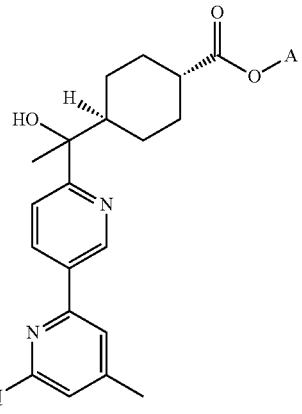

| Ex. No. | A | IC$_{50}$ (nM) | [M + H]$^+$ Calc'd | [M + H]$^+$ Obsv'd | Form | Name |
|---|---|---|---|---|---|---|
| 19-16 | (2-ethoxyethoxy)ethyl chain | 12 | 599 | 559 | Free base | 2-(2-ethoxyethoxy)ethyl trans-4-[(1R or 1S)-1-(6-{[4-(difluoromethyl)pyridin-2-yl]amino}-4-methyl-2,3'-bipyridin-6'-yl)-1-hydroxyethyl] cyclohexanecarboxylate |
| 19-17 | methyl ester chain | 4.3 | 555 | 555 | Free base | 2-methoxy-2-oxoethyl trans-4-[(1R or 1S)-1-(6-{[4-(difluoromethyl)pyridin-2-yl]amino}-4-methyl-2,3'-bipyridin-6'-yl)-1-hydroxyethyl] cyclohexanecarboxylate |
| 19-18 | dimethylamide chain | 1.2 | 568 | 568 | Free base | 2-(dimethylamino)-2-oxoethyl trans-4-[(1R or 1S)-1-(6-{[4-(difluoromethyl)pyridin-2-yl]amino}-4-methyl-2,3'-bipyridin-6'-yl)-1-hydroxyethyl] cyclohexanecarboxylate |
| 19-19 | morpholinoethyl | 8.7 | 596 | 596 | Free base | 2-{morpholin-4-yl)ethyl trans-4-[(1R or 1S)-1-(6-{[4-(difluoromethyl)pyridin-2-yl]amino}-4-methyl-2,3'-bipyridin-6'-yl)-1-hydroxyethyl] cyclohexanecarboxylate |
| 19-20 | dimethylaminoethyl | 2.3 | 554 | 554 | Free base | 2-(dimethylamino)ethyl trans-4-[(1R or 1S)-1-(6-{[4-difluoromethyl)pyridin-2-yl]amino}-4-methyl-2,3'-bipyridin-6'-yl)-1-hydroxyethyl] cyclohexanecarboxylate |
| 19-21 | (5-methyl-2-oxo-1,3-dioxol-4-yl)methyl | 5.2 | 595 | 595 | Free base | (5-methyl-2-oxo-1,3-dioxol-4-yl)methyl trans-4-[(1R or 1S)-1-(6-{[4-(difluoromethyl)pyridin-2-yl]amino}-4-methyl-2,3'-bipyridin-6'-yl)-1-hydroxyethyl] cyclohexanecarboxylate |

Example 20

[(Ethoxycarbonyl)oxy]methyl trans-4-[(1R or 1S)-1-(6-{[4-(difluoromethyl)pyridin-2-yl]amino}-4-methyl-2,3'-bipyridin-6'-yl)-1-hydroxyethyl]cyclohexanecarboxylate

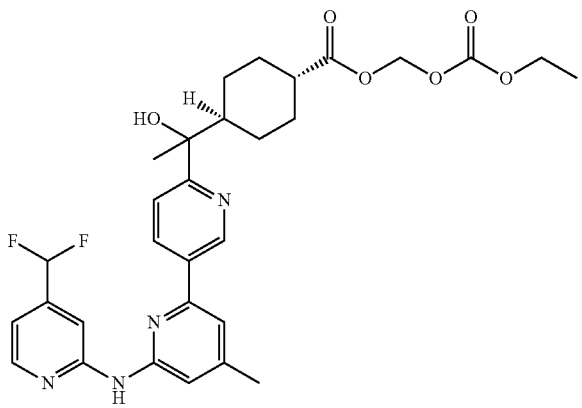

This example describes the procedure for conversion of (A1) to (C) as shown in Scheme 8. A mixture of trans-4-[(1R or 1S)-1-(6-{[4-(difluoromethyl)pyridin-2-yl]amino}-4-methyl-2,3'-bipyridin-6'-yl)-1-hydroxyethyl]cyclohexanecarboxylic acid (200 mg, 0.414 mmol), potassium carbonate (115 mg, 0.829 mmol), and sodium iodide (31 mg, 0.21 mmol) in DMF (3 mL) was stirred at 20° C. After 30 minutes, chloromethyl ethyl carbonate (55 mg, 0.39 mmol) was added and the reaction mixture was stirred at 20° C. After 16 hours, the reaction mixture was diluted with ethyl acetate (100 mL) and washed with water (4×20 mL). The organic layer was separated, washed with brine (20 mL), dried over magnesium sulfate, filtered, and concentrated under reduced pressure to afford the crude residue. The residue was purified by silica gel chromatography (0-100% ethyl acetate in hexanes, linear gradient) to afford [(ethoxycarbonyl)oxy]methyl trans-4-[(1R or 1S)-1-(6-{[4-(difluoromethyl)pyridin-2-yl]amino}-4-methyl-2,3'-bipyridin-6'-yl)-1-hydroxyethyl]cyclohexanecarboxylate. The product was dissolved in acetonitrile (2 mL) and diluted with water (6 mL). The resulting suspension was frozen and lyophilized to afford [(ethoxycarbonyl)oxy]methyl trans-4-[(1R or 1S)-1-(6-{[4-(difluoromethyl)pyridin-2-yl]amino}-4-methyl-2,3'-bipyridin-6'-yl)-1-hydroxyethyl]cyclohexanecarboxylate. MS ESI calcd. for $C_{30}H_{35}F_2N_4O_6$ $[M+H]^+$ 585. found 585. $^1$H NMR (500 MHz, DMSO-$d_6$) δ 10.00 (s, 1H), 9.13 (d, J=2.0 Hz, 1H), 8.39-8.35 (m, 2H), 8.32 (s, 1H), 7.68 (d, J=8.5 Hz, 1H), 7.42 (s, 1H), 7.33 (s, 1H), 7.09 (t, J=55.5 Hz, 1H), 7.02 (d, J=5.0 Hz, 1H), 5.64 (s, 2H), 5.07 (s, 1H), 4.13, (q, J=7.0 Hz, 2H), 2.34 (s, 3H), 2.22-2.15 (m, 1H), 1.96-1.90 (m, 1H), 1.88-1.70 (m, 3H), 1.43 (s, 3H), 1.32-1.10 (m, 8H). rhSyk $IC_{50}$=14 nM.

The following compounds were prepared according to procedures which were analogous to those described in Example 20.

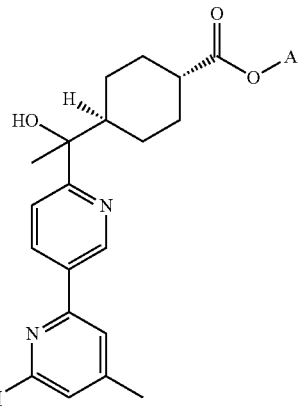

| Ex. No. | A | $IC_{50}$ (nM) | $[M+H]^+$ Calc'd | $[M+H]^+$ Obsv'd | Form | Name |
|---|---|---|---|---|---|---|
| 20-1 | ⟿O-C(O)-O-CH(CH₃)₂ | 19 | 599 | 599 | Free base | {[(propan-2-yloxy)carbonyl]oxy}methyl trans-4-[(1R or 1S)-1-(6-{[4-(difluoromethyl)pyridin-2-yl]amino}-4-methyl-2,3'-bipyridin-6'-yl)-1-hydroxyethyl]cyclohexanecarboxylate |
| 20-2 | ⟿CH(CH₃)-O-C(O)-O-Et "Racemic" | 69 | 599 | 599 | Free base | 1-[(ethoxycarbonyl)oxy]ethyl trans-4-[(1R or 1S)-1-(6-{[4-(difluoromethyl)pyridin-2-yl]amino}-4-methyl-2,3'-bipyridin-6'-yl)-1-hydroxyethyl]cyclohexanecarboxylate |

-continued

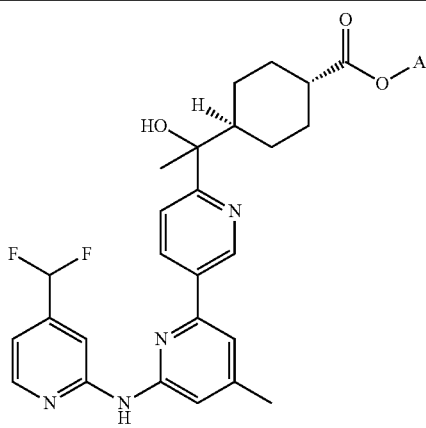

| Ex. No. | A | IC$_{50}$ (nM) | [M + H]$^+$ Calc'd | [M + H]$^+$ Obsv'd | Form | Name |
|---|---|---|---|---|---|---|
| 20-3 | "Racemic" | 110 | 613 | 613 | Free base | 1-{[(propan-2-yloxy)carbonyl]oxy}ethyl trans-4-[(1R or 1S)-1-(6-{[4-(difluoromethyl)pyridin-2-yl]amino}-4-methyl-2,3'-bipyridin-6'-yl)-1-hydroxyethyl] cyclohexanecarboxylate |
| 20-4 | "Racemic" | 510 | 653 | 653 | Free base | 1-{[(cyclohexyloxy)carbonyl]oxy}ethyl trans-4-[(1R or 1S)-1-(6-{[4-(difluoromethyl)pyridin-2-yl]amino}-4-methyl-2,3'-bipyridin-6'-yl)-1-hydroxyethyl] cyclohexanecarboxylate |
| 20-5 | "Isomer 1" | 32 | 599 | 599 | Free base | 1-[(ethoxycarbonyl)oxy]ethyl trans-4-[(1R or 1S)-1-(6-{[4-(difluoromethyl)pyridin-2-yl]amino}-4-methyl-2,3'-bipyridin-6'-yl)-1-hydroxyethyl] cyclohexanecarboxylate |
| 20-6 | "Isomer 2" | 21 | 599 | 599 | Free base | 1-[(ethoxycarbonyl)oxy]ethyl trans-4-[(1R or 1S)-1-(6-{[4-(difluoromethyl)pyridin-2-yl]amino}-4-methyl-2,3'-bipyridin-6'-yl)-1-hydroxyethyl] cyclohexanecarboxylate |
| 20-7 | "Isomer 1" | 100 | 613 | 613 | Free base | 1-{[(propan-2-yloxy)carbonyl]oxy}ethyl trans-4-[(1R or 1S)-1-{6-{[4-(difluoromethyl)pyridin-2-yl]amino}-4-methyl-2,3'-bipyridin-6'-yl)-1-hydroxyethyl] cyclohexanecarboxylate |
| 20-8 | "Isomer 2" | 50 | 613 | 613 | Free base | 1-{[(propan-2-yloxy)carbonyl]oxy}ethyl trans-4-[(1R or 1S)-1-(6-{[4-(difluoromethyl)pyridin-2-yl]amino}-4-methyl-2,3'-bipyridin-6'-yl)-1-hydroxyethyl] cyclohexanecarboxylate |

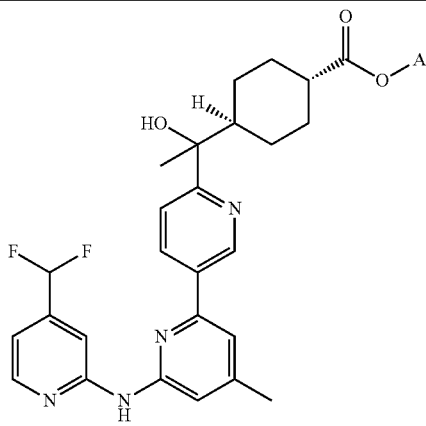

| Ex. No. | A | IC$_{50}$ (nM) | [M + H]$^+$ Calc'd | [M + H]$^+$ Obsv'd | Form | Name |
|---|---|---|---|---|---|---|
| 20-9 | "Isomer 1" | 140 | 653 | 653 | Free base | 1-{[(cyclohexyloxy)carbonyl]oxy}ethyl trans-4-[(1R or 1S)-1-(6-{[4-(difluoromethyl)pyridin-2-yl]amino}-4-methyl-2,3'-bipyridin-6'-yl)-1-hydroxyethyl]cyclohexanecarboxylate |
| 20-10 | "Isomer 2" | 190 | 653 | 653 | Free base | 1-{[(cyclohexyloxy)carbonyl]oxy}ethyl trans-4-[(1R or 1S)-1-(6-{[4-(difluoromethyl)pyridin-2-yl]amino}-4-methyl-2,3'-bipyridin-6'-yl)-1-hydroxyethyl]cyclohexanecarboxylate |

Example 21

(Acetyloxy)methyl trans-4-[(1R or 1S)-1-(6-{[4-(difluoromethyl)pyridin-2-yl]amino}-4-methyl-2,3'-bipyridin-6'-yl)-1-hydroxyethyl]cyclohexanecarboxylate

21

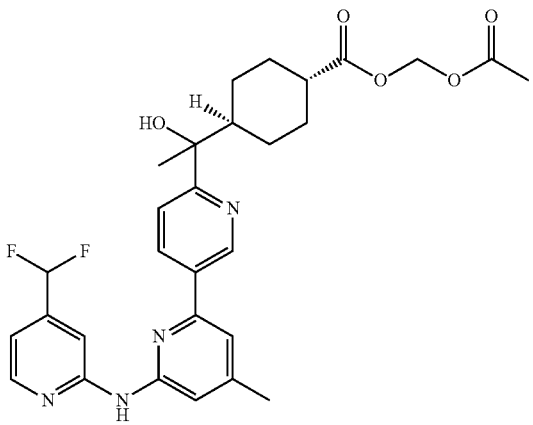

This example describes the procedure for conversion of (A1) to (B) as, shown in Scheme 8. To a solution of trans-4-[(1R or 1S)-1-(6-{[4-(difluoromethyl)pyridin-2-yl]amino}-4-methyl-2,3'-bipyridin-6'-yl)-1-hydroxyethyl]cyclohexanecarboxylic acid (200 mg, 0.414 mmol) in DMF was added potassium carbonate (115 mg, 0.829 mmol) and sodium iodide (12 mg, 0.083 mmol). After 75 minutes, bromomethyl acetate (0.041 ml, 0.41 mmol) was added and the reaction mixture was stirred for an additional 4 hours. The reaction mixture was then partitioned between ethyl acetate (20 mL) and aqueous saturated sodium bicarbonate (5 mL). The layers were separated, and then the organic layer was washed with water (3×5 mL) and brine (5 mL), dried over sodium sulfate, filtered, and concentrated under reduced pressure. The resulting residue was purified by silica gel chromatography (10-60% ethyl acetate in hexanes, linear gradient) to afford the product residue. The residue was lyophilized from acetonitrile and water to afford (acetyloxy)methyl trans-4-[(1R or 1S)-1-(6-{[4-(difluoromethyl)pyridin-2-yl]amino}-4-methyl-2,3'-bipyridin-6'-yl)-1-hydroxyethyl]cyclohexanecarboxylate. MS ESI calcd. for $C_{29}H_{33}F_2N_4O_5$ [M+H]$^+$ 555. found 555. $^1$H NMR (500 MHz, CDCl$_3$) δ 9.06 (d, J=1.7 Hz, 1H), 8.37 (d, J=5.8 Hz, 1H), 8.36 (dd, J=8.1 Hz, 2.2 Hz, 1H), 8.18 (s, 1H), 7.41 (s, 1H), 7.39 (d, J=7.6 Hz, 1H), 7.21 (s, 1H), 7.12 (s, 1H), 6.99 (d, J=5.1 Hz, 1H), 6.66 (t, J=56.0 Hz, 1H), 5.71 (s, 2H), 5.26 (s, 1H), 2.43 (s, 3H), 2.29-2.22 (m, 1H), 2.09 (s, 3H), 2.09-2.02 (m, 2H), 1.95-1.90 (m, 1H), 1.70-1.62 (m, 1H), 1.54 (s, 3H), 1.50-1.40 (m, 1H), 1.36-1.24 (m, 3H), 1.22-1.15 (m, 1H). rhSyk IC$_{50}$=11 nM.

The following compounds were prepared according to procedures which were analogous to those described in Example 21.

For example nos. 21-2 and 21-3, 1-chloroethyl acetate was used, which was prepared according to the procedure described in International Patent Application No. WO2011017634A2. For example nos. 21-4 and 21-5, 1-chloroethyl butyrate was used, which was prepared according to the procedure described in International Patent Application No. WO2011017634A2.

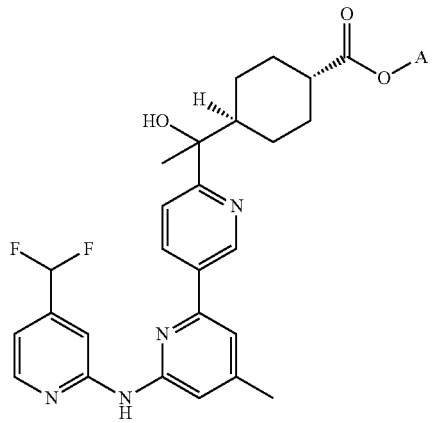

| Ex. No. | A | IC$_{50}$ (nM) | [M + H]$^+$ Calc'd | [M + H]$^+$ Obsv'd | Form | Name |
|---|---|---|---|---|---|---|
| 21-1 | | 71 | 597 | 597 | Free base | [(2,2-dimethylpropanoyl)oxy]methyl trans-4-[(1R or 1S)-1-(6-{[4-(difluoromethyl)pyridin-2-yl]amino}-4-methyl-2,3'-bipyridin-6'-yl)-1-hydroxyethyl] cyclohexanecarboxylate |
| 21-2 "Isomer 1" | | 4.3 | 569 | 569 | Free base | 1-(acetyloxy)ethyl trans-4-[(1R or 1S)-1-(6-{[4-(difluoromethyl)pyridin-2-yl]amino}-4-methyl-2,3'-bipyridin-6'-yl)-1-hydroxyethyl] cyclohexanecarboxylate |
| 21-3 "Isomer 2" | | 1.5 | 569 | 569 | Free base | 1-(acetyloxy)ethyl trans-4-[(1R or 1S)-1-(6-{[4-(difluoromethyl)pyridin-2-yl]amino}-4-methyl-2,3'-bipyridin-6'-yl)-1-hydroxyethyl] cyclohexanecarboxylate |
| 21-4 "Isomer 1" | | 23 | 597 | 597 | Free base | 1-[(2-methylpropanoyl)oxy]ethyl trans-4-[(1R or 1S)-1-(6-{[4-(difluoromethyl)pyridin-2-yl]amino}-4-methyl-2,3'-bipyridin-6'-yl)-1-hydroxyethyl] cyclohexanecarboxylate |
| 21-5 "Isomer 2" | | 33 | 597 | 597 | Free base | 1-[(2-methylpropanoyl)oxy]ethyl trans-4-[(1R or 1S)-1-(6-{[4-(difluoromethyl)pyridin-2-yl]amino}-4-methyl-2,3'-bipyridin-6'-yl)-1-hydroxyethyl] cyclohexanecarboxylate |
| 21-6 | | 15 | 569 | 569 | Free base | 2-(acetyloxy)ethyl trans-4-[(1R or 1S)-1-(6-{[4-(difluoromethyl)pyridin-2-yl]amino}-4-methyl-2,3'-bipyridin-6'-yl)-1-hydroxyethyl] cyclohexanecarboxylate |

Example 22

Methyl trans-4-[(1R or 1S)-1-(6-{[4-(difluoromethyl)pyridin-2-yl]amino}-4-methyl-2,3'-bipyridin-6'-yl)-1-hydroxyethyl]cyclohexanecarboxylate

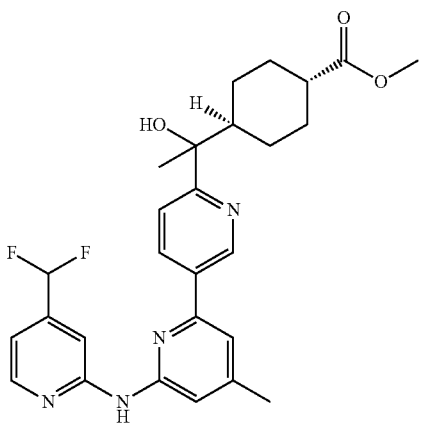

This example describes the procedure for conversion of (A1) to (D) as shown in Scheme 9. To a suspension of trans-4-[(1R or 1S)-1-(6-{[4-(difluoromethyl)pyridin-2-yl]amino}-4-methyl-2,3'-bipyridin-6'-yl)-1-hydroxyethyl]cyclohexanecarboxylic acid (125 mg, 0.259 mmol) in methanol (5 mL) and dichloromethane (5 mL) was added trimethylsilyldiazomethane (2.0 M in diethyl ether, 0.13 mL, 0.26 mmol) at 0° C. The reaction mixture was stirred at 0° C. until all gas evolution ceased. The reaction mixture was allowed to warm to ambient temperature and quenched by the addition of several drops of acetic acid. The reaction mixture was concentrated under reduced pressure and the residue was purified by silica gel chromatography (0-75% ethyl acetate in hexanes, linear gradient) to afford the product residue. The residue was dissolved in acetonitrile (1 mL) and diluted with water (3 mL). The resulting suspension was frozen and lyophilized to afford methyl trans-4-[(1R or 1S)-1-(6-{[4-(difluoromethyl)pyridin-2-yl]amino}-4-methyl-2,3'-bipyridin-6'-yl)-1-hydroxyethyl]cyclohexanecarboxylate. MS ESI calcd. for $C_{27}H_{31}F_2N_4O_3$ [M+H]$^+$ 497. found 497. NMR (500 MHz, DMSO-$d_6$) δ 10.00 (s, 1H), 9.13 (d, J=2.5 Hz, 1H), 8.39-8.35 (m, 2H), 8.32 (s, 1H), 7.68 (d, J=8.5 Hz, 1H), 7.42 (s, 1H), 7.33 (s, 1H), 7.09 (t, J=55.5 Hz, 1H), 7.02 (d, J=5.0 Hz, 1H), 5.06 (s, 1H), 3.53 (s, 3H), 2.34 (s, 3H), 2.14-2.06 (m, 1H), 1.94-1.90 (m, 1H), 1.88-1.70 (m, 3H), 1.43 (s, 3H), 1.31-1.08 (m, 5H). rhSyk IC$_{50}$=8 nM.

Example 23

(1R or 1S)-1-(6-{[4-(difluoromethyl)pyridin-2-yl]amino}-4-methyl-2,3'-bipyridin-6'-yl)-1-[trans-4-(hydroxymethyl)cyclohexyl]ethanol

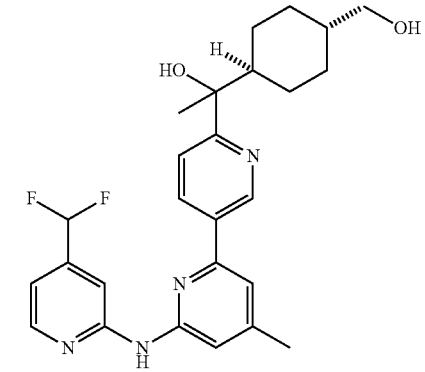

This example describes the procedure for conversion of (A1) to to (E) as shown in Scheme 10. To a mixture of trans-4-[(1R or 1S)-1-(6-{[4-(difluoromethyl)pyridin-2-yl]amino}-4-methyl-2,3'-bipyridin-6'-yl)-1-hydroxyethyl]cyclohexanecarboxylic acid (100 mg, 0.200 mmol) in dichloromethane (2.01 ml) at −78° C. was added diisobutylaluminum hydride (1.0 M in THF, 0.40 ml, 0.40 mmol). After 1 hour at −78° C., additional diisobutylaluminum hydride (1.0 M in THF, 0.40 ml, 0.40 mmol) was added and the mixture was allowed to warm to room temperature. After 18 hours, the reaction mixture was quenched with aqueous sodium potassium tartrate solution. The mixture was diluted with ethyl acetate and aqueous sodium bicarbonate solution. The organic layer was separated, and the aqueous layer was extracted with ethyl acetate. The organic layers were combined, washed with brine, dried over sodium sulfate, filtered, and concentrated under reduced pressure. The residue was purified by silica gel chromatography (0-100% ethyl acetate in hexanes, linear gradient) to afford (1R or 1S)-1-(6-{[4-(difluoromethyl)pyridin-2-yl]amino}-4-methyl-2,3'-bipyridin-6'-yl)-1-[trans-4-(hydroxymethyl)cyclohexyl]ethanol. MS ESI calcd. for $C_{26}H_{31}F_2N_4O_2$ [M+H]$^+$ 469. found 469. $^1$H NMR (500 MHz, DMSO-$d_6$) δ 10.00 (s, 1H), 9.12 (s, 1H), 8.38-8.30 (m, 3H), 7.67 (d, J=8.0 Hz, 1H), 7.42 (s, 1H), 7.33 (s, 1H), 7.09 (t, J=55 Hz, 1H), 7.02 (d, J=5.5 Hz, 1H), 4.99 (s, 1H), 4.29-4.26 (m, 1H), 3.15-3.10 (m, 2H), 2.34 (s, 3H), 1.82-1.72 (m, 2H), 1.71-1.65 (m, 1H), 1.64-1.58 (m, 1H), 1.43 (s, 3H), 1.24-1.12 (m, 2H), 1.11-1.00 (m, 1H), 0.86-0.78 (m, 2H), 0.73-0.64 (m, 1H). rhSyk IC$_{50}$=1 nM.

The suitability of the compounds of formula I as prodrugs of Syk inhibitors can be tested as described below.

Hydrolysis Assay: Analysis of Hydrolysis of Prodrug to Parent Species

The stability of 8 different prodrugs was investigated in human liver S9 microsomes. Incubations of prodrugs (10 μM) with liver S9 (1 mg protein/mL) were carried out at 37° C. in a phosphate buffer, pH 7.4, containing 1 mM NADPH. Control incubations contained BSA (1.1 mg/mL) instead of liver S9 microsomes. Aliquots were removed at 0, 5, 15, 30, 60 and 120 min, treated with 4 volumes of acetonitrile containing 2% formic acid and an internal standard, and centrifuged. The supernatants were analyzed by LC-MS/MS for prodrug disappearance and appearance of active drug. The half-life of the prodrug was calculated from the % prodrug remaining at different time points calculated from on the peak area ratio relative to t=0. The amount of active drug generated at the different time points was determined using a standard curve.

The table below shows the half-lives of the conversion of the prodrugs to the carboxylic acid.

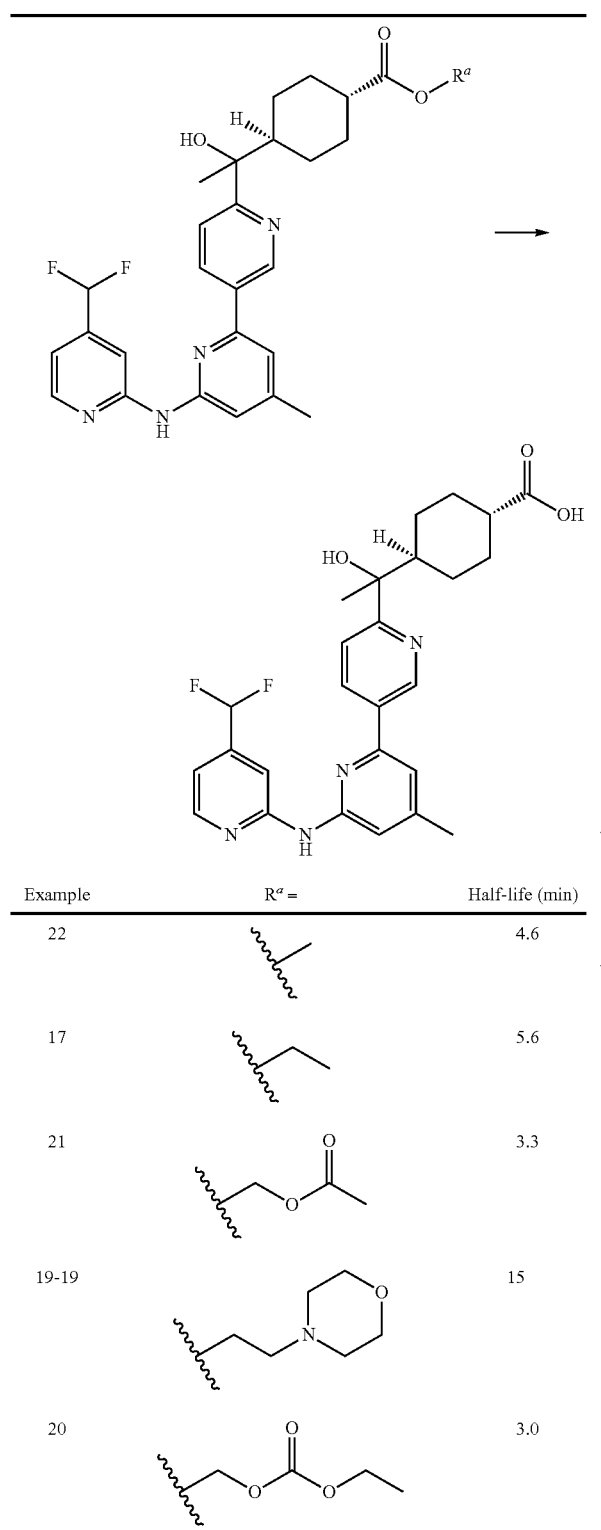

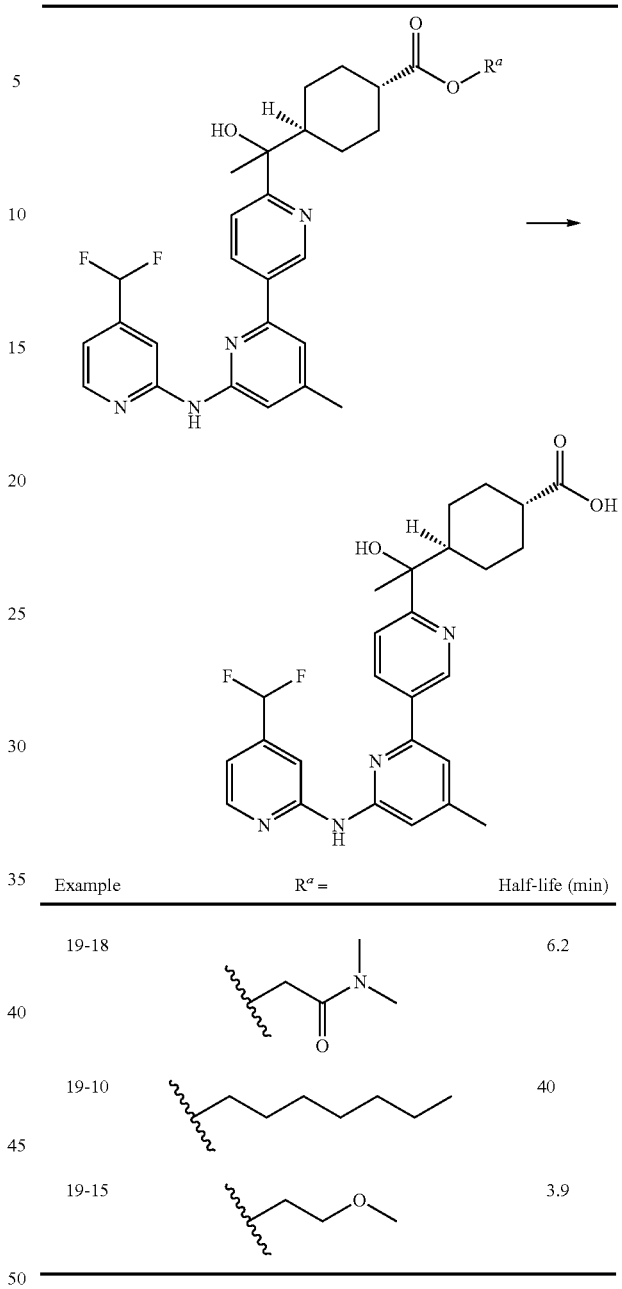

| Example | $R^a$ = | Half-life (min) |
|---|---|---|
| 22 | | 4.6 |
| 17 | | 5.6 |
| 21 | | 3.3 |
| 19-19 | | 15 |
| 20 | | 3.0 |
| 19-18 | | 6.2 |
| 19-10 | | 40 |
| 19-15 | | 3.9 |

What is claimed is:
1. A compound having formula Ia

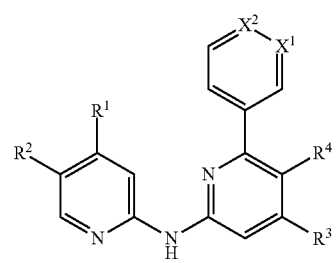

or a pharmaceutically acceptable salt thereof, wherein
R$^1$ is C$_{1-4}$alkyl, C$_{1-4}$fluoroalkyl, C$_{3-6}$cycloalkyl or C$_{1-4}$alkoxy;
R$^2$ is H or halogen;
R$^3$ is H, halogen, NR$^b$R$^c$, C$_{1-4}$alkyl, C$_{1-4}$haloalkyl, C$_{3-6}$cycloalkyl or C$_{1-4}$hydroxyalkyl;
Y is selected from the group consisting of a bond, —NH—, and —C(R$^5$)(R$^6$)—;
R$^5$ is H, OH, C$_{1-4}$ alkoxy or halogen;
R$^6$ is H, C$_{1-4}$alkyl, C$_{1-4}$haloalkyl, C$_{3-6}$cycloalkyl or C$_{1-4}$hydroxyalkyl;
Z is (a) an optionally benzofused C$_{3-6}$cycloalkyl optionally substituted with 1-5 groups independently selected from C$_{1-4}$alkyl, OR$^a$, CO$_2$R$^a$, and CONR$^b$R$^c$;
R$^a$ is selected from the group consisting of:
(i) H;
(ii) C$_{1-8}$ alkyl;
(iii) a group of the formula -M-R$^{CH}$, wherein
M is a bond or —(CH$_2$)$_{1-2}$—;
R$^{CH}$ is aryl or carbocycle optionally substituted with 1-3 groups independently selected from halo, C$_{1-4}$alkyl, or C$_{1-4}$alkoxy;
(iv) a group of the formula —(CH$_2$)$_{1-2}$—R$^e$ or —(CH$_2$)$_2$—O—(CH$_2$)$_2$—R$^e$ wherein
R$^e$ is CO$_2$R$^{e1}$, C(O)N(R$^{e2}$)$_2$, or —O(CO)R$^{e1}$;
R$^{e1}$ is C$_{1-4}$alkyl; and
R$^{e2}$ is H or C$_{1-4}$alkyl;
(v) a group of the formula —(CH$_2$)$_2$—R$^f$,
R$^f$ is OH, —OC$_{1-4}$alkyl, NH$_2$, —N(H)(C$_{1-4}$alkyl) or N(C$_{1-4}$alkyl)$_2$;
(vi) a group of the formula

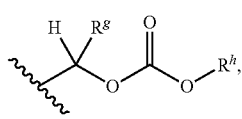

wherein
R$^g$ is H or C$_{1-4}$alkyl; and
R$^h$ is C$_{1-4}$alkyl, C$_{3-6}$cycloalkyl, or phenyl; and,
(vii) a group of the formula

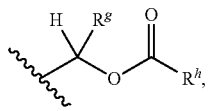

wherein R$^g$ and R$^h$ are as set forth above;
R$^b$ and R$^c$ are each independently selected from H and C$_{1-4}$alkyl.
2. The compound of claim 1 or a pharmaceutically acceptable salt thereof, wherein R$^a$ is H or C$_{1-4}$alkyl.
3. The compound of claim 1 or a pharmaceutically acceptable salt thereof, wherein Y is a bond and Z is (a)

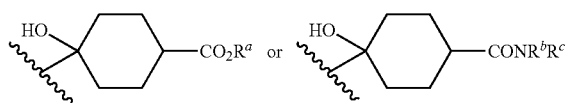

each optionally further substituted with 1 to 2 methyl groups.
4. The compound of claim 1 or a pharmaceutically acceptable salt thereof, wherein Y is —NH— or —C(R$^5$)(R$^6$)— and Z is cyclohexyl substituted with a group selected from CO$_2$R$^a$ and CONR$^b$R$^c$, and optionally further substituted with 1 or 2 methyl groups.
5. The compound of claim 4 or a pharmaceutically acceptable salt thereof, wherein Y is —C(R$^5$)(R$^6$)— and R$^5$ is OH.
6. The compound of claim 1 having the formula Ic:

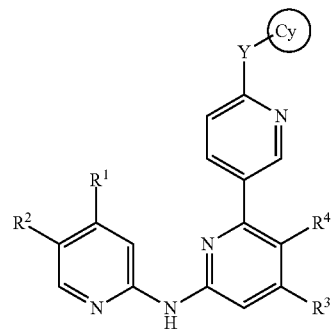

or a pharmaceutically acceptable salt thereof; wherein
Y is a bond or —NH—;
Cy is cyclohexyl substituted with CO$_2$R$^a$, and optionally further substituted with 1 to 2 methyl groups;
R$^4$ is H; and
R$^1$, R$^2$, R$^3$, R$^a$, R$^b$, and R$^c$ are as defined in claim 1.
7. The compound of claim 6 or a pharmaceutically acceptable salt thereof, wherein R$^a$ is H or C$_{1-4}$alkyl.
8. The compound of claim 6 or a pharmaceutically acceptable salt thereof, wherein Y is —NH—, and Cy is cyclohexyl substituted with CO$_2$R$^a$, and optionally further substituted with 1 to 2 methyl groups.
9. The compound of claim 1 having the formula Id:

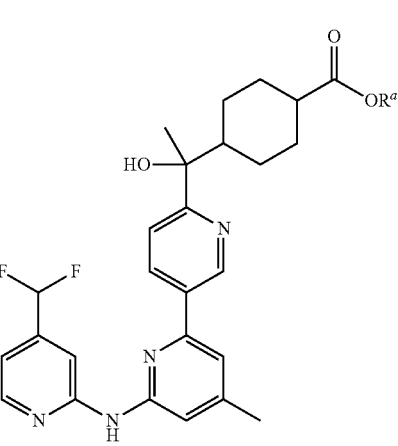

or a pharmaceutically acceptable salt thereof; wherein R$^a$ is selected from the group consisting of:
(i) H;
(ii) C$_{1-8}$alkyl;
(iii) a group of the formula -M-R$^{CH}$, wherein
M is a bond or —(CH$_2$)$_{1-2}$—;
R$^{CH}$ is aryl or carbocycle optionally substituted with 1-3 groups independently selected from halo, C$_{1-4}$alkyl, or C$_{1-4}$alkoxy;
(iv) a group of the formula —(CH$_2$)$_{1-2}$—R$^e$ or —(CH$_2$)$_2$—O—(CH$_2$)$_2$—R$^e$ wherein $R^e$ is $CO_2R^{e1}$, $C(O)N(R^{e2})_2$, or —O(CO)$R^{e1}$;
$R^{e1}$ is $C_{1-4}$alkyl; and
$R^{e2}$ is H or $C_{1-4}$alkyl;

(v) a group of the formula —$(CH_2)_2R^f$,
$R^f$ is OH, —$OC_{1-4}$alkyl, $NH_2$, —$N(H)(C_{1-4}$alkyl) or $N(C_{1-4}alkyl)_2$;

(vi) a group of the formula

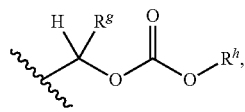

wherein
$R^g$ is H or $C_{1-4}$alkyl; and
$R^h$ is $C_{1-4}$alkyl, $C_{3-6}$cycloalkyl, or phenyl; and (vii) a group of the formula

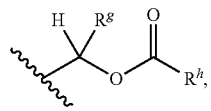

wherein $R^g$ and $R^h$ are as set forth above.

10. The compound of claim 1 selected from the group consisting of:
trans-4-(1-hydroxy-1-(4-methyl-6-(4-(trifluoromethyl) pyridin-2-ylamino)-2,3'-bipyridin-6'-yl)ethyl)cyclohexanecarboxylic acid;
trans-4-[(4-cyclopropyl-6-{[4-(difluoromethyl)pyridin-2-yl]amino}-2,3'-bipyridin-6'-yl)-1-hydroxyethyl]cyclohexanecarboxylic acid;
(1,2-cis)-4-[1-(6-{[4-(difluoromethyl)pyridin-2-yl] amino}-4-methyl-2,3'-bipyridin-6'-yl)-1-hydroxyethyl]-2-methylcyclohexanecarboxylic acid;
trans-4-[(6-{[4-(difluoromethyl)pyridin-2-yl]amino}-4-methyl-2,3'-bipyridin-6'-yl)-1-hydroxyethyl]cyclohexanecarboxylic acid;
trans-4-[1-hydroxy-1-{4-methyl-6-[(4-methylpyridin-2-yl)amino]-2,3'-bipyridin-6'-yl}ethyl]cyclohexanecarboxylic acid;
trans-4-[1-hydroxy-1-{6-[(4-methoxypyridin-2-yl) amino]-4-methyl-2,3'-bipyridin-6'-yl}ethyl]cyclohexanecarboxylic acid;
trans-4-[{6-[(4-cyclopropylpyridin-2-yl)amino]-4-methyl-2,3'-bipyridin-6'-yl}-1-hydroxyethyl)cyclohexanecarboxylic acid;
trans-4-[(4-methyl-6-{[4-(trifluoromethyl)pyridin-2-yl] amino}-2,3'-bipyridin-6'-yl)methyl]cyclohexanecarboxylic acid
trans-4-((6-(4-(difluoromethyl)pyridin-2-ylamino)-4-methyl-2,3'-bipyridin-6'-yl)-1-fluoroethyl)cyclohexanecarboxylic acid;
trans-4-[(4-methyl-6-{[4-(trifluoromethyl)pyridin-2-yl] amino}-2,3'-bipyridin-6'-yl)ethyl]cyclohexanecarboxylic acid;
(trans-4-[{6-[(5-fluoro-4-methylpyridin-2-yl)amino]-4-methyl-2,3'-bipyridin-6'-yl}-1-hydroxyethyl]cyclohexanecarboxylic acid;
trans-4-[[6-{[4-(difluoromethyl)pyridin-2-yl]amino}-4-(2-hydroxypropan-2-yl)-2,3'-bipyridin-6'-yl]-1-hydroxyethyl}cyclohexanecarboxylic acid
trans-4-[1-(6-{[4-(difluoromethyl)pyridin-2-yl]amino}-4-methyl-2,3'-bipyridin-6'-yl)-1-methoxyethyl]cyclohexanecarboxylic acid;
cis-4-hydroxy-4-(4-methyl-6-{[4-(trifluoromethyl)pyridin-2-yl]amino}-2,3'-bipyridin-6'-yl)cyclohexanecarboxylic acid;
5-hydroxy-5-(4-methyl-6-{[4-(trifluoromethyl)pyridin-2-yl]amino}-2,3'-bipyridin-6'-yl)-5,6,7,8-tetrahydronaphthalene-2-carboxylic acid;
4-hydroxy-2,2-dimethyl-4-(4-methyl-6-{[4-(trifluoromethyl)pyridin-2-yl]amino}-2,3'-bipyridin-6'-yl)cyclohexanecarboxylic acid;
trans-4-[cyclopropyl(hydroxy)(4-methyl-6-{[4-(trifluoromethyl)pyridin-2-yl]amino}-2,3'-bipyridin-6'-yl)methyl]cyclohexanecarboxylic acid;
methyl trans-4-[(6-{[4-(difluoromethyl)pyridin-2-yl] amino}-4-methyl-2,3'-bipyridin-6'-yl)-1-hydroxyethyl] cyclohexanecarboxylate;
ethyl trans-4-[1-(6-{[4-(difluoromethyl)pyridin-2-yl] amino}-4-methyl-2,3'-bipyridin-6'-yl)-1-hydroxyethyl] cyclohexanecarboxylate;
2-hydroxyethyl trans-4-[1-(6-{[4-(difluoromethyl)pyridin-2-yl]amino}-4-methyl-2,3'-bipyridin-6'-yl)-1-hydroxyethyl]cyclohexanecarboxylate;
benzyl trans-4-[1-(6-{[4-(difluoromethyl)pyridin-2-yl] amino}-4-methyl-2,3'-bipyridin-6'-yl)-1-hydroxyethyl] cyclohexanecarboxylate;
propyl trans-4-[1-(6-{[4-(difluoromethyl)pyridin-2-yl] amino}-4-methyl-2,3'-bipyridin-6'-yl)-1-hydroxyethyl] cyclohexanecarboxylate;
propan-2-yl trans-4-[1-(6-{[4-(difluoromethyl)pyridin-2-yl]amino}-4-methyl-2,3'-bipyridin-6'-yl)-1-hydroxyethyl]cyclohexanecarboxylate;
butyl trans-4-[1-(6-{[4-(difluoromethyl)pyridin-2-yl] amino}-4-methyl-2,3'-bipyridin-6'-yl)-1-hydroxyethyl] cyclohexanecarboxylate;
butan-2-yl trans-4-[1-(6-{[4-(difluoromethyl)pyridin-2-yl]amino}-4-methyl-2,3'-bipyridin-6'-yl)-1-hydroxyethyl]cyclohexanecarboxylate;
2-methylpropyl trans-4-[1-(6-{[4-(difluoromethyl)pyridin-2-yl]amino}-4-methyl-2,3'-bipyridin-6'-yl)-1-hydroxyethyl]cyclohexanecarboxylate;
pentyl trans-4-[1-(6-{[4-(difluoromethyl)pyridin-2-yl] amino}-4-methyl-2,3'-bipyridin-6'-yl)-1-hydroxyethyl] cyclohexanecarboxylate;
2,2-dimethylpropyl trans-4-[1-(6-{[4-(difluoromethyl)pyridin-2-yl]amino}-4-methyl-2,3'-bipyridin-6'-yl)-1-hydroxyethyl]cyclohexanecarboxylate;
hexyl trans-4-[1-(6-{[4-(difluoromethyl)pyridin-2-yl] amino}-4-methyl-2,3'-bipyridin-6'-yl)-1-hydroxyethyl] cyclohexanecarboxylate;
heptyl trans-4-[1-(6-{[4-(difluoromethyl)pyridin-2-yl] amino}-4-methyl-2,3'-bipyridin-6'-yl)-1-hydroxyethyl] cyclohexanecarboxylate;
octyl trans-4-[1-(6-{[4-(difluoromethyl)pyridin-2-yl] amino}-4-methyl-2,3'-bipyridin-6'-yl)-1-hydroxyethyl] cyclohexanecarboxylate;
cyclohexyl trans-4-[1-(6-{[4-(difluoromethyl)pyridin-2-yl]amino}-4-methyl-2,3'-bipyridin-6'-yl)-1-hydroxyethyl]cyclohexanecarboxylate;
cyclohexylmethyl trans-4-[1-(6-{[4-(difluoromethyl)pyridin-2-yl]amino}-4-methyl-2,3'-bipyridin-6'-yl)-1-hydroxyethyl]cyclohexanecarboxylate;
2-methoxyethyl trans-4-[1-(6-{[4-(difluoromethyl)pyridin-2-yl]amino}-4-methyl-2,3'-bipyridin-6'-yl)-1-hydroxyethyl]cyclohexanecarboxylate;

2-(2-ethoxyethoxy)ethyl trans-4-[1-(6-{[4-(difluoromethyl)pyridin-2-yl]amino}-4-methyl-2,3'-bipyridin-6'-yl)-1-hydroxyethyl]cyclohexanecarboxylate;

2-methoxy-2-oxoethyl trans-4-[1-(6-{[4-(difluoromethyl)pyridin-2-yl]amino}-4-methyl-2,3'-bipyridin-6'-yl)-1-hydroxyethyl]cyclohexanecarboxylate;

2-(dimethylamino)-2-oxoethyl trans-4-[1-(6-{[4-(difluoromethyl)pyridin-2-yl]amino}-4-methyl-2,3'-bipyridin-6'-yl)-1-hydroxyethyl]cyclohexanecarboxylate;

2-(dimethylamino)ethyl trans-4-[1-(6-{[4-(difluoromethyl)pyridin-2-yl]amino}-4-methyl-2,3'-bipyridin-6'-yl)-1-hydroxyethyl]cyclohexanecarboxylate;

[(ethoxycarbonyl)oxy]methyl trans-4-[1-(6-{[4-(difluoromethyl)pyridin-2-yl]amino}-4-methyl-2,3'-bipyridin-6'-yl)-1-hydroxyethyl]cyclohexanecarboxylate;

{[(propan-2-yloxy)carbonyl]oxy}methyl trans-4-[1-(6-{[4-(difluoromethyl)pyridin-2-yl]amino}-4-methyl-2,3'-bipyridin-6'-yl)-1-hydroxyethyl]cyclohexanecarboxylate;

1-[(ethoxycarbonyl)oxy]ethyl trans-4-[1-(6-{[4-(difluoromethyl)pyridin-2-yl]amino}-4-methyl-2,3'-bipyridin-6'-yl)-1-hydroxyethyl]cyclohexanecarboxylate;

1-{[(propan-2-yloxy)carbonyl]oxy}ethyl trans-4-[1-(6-{[4-(difluoromethyl)pyridin-2-yl]amino}-4-methyl-2,3'-bipyridin-6'-yl)-1-hydroxyethyl]cyclohexanecarboxylate;

1-{[(cyclohexyloxy)carbonyl]oxy}ethyl trans-4-[1-(6-{[4-(difluoromethyl)pyridin-2-yl]amino}-4-methyl-2,3'-bipyridin-6'-yl)-1-hydroxyethyl]cyclohexanecarboxylate;

(acetyloxy)methyl trans-4-[1-(6-{[4-(difluoromethyl)pyridin-2-yl]amino}-4-methyl-2,3'-bipyridin-6'-yl)-1-hydroxyethyl]cyclohexanecarboxylate;

[(2,2-dimethylpropanoyl)oxy]methyl trans-4-[1-(6-{[4-(difluoromethyl)pyridin-2-yl]amino}-4-methyl-2,3'-bipyridin-6'-yl)-1-hydroxyethyl]cyclohexanecarboxylate;

1-(acetyloxy)ethyl trans-4-[1-(6-{[4-(difluoromethyl)pyridin-2-yl]amino}-4-methyl-2,3'-bipyridin-6'-yl)-1-hydroxyethyl]cyclohexanecarboxylate;

1[(2-methylpropanoyl)oxy]ethyl trans-4-[1-(6-{[4-(difluoromethyl)pyridin-2-yl]amino}-4-methyl-2,3'-bipyridin-6'-yl)-1-hydroxyethyl]cyclohexanecarboxylate;

2-(acetyloxy)ethyl trans-4-[1-(6-{[4-(difluoromethyl)pyridin-2-yl]amino}-4-methyl-2,3'-bipyridin-6'-yl)-1-hydroxyethyl]cyclohexanecarboxylate;

methyl trans-4-[1-(6-{[4-(difluoromethyl)pyridin-2-yl]amino}-4-methyl-2,3'-bipyridin-6'-yl)-1-hydroxyethyl]cyclohexanecarboxylate; and 1-(6-{[4-(difluoromethyl)pyridin-2-yl]amino}-4-methyl-2,3'-bipyridin-6'-yl)-1-[trans-4-(hydroxymethyl)cyclohexyl]ethanol;

or a pharmaceutically acceptable salt thereof.

11. A pharmaceutical composition comprising a therapeutically effective amount of a compound of claim 1 or a pharmaceutically acceptable salt thereof, and a pharmaceutically acceptable carrier.

12. The compound of claim 9 or a pharmaceutically acceptable salt thereof, wherein $R^a$ is H or $C_{1-4}$alkyl.

13. The compound of claim 1 or a pharmaceutically acceptable salt thereof, wherein the compound is trans-4-[(6-{[4-(difluoromethyl)pyridin-2-yl]amino}-4-methyl-2,3'-bipyridin-6'-yl)-1-hydroxyethyl]cyclohexanecarboxylic acid.

\* \* \* \* \*